(12) United States Patent
Chiave

(10) Patent No.: US 12,369,660 B2
(45) Date of Patent: Jul. 29, 2025

(54) GARMENT ASSEMBLY FOR THE TRANSMISSION OF EXTERNAL LIGHT

(71) Applicant: Opnago B.V., Delft Zuid Holland (NL)

(72) Inventor: Silviya Della Chiave, Zuid Holland (NL)

( * ) Notice: Subject to any disclaimer, the term of this patent is extended or adjusted under 35 U.S.C. 154(b) by 0 days.

(21) Appl. No.: 17/794,120

(22) PCT Filed: Jan. 22, 2021

(86) PCT No.: PCT/IT2021/050020
§ 371 (c)(1),
(2) Date: Jul. 20, 2022

(87) PCT Pub. No.: WO2021/149088
PCT Pub. Date: Jul. 29, 2021

(65) Prior Publication Data
US 2023/0137401 A1 May 4, 2023

(30) Foreign Application Priority Data

Jan. 22, 2020 (IT) .................. 102020000001135
Sep. 30, 2020 (IT) .................. 102020000023002

(51) Int. Cl.
*A41D 13/01* (2006.01)
*A41D 31/04* (2019.01)
(Continued)

(52) U.S. Cl.
CPC .............. *A41D 31/04* (2019.02); *A41D 13/01* (2013.01); *G02B 6/102* (2013.01); *A61N 5/06* (2013.01);
(Continued)

(58) Field of Classification Search
CPC ........ A41D 31/04; A41D 13/01; G02B 6/102; A61N 5/06; A61N 2005/063;
(Continued)

(56) References Cited

U.S. PATENT DOCUMENTS 5,883,740 A * 3/1999 Chubb ................... A41D 7/006
2/125
2014/0074010 A1* 3/2014 Veres ....................... A61N 5/06
604/20
(Continued)

FOREIGN PATENT DOCUMENTS

CN 206660316 U * 11/2017

*Primary Examiner* — Carl H Layno
*Assistant Examiner* — Aya Ziad Bakkar
(74) *Attorney, Agent, or Firm* — Sandy Lipkin

(57) ABSTRACT

The invention relates to garment assembly (2) for the transmission of the external light radiations or light waves (11) to the skin (9) underneath the garment assembly, more particularly it relates to a garment assembly comprising at least a light wave guide (8) with one or more light wave collectors (4) and one or more light wave diffusers (3), for collecting light waves from the external side (6) of the garment assembly and transferring it to the skin covered by the garment assembly or by another garment. Said garment assembly may be composed by a first part, facing an external side of the garment assembly and a second part, facing an internal side of the garment assembly, which are permanently or detachably optically coupled to each other through said wave guide guiding means.

1 Claim, 15 Drawing Sheets

(51) Int. Cl.
*A61N 5/06* (2006.01)
*G02B 6/10* (2006.01)
(52) U.S. Cl.
CPC .................. *A61N 2005/063* (2013.01); *A61N 2005/0645* (2013.01); *A61N 2005/0657* (2013.01); *A61N 2005/0661* (2013.01)
(58) Field of Classification Search
CPC .... A61N 2005/0645; A61N 2005/0657; A61N 2005/0661
See application file for complete search history.

(56) References Cited

U.S. PATENT DOCUMENTS

2015/0062956 A1* 3/2015 Genier ................. G02B 6/0008
362/554
2019/0374792 A1* 12/2019 Tapper .................. A41D 1/002

* cited by examiner

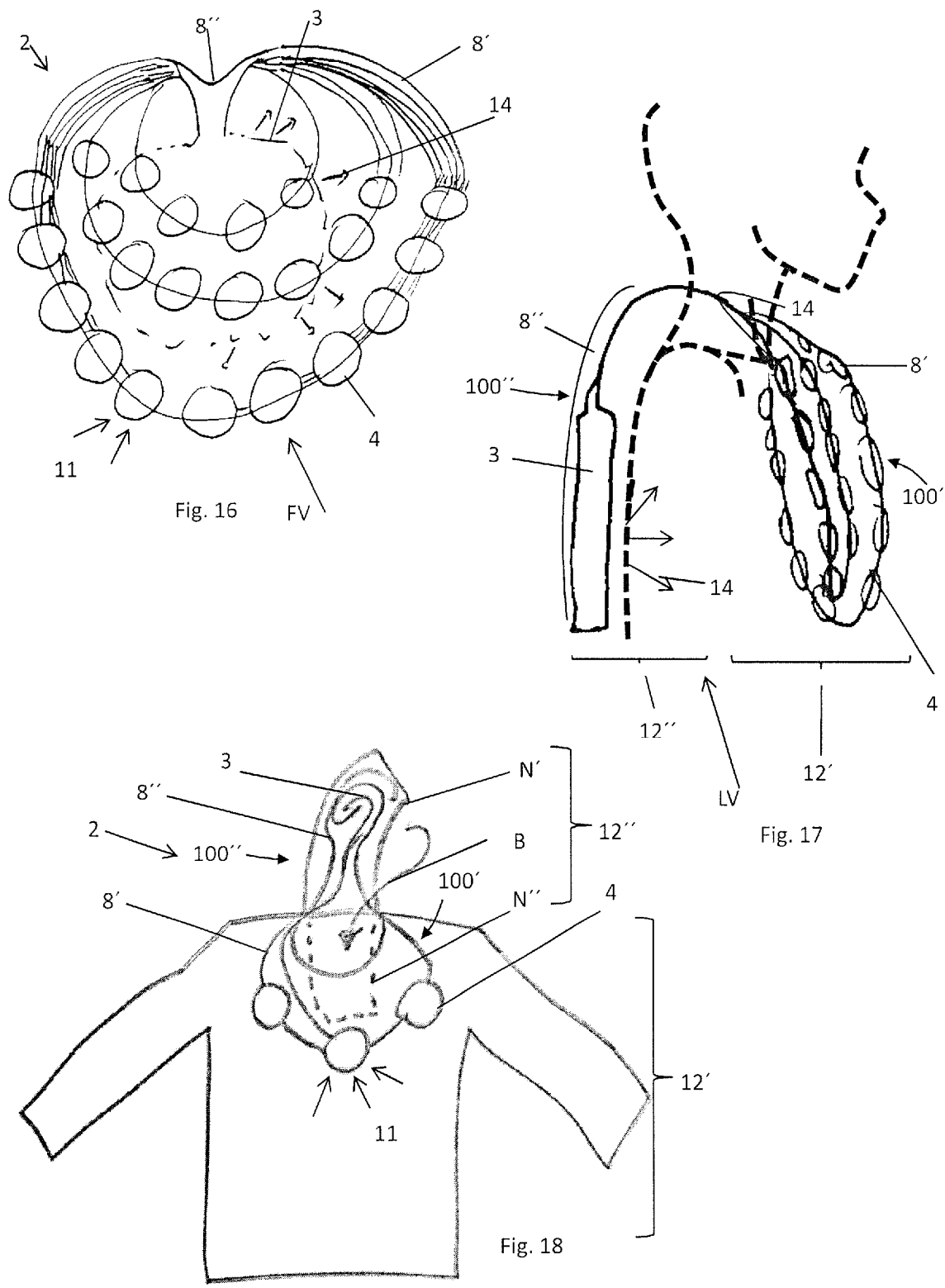

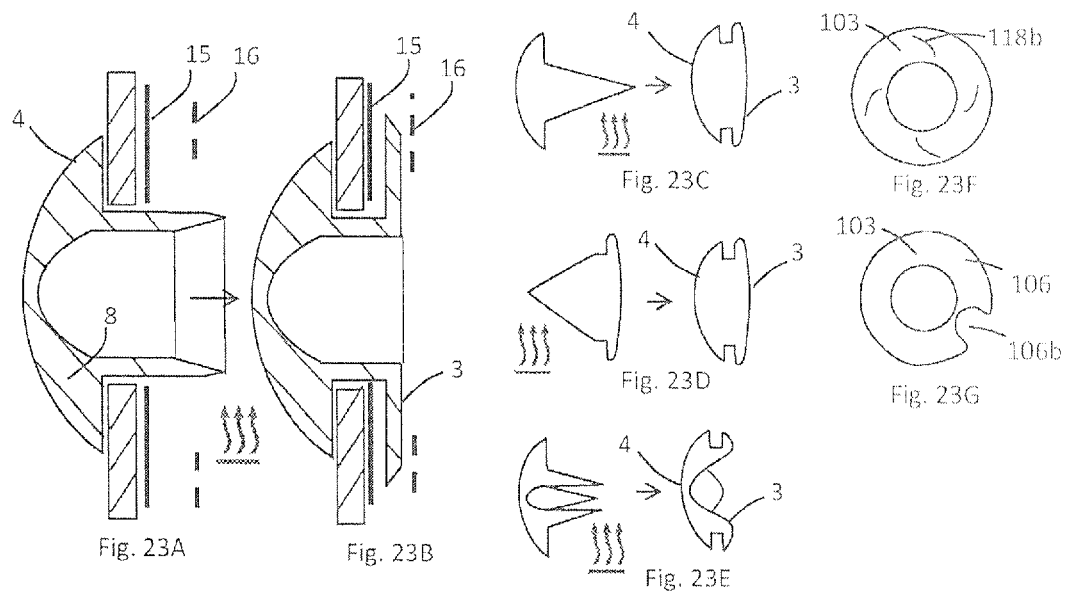
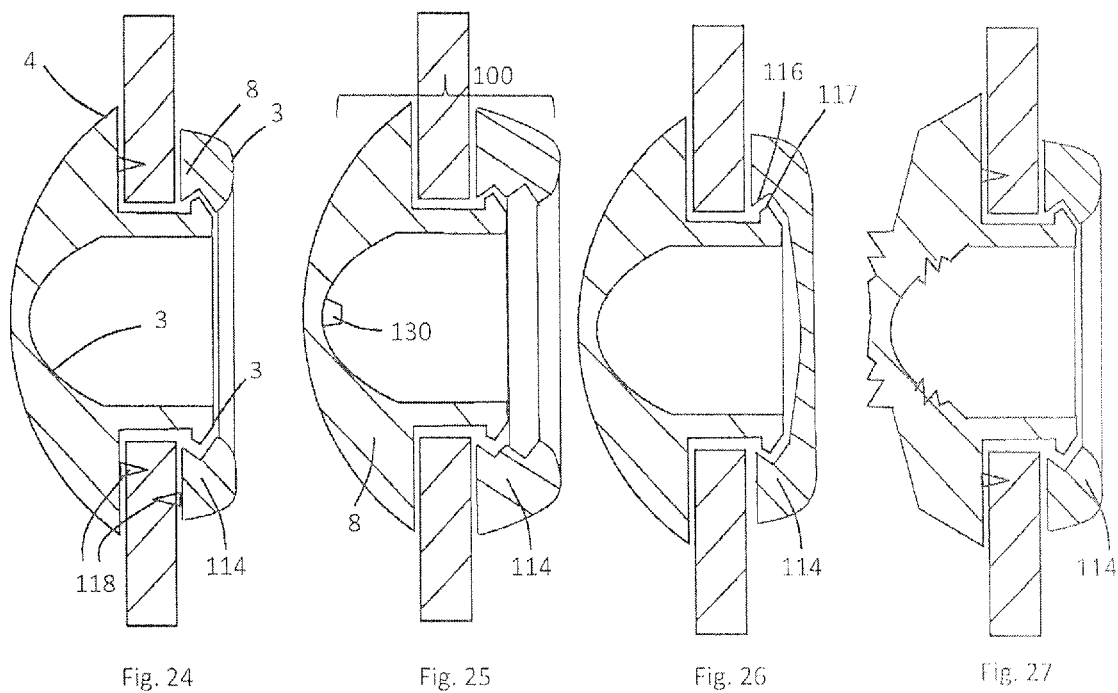

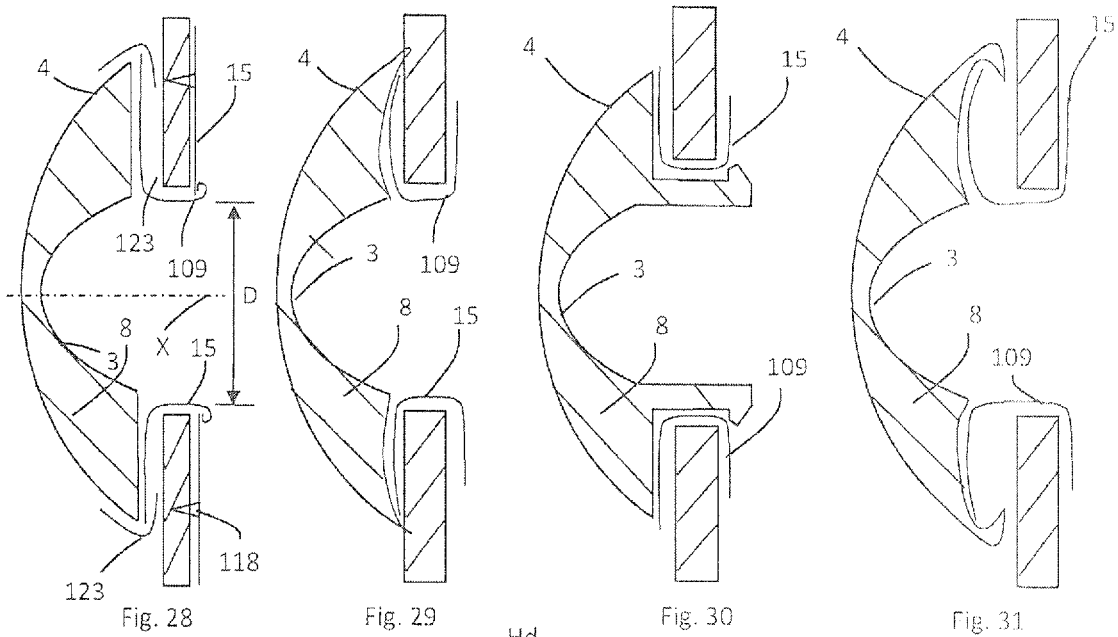
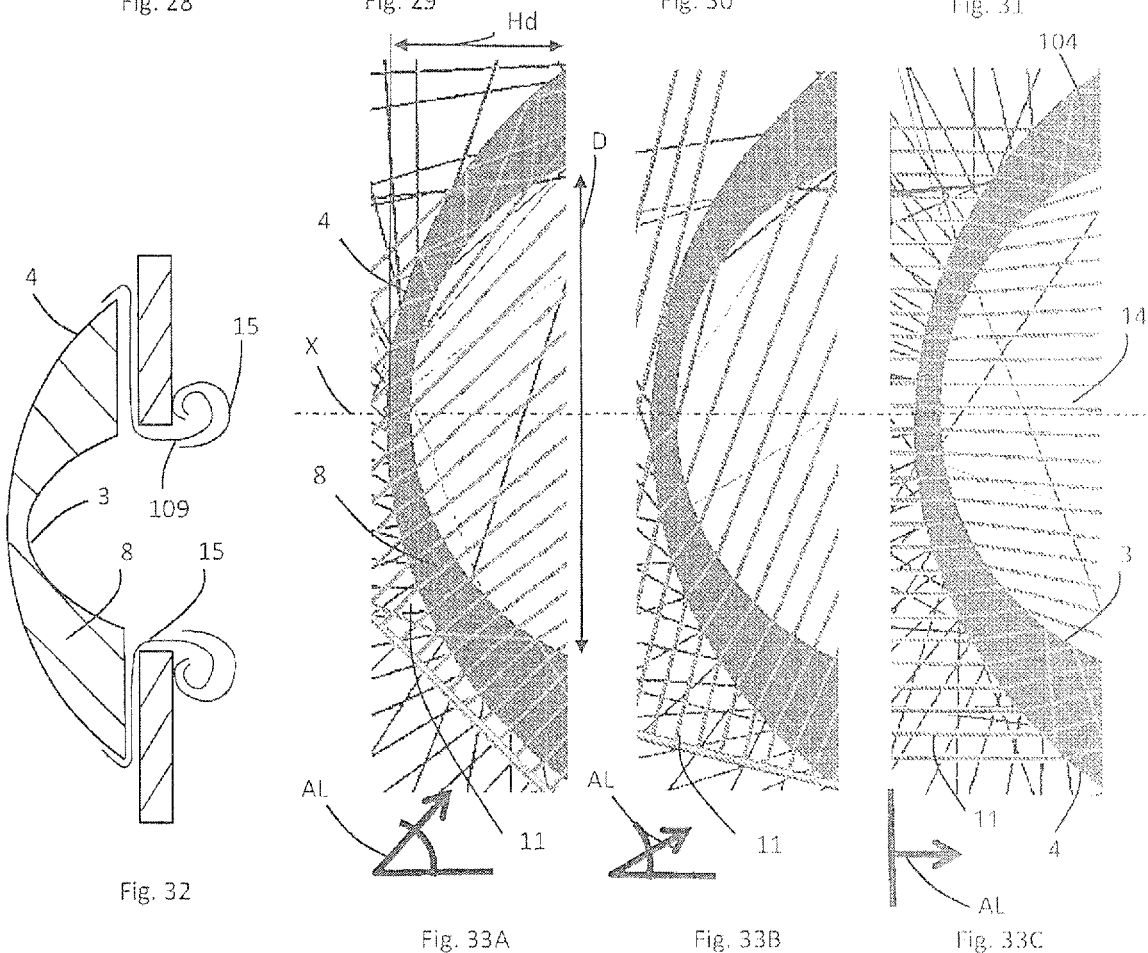

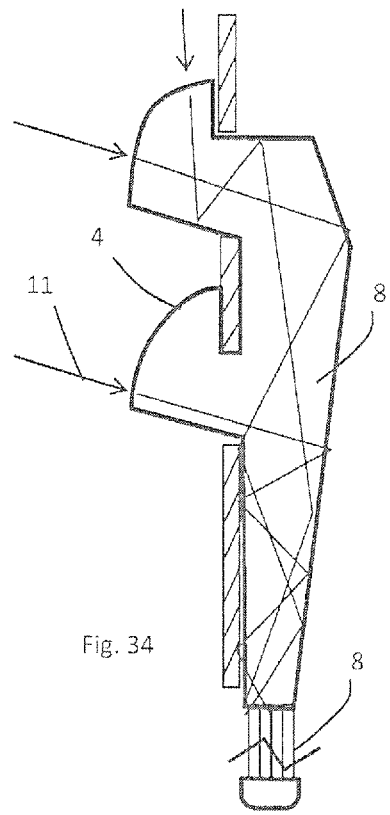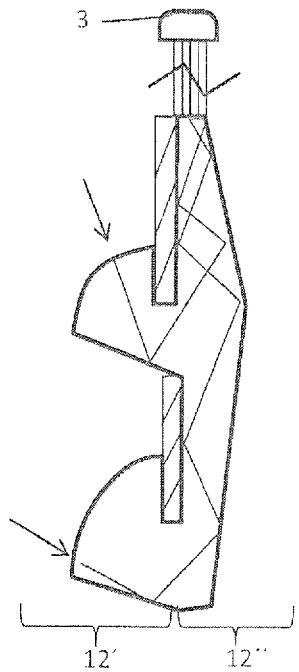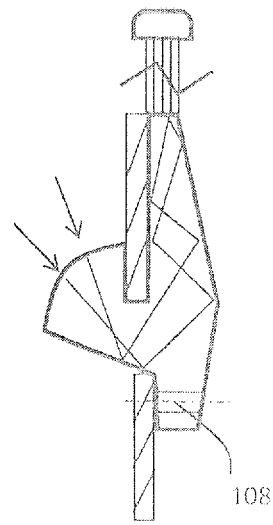
Fig. 34  Fig. 35  Fig. 36
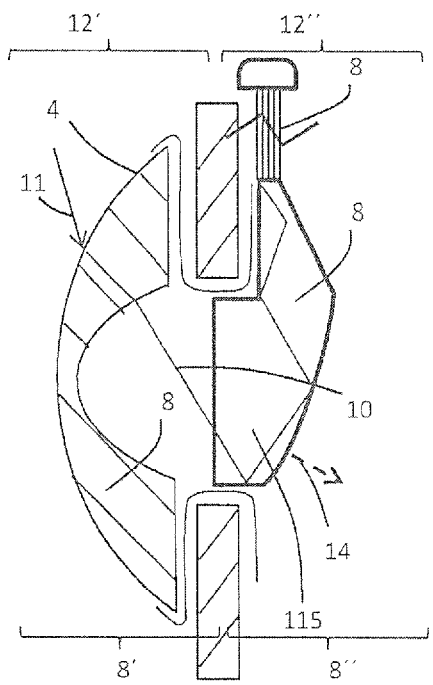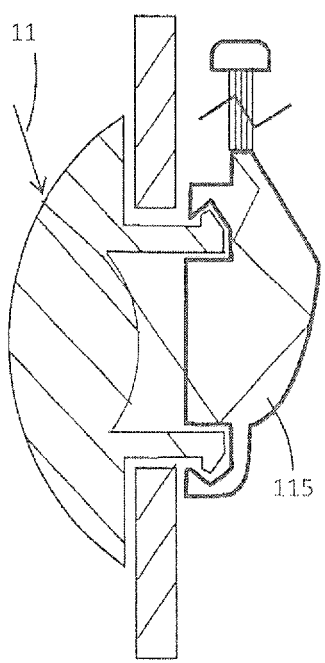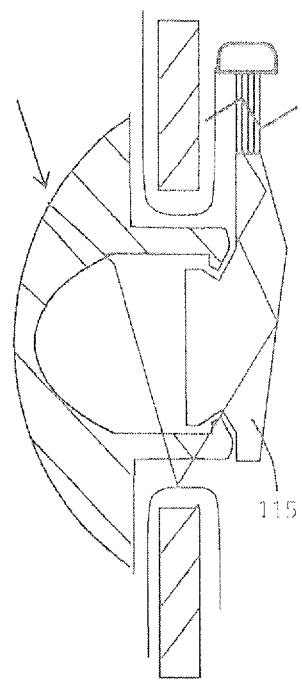
Fig. 37A  Fig. 37B  Fig. 37C

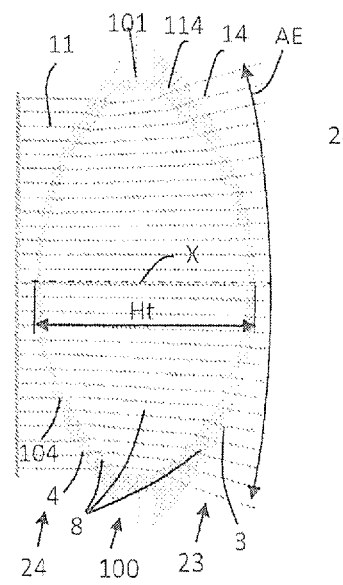 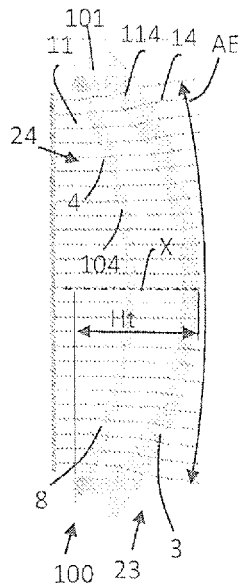 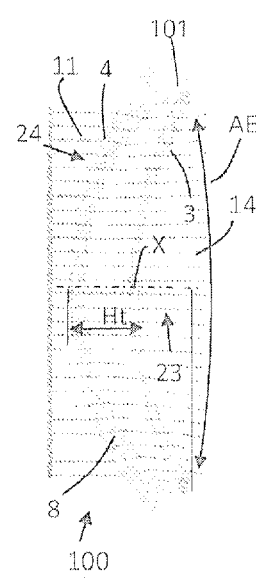 
Fig. 38A  Fig. 38B  Fig. 38C  Fig. 38D
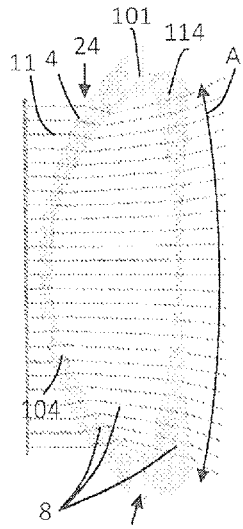 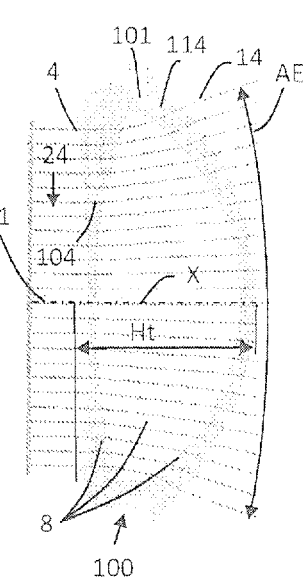 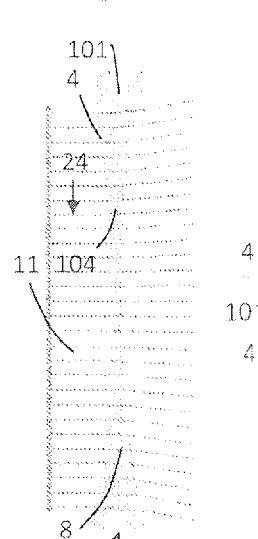
Fig. 38E  Fig. 38F  Fig. 38G  Fig. 39
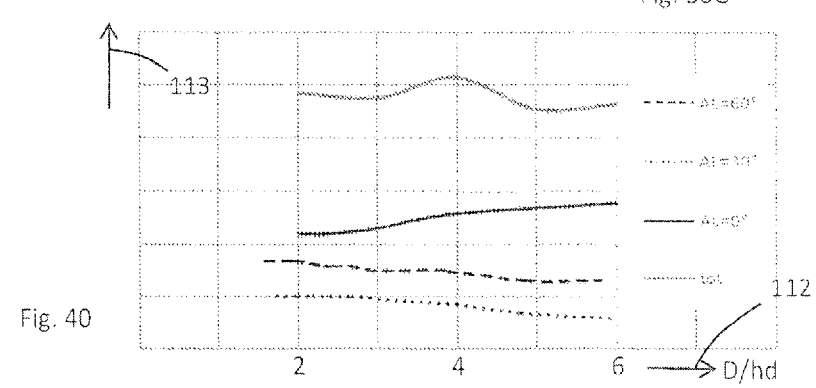
Fig. 40

GARMENT ASSEMBLY FOR THE TRANSMISSION OF EXTERNAL LIGHT

TECHNICAL FIELD

The invention relates to garment assembly for the transmission of the external light radiations or waves to the skin underneath the garment assembly, more particularly it relates to a garment assembly comprising at least a light wave guiding means with preferably one or more light wave collecting means and preferably one or more light wave diffusing means, for collecting light waves from the external side of the garment assembly and transferring it to the skin covered by the garment assembly or by another garment. Said garment assembly may be composed by a first part or first garment and a second part or second garment, which are detachably optically coupled to each other through said wave guiding means, in order to irradiate the skin underneath the second garment or second part or underneath both the first and the second garment, or first and second part, wherein the first part or first garment comprises said light wave collecting mean, and the second part or second garment comprises said light wave diffusing means.

BACKGROUND ART

People with limited exposure to sunlight, especially during winter time, older adults, people having darker skins, suffering from milk allergies, digestion or obesity problems, or adhering to a strict vegan diet, are at risk for vitamin D deficiency. Known as the sunshine vitamin, vitamin D is produced by the body in response to skin being exposed to sunlight. Vitamin D is essential for strong bones, because it helps the body use calcium from the diet. Traditionally, vitamin D deficiency has been associated with rickets, a disease in which the bone tissue does not properly mineralize, leading to soft bones and skeletal deformities.

However, increasingly, research is revealing the importance of vitamin D in protecting against a host of health problems and even reducing the symptoms and therefore the fatality rate or the coronavirus.

In addition, different kinds of light therapies are used to treat multiple health related problems. Those are used for seasonal affective disorder (SAD), depression, jet lag, sleep disorders, adjusting to a nighttime work schedule, dementia, acute or chronic pain. The used wavelength for phototherapy varies from the infrared to the ultra violet.

In order to reduce the need of any kind of light therapy, it would be desirable especially in winter months and in northern countries, to have clothing that allows the light, in particular UV light, preferably only UVB light, or even more preferably UVB light with the wavelength range of 285 nanometers to 310 nanometers, to reach the skin underneath the clothing itself. An object of the present invention is to provide a garment assembly having a single or a plurality of wave guiding means, guiding the light from the portion of the garment assembly exposed to the ambient light to the internal side of the garment assembly that covers the skin. The exposure to the sunlight, even when the body is almost fully covered by clothes, would reduce the onset of many health related problems, without the need of hospital visits and the use of complex machinery.

It is another object of the present invention a methods of irradiating skin under the clothes with natural UVB light.

It is another further object of the present invention a method of mechanically adjusting the light collecting power, or preferably the isolation power of the garment, and therefore to provide a garment assembly with wave guiding means having detachable wave collecting means. This allows adapting the garment assembly according to the available sun light, or heat, or to the desired amount of light waves wanted, or to the age and the skin of the user, wherein the removed light guiding means may, or may not, leave an opening in the garment.

It is still another object of the present invention to provide for garment assembly with wave guiding means having an electronic control system, optionally powered with photovoltaic elements, operable to control the light flow and wavelength through the wave guiding means of the garment assembly, which optionally could be used to recharge an external mobile device such as a smartphone or provide additional LED light on the skin or as a warning signal or as an intensity signal.

DISCLOSURE OF INVENTION

According to the invention is provided a garment assembly which may comprise at least a wave guiding means, a wave collecting means and a wave diffusing mean. The garment arrangement, may comprise a garment, or may be only a wearable optical arrangement.

The garment assembly embeds an optical arrangement, which may comprise a component or a plurality of components. Said optical arrangement may comprise at least a light guiding means, at least a wave or light collecting means, or optionally a wave concentrating means, which allows collecting the light waves from an external light source, preferably the solar light, and focusing it into the wave guiding means and at least a wave diffusing means, preferably situated or positioned on the internal side of the garment assembly, preferably oriented to the inward direction with respect to the a plane defined by internal surface of the garment assembly, or in the direction of the internal side of the garment assembly, more preferably toward the body of the user. The internal side and the external side of the garment assembly may be opposite to each other, may belong to the same or to different garments, or may be offset to each other. The internal side and the external side of the garment assembly may belong to the same surface of a garment, said surface being worn partially facing outside and partially facing the internal side, or the skin of the user, like for example a scarf, a foulard, or a hoodie. The light may be collected directly by an input end section of the wave guiding means itself, optionally an optical fiber with constant or variable cross section, said end section acting as a light input surface. The light may be diffused or radiated directly by an output end section of the wave guiding means itself, optionally an optical fiber, or a bunch thereof, with constant or variable cross section, which acts therefore as a light output surface positioned on the internal side of the garment assembly, preferably with the axis perpendicular to the end section being directed in an inward direction with respect to the a plane defined by internal surface of the garment assembly, or preferably in the direction of the internal side of the garment assembly, more preferably toward the body of the user. The inward direction may be defined by the orientation of the garment assembly, said orientation defining an internal surface facing an internal side of the garment assembly and an external surface facing an external side of the garment assembly. The optical fiber or the diffusing means may radiate light in the opposite side of the body and a reflecting means may be used to irradiate and/or diffuse light toward the body of the user. Alternatively the light may be collected by one or a plurality of wave collecting means, which make the collected light to converge into the smaller (with respect to the surface of the wave collector) section of the wave guiding means, enabling the light to be collected and supplied to a different area or zone of the garment assembly. In both cases, the input end of the wave guiding means may have a constant or a variable cross section, or preferably an increasing cross section in the direction of the light source or the light to be collected, allowing more light or waves to be collected. Visible and invisible light may be collected. Preferably the garment assembly may comprise a plurality of collecting means, so that more light can be captured, securing the transmission of the light even if a collecting means is broken or missing, which adds to the utility and durability of the garment assembly.

In embodiments according to the invention, a plurality of collecting means may be detached or exchanged in order to adjust the waves collecting power to the need. It is provided a piece of wearable garment assembly comprising a light guiding means or wave guiding means for guiding a light source from the external side of the garment assembly to the internal side of the garment assembly, so that, if no other wearable garments are situated between the skin of the user and said wearable garment assembly the source of light arrives on the skin of the user.

According to the embodiments of the invention, the end of the wave guiding means may be capped, so that at the end of the light guiding means the waves still inside the guide are absorbed, reflected or diffused e.g. using diffusing lenses to avoid a too high light concentration. The end cross section of the wave guiding means may alternatively be capped by a mirroring element which reflects the light back to the wave guiding means toward a different diffusing element or a diffusing portion of the wave guiding means.

Optionally, in all embodiments, in order to increase the light that reaches the skin a layer of reflecting means can be placed between the wave guiding means and the rest of the garment assembly, so that the wave guiding means are placed between the skin and the reflective means. The material of such reflective means may be aluminum, or another material with similar, higher or lower reflective properties in terms of UV reflection more preferably UVB reflection. Optionally, in order to increase the comfort of the garment assembly, a layer of material, tissue or fabric, which is transparent, or semitransparent with respect to a particular range of wavelengths, which can be a visible or an invisible light radiation, can be placed between the diffusing elements and the skin, so that at least a portion of the diffused light radiation can pass through it and can reach the skin, while the skin is at least partially protected from directly contacting the optical arrangement. Said layer may be in optionally made of following materials: LLDPE, PERSPEX, cyclic olefin copolimer (COC), PMMA, LLDPE, lidar borofloat, fluorinated polyamide, silicones and PDMS. In particular said layer is made by a translucent material that can be either extruded into thin filaments to be manufactured into a woven fabric, or transformed into a non-woven fabric, or into a thin layer.

Optionally the optical arrangement itself is coated or covered with a comfortable layer of material. Therefore the garment assembly may comprise, between the wave diffusing means and the skin of the user, a UV transparent or semitransparent or translucent layer of material, preferably the layer of material being a comfort component serving as the base of the garment of the garment assembly, preferably the wave diffusing means being integrated within said comfort component. Alternatively the layer of comfort material may be opaque with holes, or in form of a mesh, so that the majority of the light can pass through.

According to the embodiments of the invention, the garment assembly may comprise a thermal insulating component positioned underneath the collecting element, preferably between the wave diffusing means and the collecting means.

According to the invention, it is provided the use of an optical arrangement into or on a garment, or on several garments, said optical system or arrangement comprising at least a wave collecting means (e.g. lenses or mirrors or a combination thereof), at least a wave guiding means or a combination thereof and at least a wave diffusing means. Said optical arrangement may be made of one component or by a combination of several components. Said wave guiding means may have a first input end section or face adjacent to or facing the collecting means, and a second output section or face, facing the diffusing means. The front face of said lens or mirror or their combination may be positioned on the side of a light wave source on the external side of the garment assembly facing the ambient light and the second face of the wave guiding means may be positioned on the internal side of the garment assembly, preferably to the inward direction with respect to the plane defined by internal surface of the garment assembly, or preferably in the direction of the internal side of the garment assembly, more preferably toward the body of the user. Instead of lenses, mirrors or other optical elements may be used to build the optical assembly. Also a combination of lenses and mirrors may be implemented to carry out the invention, wherein said combination may be integrally included in a single piece, wherein said piece may have portions of material which are lenses and/or light guides and surfaces which may act at least partially as a mirror. Wave collecting means, wave guiding means and diffusing means are optically coupled; optionally at least two of them are an integral piece.

According to the invention, preferably it is provided the use of an optical system that may comprise a convergent lens or a convergent combination of lenses, having a front and a back face, preferably a optical fiber/wave guiding means or a combination of optical fibers or wave guiding means having a first face and a second face, wherein the first face is preferably positioned on the focus point or close to the focus point or comprising the focus point of the lens or lenses combination, into or on a wearable garment, or device, or a plurality of garments, preferably wherein the front face of the lens or lenses % combination is positioned on the side of a light source on the external side of the garment and the second face of the wave guiding means is positioned on the internal side of the garment. The use of an optical system on another garment means that the optical system can be positioned for example over the neck portion of a garment, with the wave collecting means being on the external side of the garment and exposed to the light and the wave diffusing means hanging inside, on the skin of the user.

There may be a big concentrator to place outside, or to expose to a light source outside a room or a building, with light guides going inside the room and connected to a phototherapy device or to a phototherapy garment, having the optical assembly. A hospital may use such assembly to power phototherapy devices with sunlight instead of using expensive energy consuming lamps.

In another embodiment of the invention the garment assembly may comprise two detachable parts: a second part or second garment with wave guiding means and wave diffusing means, adapted to be worn under or together with a first part, or first garment, optionally light opaque, in optical communication with the second part, or second garment, wherein said wave guiding means may extend from the second part, or second garment up to the optionally light opaque first part, or first garment or top garment, so that other garments can be worn in between.

In embodiments, preferably between the internal surface of the second garment and the wave guiding means there is a reflective layer that reflects the light directed outward back to the inward direction with respect to the plane defined by internal surface of the garment assembly, or in the direction of the internal side of the garment assembly, toward the body of the user.

In general, with "optically connected" it is meant connected together in order not to loose the guided light. Therefore, in order to be optically connected wave guiding means are also physically connected. In other embodiments of the invention the wave guiding means between the second part, or second garment and the first part, or first garment may be connected and disconnected, so that other garments can be worn in between, or different garments can be worn with the same internal garment. Several second parts, or second garments, may be alternated with the same first par, or first garment, or alternatively may be worn at the same time and may at the same time be coupled to the same first garment. The garment assembly, may comprise a second part, or second garment which is worn under or partially under the first part, or first garment, or alternatively a second part, or second garment worn on a different body portion. In another embodiments of the invention the wave guiding means on the first part, or first garment, optionally over garment, collects light only at their end sections, which are exposed to the ambient light or preferably have wave collecting means attached to the end sections, with said wave collecting means being exposed to the ambient light.

In another embodiment of the invention the second, optionally internal, part, or second garment, optionally undergarment, and the first part, optionally first garment, or external part, optionally over garment, are permanently attached to form an integral device, or piece of garment. The term attached to something should be understood within this application in the sense that two objects are either integral, or are kept in place very close or adjacent to each other, or touching each other, however not necessarily being glued, or welded together, or adhere directly on the contact area, or having the attaching means positioned in the contact areas, but eventually being kept in place through remotely situated attaching means, or through attaching means situated between the contact area of the object that are considered attached and another portion of the garment assembly.

In another embodiment of the invention the second part, may be exclusively formed by the light or wave guiding means. Alternatively first and second parts are portions of a garment assembly made of a single layer, or multiple layers, of fabric and an optical assembly passing therethrough and comprising a light collecting means on the external side and a light diffusing means on the internal side in optical communication with each other.

In another embodiment of the invention the second garment, or second part, may comprise a light permissive textile layer on the internal surface, between the wave guiding means and the skin, therefore underneath the wave guiding means, to make the wearing of the garment assembly comfortable.

In another embodiment of the invention the second garment, or second part, comprises a reflective layer on the external surface of the wave guiding means.

According to the embodiments, the second part may comprise at least a wave diffusing means on the internal surface, said second part extending between at least an upper opening and at least one lower opening, an orientation of said undergarment body defining an external surface and an internal surface.

In another embodiment of the invention the first part (12'), or first garment may further comprise at least one wave collecting means, wherein said plurality of wave guides are extending therefrom to guide the collected light toward the second part to irradiate the area underneath the garment assembly, underneath the internal side of the garment assembly. Alternatively said garment assembly, comprises a second garment body segment, or second part, and at least one over garment body, or first part, wherein said undergarment body, or second part, and said over garment body are adapted to be detachably joined to one another.

In all embodiments of the garment assembly the radiations diffused by the diffusing means comprise radiations with the wavelength of the visible and the invisible light spectrum, preferably radiations between 200 nm and 400 nm and between 780 nm and 140 nm, preferably radiations that are diffused by the diffusing means are UVA and UVB radiations, more preferably only UVB, even more preferably UVB radiations of about 293±10 nm. A specific radiation being diffused by the diffusing means imply the full length of the optical arrangement being at least partially transparent to that radiation bandwidth. In another embodiment of the invention wave guiding means may be provided, which may consist of a material that filters out, absorbs or reflects a specific range of wavelengths, e.g. UVA and UVB, or only UVA, or other unwanted wavelengths, and let UVB through. Light wave filters, in particular UVA filters, may be applied in any embodiment of the invention. Alternatively some filters of a certain light bandwidth may be applied to the skin covered by the garment assembly, or preferably by the light diffusing means of the garment assembly.

In order to make a UVA filter an additive can be used in the UVB transparent optical assemblies, or light guiding means. Alternatively, a replaceable optical element, which absorbs, at least partially, UVA light but is at least partially UVB transparent, of the optical assembly, which may be the collecting means, the guiding means, the diffusing means or all the mentioned optical elements and therefore the entire optical assembly, can be introduced in the connection of the wave guiding means. Since absorbing UVA light might deteriorate the material, the optical element that filters or absorbs UVA may be replaced. Gas or fluid may be used to filter a certain light bandwidth.

To filter a specific light bandwidth it is conceivable that at least a portion of the full length of the optical arrangement is at least partially opaque to that light band width. With the wording "filter", "to filter" or "filtering" is therefore intended any way (e.g. blocking, reflecting, scattering or absorbing) to at least partially excluding a certain light wavelength, or bandwidth, from passing through the entire component presenting that feature.

In another embodiment of the invention a garment assembly, optionally, maybe be provided, having an undergarment body having a shape for one of:
 a dress undergarment or second garment, or second part, wherein said upper opening may define one of a neckline or a bust line and said at least one lower opening defines a hemline, and said dress undergarment may be adapted to be worn under said first or external garment, wherein said external garment is a dress, a blouse undergarment, wherein said upper opening may define one of a neckline or a bust line and said at least one lower opening may define a waist hem, and said blouse undergarment may be adapted to be worn under said external garment, wherein said external garment is a blouse, a blouse undergarment, said blouse undergarment having a tube top shape, wherein said upper opening defines an upper bust line and said at least one lower opening defines a lower bust line hem, and said blouse undergarment is adapted to be worn under said external garment, a blouse undergarment, said blouse undergarment having a bra shape, wherein said upper opening defines one of a neckline or a bust line and said at least one lower opening defines a lower bust line hem, and said blouse undergarment is adapted to be worn under said external garment, a skirt undergarment, wherein said upper opening defines a waistline and said at least one lower opening defines a hemline, and said skirt undergarment is adapted to be worn under said external garment, wherein said external garment is a skirt, a tutu undergarment, wherein said upper opening defines a waistline and said at least one lower opening defines a hemline, said undergarment body tailored of said fabric arranged extending generally radially outwards from said waistline, and said skirt undergarment is adapted to be worn under said external garment, wherein said external garment is a tutu, a pants undergarment, wherein said upper opening defines a waistline and said at least one lower opening defines a pair of hemlines, and said pants undergarment is adapted to be worn under said external garment, wherein said external garment is pants, a culottes undergarment, wherein said upper opening defines a waistline and said at least one lower opening defines a pair of hemlines, and said culottes undergarment is adapted to be worn under said external garment, wherein said external garment is culottes, a shorts undergarment, wherein said upper opening defines a waistline and said at least one lower opening defines a pair of hemlines, and said shorts undergarment is adapted to be worn under said external garment, wherein said external garment is shorts, a panty shaped undergarment, wherein said upper opening defines a waistline and said at least one lower opening defines a pair of hip hemlines, and said panty shaped undergarment is adapted to be worn under said external garment, a bodysuit shaped undergarment, said bodysuit shaped garment being fabricated of a stretchable material, wherein said upper opening defines one of a neckline or a bust line, and said at least one lower opening defines a pair of hemlines, said bodysuit shaped undergarment comprising a torso covering and at least one of the sleeves, having a sleeve of any length, legless, and having a legging of any length, and said bodysuit shaped undergarment is adapted to be worn under said external garment or a unitary shaped undergarment, said unitary shaped garment being fabricated of a stretchable material, wherein said upper opening defines one of a neckline or a bust line, and said at least one lower opening defines a pair of hemlines, and said unitary shaped undergarment is adapted to be worn under said external garment.

In an embodiment the undergarment is a pair of trousers and the over garment is a jacket or a coat or sportswear. In this case it is to be understood that the trousers are worn vertically under the first garment, considering them in a lower position with respect to the height of a standing user, the wording under garment may also apply. Additionally a pair of trousers and a pair of leggings or tights may be in an over and undergarment relationship with each other.

In another embodiment of the invention is provided a garment combination, wherein a plurality of light diffusing wave guiding means are spatially arranged about said undergarment material in at least one of: A spiral, a circle, an open circle, a zig-zag pattern, an array pattern, a vertically aligned array pattern, a horizontally aligned array pattern, a diagonally aligned array pattern, a predetermined pattern representative of a phrase, a predetermined pattern representative of an image, and a random pattern. In an embodiment a garment assembly with the shape of a scarf or the like could be used half hanging outside the worn garments and half inside the garments passing for example through the neck, underneath all other garments, and having the wave collecting means on the outside portion and the diffusing means on the inside portion. Such a garment assembly can be worn on top of all garments and can be taken on and off easily. In this case the wave collecting means and diffusing means may be attached on the same side of the garment assembly, since after going through the neck, underneath all garments, the garment assembly will fold and the surface hanging outside is the same surface that is in contact with the skin.

According to the embodiments at least one of said plurality of wave diffusing wave guiding means may be at least one of: a) a single long wave guiding means; b) a plurality of generally parallel or interlaced wave guiding means e.g. optic fibers.

In embodiments the concentrators may have a portion of photovoltaic to power a screen, and or a signal which may be an alarm signal and elaborate the amount of uvb light collected with respect to the energy generated by the PV cells.

A small PV unit, eventually with energy storage, may send a Bluetooth signal to an external device, or to a device which is in a different position of the garment assembly.

Diffusing means may be positioned apart from each other, wherein the amount of space between them is equivalent to the average relative movement between the internal surface of the garment and the skin, so that with the movement of the garment a large portion of skin is irradiated with few diffusing means. In another embodiment, photovoltaic powered sensors may be implemented to regulate electronically the amount of total light, in order to alert the user about the achievement of the suitable daily charge of light.

The light collected by the photovoltaic module may be coming directly from the sun, or from the light collected by the collecting means. Therefore the light may be concentrated into a small photovoltaic module. The sensor data obtained by the sensor devices can be provided to an integrated photovoltaic powered computing device or transmitted to another device or to an app. The computing device can include wave sensors, uva and uvb sensors, heat sensors and data related to the body and in particular to the skin. For example data collected about the darkness on the skin to adapt the suitable quantity of daylight to the user, in order to automatically adapt the garment assembly, or to give a correct feedback to the user wearing it.

According to another embodiment, mechanic or electronic controlling means (which may be automatically or manually operated) may be implemented for controlling the wave flow through the guiding means, thereby controlling the light collected by the collecting means; thereby providing the wearer control over the light flow through the collecting means.

Sensors may also be implemented to electronically regulate the amount of total light, in order to alert the user about the achievement of the suitable daily charge of light. The sensor data obtained by the sensor devices can be provided to an integrated computing device or transmitted to an app. The computing device can include wave sensors, uva and uvb sensors, heat sensors and data related to the body and in particular to the skin. For example data collecting the darkness on the skin to adapt the suitable daily light quantity which is necessary, in order to automatically adapt the garment assembly to the user wearing it. The corporeal or skin data determined can be configured to extract skin quality data from the sensor data provided by the sensor devices.

A LED may be powered by a concentrated photovoltaic module (CPV) on the garment assembly. The garment assembly may have light collecting means that focus light into a small photovoltaic (PV) element in order to power UVB LEDs, preferably with an emission of UVB light having a wave length of about 293 nm. There may be a bluetooth communication between the optical assembly and a smartphone or another device. The Bluetooth may be powered by the photovoltaic module (PV). The Bluetooth transmit signals regarding the sun intensity, so that the smartphone may receive and may elaborate and show the data about the received radiation. The Bluetooth may also signal, if the light guiding means is connected to the garment or to the device that transmits light to the skin, so that it may be calculated or just be shown how much light therapy has been done and how much can still be supported by the skin. Bluetooth can communicate temperature of lightguide. Temperature measurement may not be necessary, if the light intensity is kept low by using multiple small concentrators each with a dedicated optical fiber, so that the concentration is not too high.

A mobile application for a smart device may be used in combination with the garment assembly to give the user feedback about the suitable exposure time, the light radiation received, or the equivalent vitamin D production, based on weather forecasts, or historical data, and/or gps data and/or skin type and/or age, and/or sun protection filter used, and/or optionally sensors in the smart device, or in the garment assembly and in wireless communication with the smart device. The input of a particular sport activity or of the outfit worn and/or the skin type may additionally be given as an input to the app. The mobile application may be configured to read a QR or barcode, preferably containing information about the garment assembly, and adjust the feedback given to the user based on the information given by the code, preferably about the type of garment assembly used.

Sensors, in particular UV sensors, in the garment assembly, in wireless communication with a smart device, may also be used to give feedback to the user. Alternatively the equivalent vitamin D production may be estimated based on other data, rather than UV radiation measurements, provided by a smart phone or a smart watch or a smart ring. Such data may be used to derive, preferably through an algorithm, the effective UV radiation based on other data such as luminosity, temperature, gps, date, incoming light orientation or a combination thereof.

In another embodiment the garment assembly further comprises a thermal barrier/thermal isolation member between at least one of said at least one irradiating element and an internal space between the external and the internal surfaces of the garment assembly.

According to the invention materials used for the optical elements, of the optical assembly, which may include concentrators, diffusing means, mirrors, reflectors, wave guiding means and interconnecting elements might be any suitable material, e.g. light transparent of semitransparent materials, UVA and UVB transparent or semitransparent materials, materials that are generally only partially wave transparent and materials that reflect the light, so that it can be guided through air, vacuum or gas. With partially light transparent included materials that fully or partially filter, absorb or reflect light in certain wavelengths, materials that fully or partially filter all the light wavelengths, materials which properties deteriorate with light exposition but are particularly cheap or particularly suitable for a determinate application and preferably materials that are UV transparent or semitransparent. A gas or a fluid may be part of the optical assembly for example to filter a specific light bandwidth.

Lenses, mirrors, optical windows, beam splitters, prisms, polarizer, wave plates, optical filters etc. UV mirrors and lenses also in aspheric versions, and coatings might be used. However, there are certain special aspects to be observed for applications in the UV region. For vitamin D phototherapy preferably materials with low absorption in the ultraviolet spectral region are advantageous. If the length of the wave guiding means is short enough or the light or wave intensity is not high compared to the laser applications, also materials that are only semitransparent to the required wavelength, or have a low trasmittance for said wavelenght, can be used. For phototherapy where low or no ultraviolet light is involved, other materials can be used. Any optical element, or portion of the optical assembly, may be at least partially coated internally (e.g. in the case of a hollow or concave optical element) or externally (e.g. in the case of a solid or convex optical element) with a reflective layer. The reflective layer may be for example aluminum silver or any other suitable material.

To obtain a garment assembly which is suitable to a particular phototerapy, any material which is transparent to a certain light wavelength (visible or invisible) may be used.

Preferably, materials that are transparent in the ultraviolet spectral region may be used. Examples might be certain crystalline optical materials like $CaF_2$ and some borates. UV optics made from highly purified calcium fluoride ($Ca_{F2}$). Purified fluorides such as magnesium fluoride (MgF2) and lithium fluoride (LiF) may be used. In addition to good UV transparency, such fluorides also offer good infrared properties up to wavelengths of 5 μm and beyond. According to the invention, as an alternative, UV-grade fused silica may be used even for wavelengths down to ≈200 nm, whereas the cheaper standard-grade fused silica has significant attenuation already below 260 nm. Materials chosen for making dielectric coatings, for example in the form of anti-reflection coatings, for example magnesium fluoride (MgF2) might be also implemented. Some silica optical fibers with high hydroxyl ion (OH) silica core show a very low attenuation of UVB and are suitable optical media for wave guiding means, collecting means or diffusing means. However silica fibers with low OH are also suitable in certain cases, for example for an option with less UVB light transmittance or for the transmission of a particular wavelength. Alternatively LLDPE and PERSPEX Acrylglas-Plates materials which are transparent to UVB and UVA may be used. Other suitable materials are cyclic olefin copolimer (COC), uvb transp polimer perspex (PMMA or acrylic glass), LLDPE, quartz glass, furniture glass, lidar borofloat, UV-transparent fluorinated polyimide and PDMS (which has for example a transmittance of 70% for 254 nm UV light). With the term transparency, it is meant at least a partial light transparency (preferably of visible and invisible wavelength) higher than 30%, preferably higher than 50%, or more preferably higher that 60% of the visible and invisible light wavelengths. In particular with UVB transparency (preferably of UVB wavelength between 280 nm to 315 nm, even more preferably between 293 nm and 298 nm) it is meant at least a partial light transparency higher than 30%, preferably higher than 50%, or more preferably higher that 60% in said total UVB ranges. Pure PMMA and COC exhibit about a 90% light transmission of the overall light spectrum, however the transparency decreases at lower wavelengths. With the term UVA opacity (or visible light opacity), in case an UVA filter (or a visible light filter) is used, it is meant an UVA opacity (or visible light opacity) of at least 10%, preferably higher than 50%, more preferably higher than 80%, even more preferably higher than 90%. Generally the terms PMMA or acryl or Plexiglas or Perspex refers to a polymer that is partially doped with other materials that absorb UV light, since this is a characteristic that is whished in most of the cases and in many cases is obligatory according to the norms and therefore does not require to be mentioned. As a result it is very difficult to find an object made of PMMA which is UVB transparent. This application refers to PMMA as being 100% pure and therefore also almost 100% translucent to UV light. If any UV filters, in particular UVA filter is wished, it will be explicitly acknowledged. For optical assembly, or optical arrangement, or light guiding means, is intended a construct comprising one or more components made of one or more materials, which have the property of collecting, guiding and diffusing light or more simply said of guiding light from a place to another place. Generally optical assembly and light guiding means have the same meaning within the application; however it may be more intuitive to use the term optical assembly describing an embodiment or a drawing, where some kind of attaching means for the fabric is included.

For waveguides or light guides, or guides, or optical element, or optical assembly/arrangement/construct, or light pipes, or light guiding means, or UVA guides or UVB guides, are intended bodies of any shape, or an assembly thereof, in optical (preferably but not necessarily physical) communication with each other, of transparent or semitransparent material with respect to the visible or the invisible light spectrum (ultra violet and infrared waves included), in particular to the UVB light, of any constant or variable cross section that have the property of conducting at least a portion of the light spectrum from a light source to a second place directly or by multiple, total or partial reflection of the light on the wall of said bodies from the front surface of the light guiding means to a second place, which may be the end of the wave guiding means or at an intermediate position between the beginning and the end of the wave guide. The wave guiding means may diffuse light along its length or may have a light output end section or is coupled to the diffusing means at the output end section. The light diffusing means may have the same shape of the wave collecting means, so that the wave guiding means can be used in both directions. Bending or scratching the light guiding means may be a method to make a glowing light guiding means and transform it in a light diffusing means. To carry out the invention, there may be a partial loss or partial exit of light waves along the wave guiding means. Wave guiding means may be rigid or flexible. In embodiments the release of the light from the light guiding means may take place at the output extremity of the light guiding means or along the light guiding means or both. In order to make the light exit the light guiding means or optical fiber that emits part of the waves may be used, for example using a guide that has imperfections on the mantel surface, wherein the surface which is close to the skin is damaged or made irregular or bended, so that the reflection angle of the waves hitting internally on the mantel of the fiber are big enough to make the waves exit the fiber. The end of a light guiding means may comprise a light or a wave diffusing element. The light guiding means may therefore be a glowing wave guiding means letting light exit during its length, generating therewith the glowing effect. According to the invention, all the above mentioned materials may be used to manufacture the wave guides. According to the embodiments of the invention a wave guiding means may be a tuft of optical fibers. The wave guiding means may have a section of full material, single or multiple hollow lumens (light pipe), or air bubbles. The wave guiding means may be made entirely of a hollow guide, entirely of a solid (in the sense of non hollow material, so that it guides the light through the solid material or materials of the guide itself, or to be a combination of hollow pipes and solid (in the sense of non hollow) guides. The light guiding means may be transparent or partially transparent for UVA and UVB light or may be transparent or semitransparent to UVB and may at least partially filter out UVA light and/or other wavelengths.

For light or waves, or waves, or rays, or radiations are intended the radiations of the solar light spectrum, from ultra violet to infrared light radiations and more particularly UVB radiations and IR radiations, in other words all the waves of the visible and the invisible light spectrum.

For light collectors, collectors, collecting means or wave collectors or light collecting means, or light concentrators, or concentrators are intended any kind of optical means, e.g. a surface, to collect the light, which may be then diverged and/or converged and/or guided to another region. The light collecting means may couple the light into the input end section of a wave guiding means, e.g. an optical fiber. A light collecting means may be a light concentrator, or it may gather light and diverge it like a diverging lens. A wave or light collecting means may be the end section of the light guiding means or the end section of the optical fiber that act as a light input surface, considering that a light guiding means has at least two end sections, one at the beginning or input and one at the end or output. The wave guiding means may therefore comprise collecting and diffusing means integral to the guiding means itself, which may have an input end section, for receiving light from the light source at the input end section, and transmit the light along itself, and at least an output end section for diffusing the light or it may emit the light along its length or both along its length and at the output end section. Any kind of light collector, or optionally light concentrator, e.g. a Fresnel lens, a convergent lens, a reflector or mirror, a deflector or a combination thereof, light collecting means with lens arrays or lens plates with multiple lenses near each other may be used to collect light to be guided by the wave guiding means. The garment assembly may have wave collecting means that comprise at least an optical element or an array of optical elements for converging, or reflecting, or deflecting waves or a combination thereof, preferably wherein the wave collecting means comprises an optical element for focusing the collected light into a wave guiding mean, or into a plurality of wave guiding mean, or into another intermediate portion, e.g. air or solid material, of the optical assembly. Light collecting means may be made of either a hollow optical element, or entirely of a solid optical element (in the sense of non hollow material), so that it guides the light through the solid material or the solid materials of the optical element, or portion of the optical assembly, itself. Light collecting means may alternatively be made of a combination of hollow optical elements that guide the light by reflection through the air or gas (e.g. mirrors, pipes cones, parabolic mirrors) and solid (in the sense of non hollow) guides, which on the contrary guide the light through a solid material or solid materials of the guide itself. Light collecting means may comprise all the optical components for collecting, deflecting and/or guiding the light, in other words a light collecting means may be done in such a way that it incorporates the entire optical assembly, which may extend from the external side of the garment, to the internal side of the garment in direct contact or in direct proximity with the skin. Being in direct proximity with the skin or in contact with the skin it doesn't mean that the optical assembly is effectively permanently in contact with the skin, but that it is in direct optical communication with the skin, e.g. that no other garment is placed between at least a portion of the optical assembly and the skin, so that the light extending therefrom would reach the skin when the garment is worn. The same three possibilities (hollow, solid or a combination thereof) are valid also for the optical elements composing wave guiding means and light diffusing means and the connections therebetween. The light collecting means can be fixed in a predetermined area or their position may be adjustable in order to cover the skin portion that may require a certain light therapy, or in order to irradiate different skin portions. Optical elements with different transparency properties may be used to obtain a different phototerapy on different areas. The light diffusing means may as well be permanently fixed, adjustable or just hanging and changing position with the movement of the garment or of the wearable device. The light collecting means might be positioned in the armpit, in order to kill bacteria responsible for the odor with a specific wavelength (in particular UV). The wave guiding means and the light collecting means may be made entirely of a hollow guide, entirely of a solid (in the sense of non hollow material, so that it guides the light through the solid material or materials of the guide itself, or to be a combination of hollow pipes and solid (in the sense of not hollow) guides. The light guiding means may be transparent to the total light spectrum, or transparent, or partially transparent for UVA and UVB light or it may be transparent or semitransparent to UVB and it may at least partially filter out, absorb, or reflect UVA light.

The exclusion of at least a portion of the UVA radiation has two advantages: it prevents possible armful radiations reaching the skin and at the same time it prevents the skin from tanning, so that a higher vitamin D (or more precisely pre-vitamin D) production can be achieved. Every collecting means may have one or a plurality of wave guiding means extending therefrom. Alternatively the light collecting means may be made from a plurality of collecting means, each collecting means having one light guiding means extending therefrom.

For optical coupling means is intended a detachable preferably physical connection between two light guides, to allow the continuity of the light transmission along the two connected light guides.

All suitable optical means to concentrate light such as flat reflectors, V-trough concentrators, light funnel/homogenizer, linear Fresnel reflector, parabolic dish/trough, Fresnel lenses, compound parabolic concentrator, Cassegrain optic, Wedge prism, luminescent/quantum dots can be adapted, eventually miniaturized and used in order to carry out the invention. All suitable optical means to diverge or deflect light may be also used for the light collecting means. Light collecting means and/or the light guiding means may be detached from the rest of the optical assembly, or from the garment assembly, for washing the garment assembly or for exchanging the type of collecting means or for repairing them, exchanging them with collecting means of a different size or of a different working principle, for aesthetic reasons, or for adjusting the quantity of the light collected according to the amount of light available. Alternatively another method for adjusting the total surface of the optical assemblies and therefore the radiation capacity of the garment assembly, the garment assembly may have a zip that can be opened and closed to expose or close an additional portion of the garment assembly, e.g. like the zip mechanism that is used on some suitcases to make them bigger or smaller. The collecting means may be modular, so that the size and shape of the collecting area can be adjusted by adding or subtracting collector's components. Collecting means may have a light collecting area which may be equivalent, smaller or larger than the smallest cross section of the wave guiding means, or of the optical assembly. Ideally the light collecting area of the collecting means is bigger than the area of the smallest cross section of the light guiding means, being the cross section of the light guiding means the cross section or area generated by the continuation of the external surface of the garment into the hole of the garment wherein the light guiding means pass through. This has the advantage of capturing more light than what would be possible by the smaller cross section of the light guiding means, providing additionally a larger attachment surface for the fabric. Alternatively the projection of the collecting surface on a plane perpendicular to the light guiding means is larger than the area (delimited by the external perimeter of the light guiding means) of the smallest cross section on the same plane, or on a plane parallel to said plane, of the light guiding means. Concentrators may be recycled from computer or television screens or from lightening means or other devices, which may show a suitable multilayered structure to diffuse and/or concentrate the light. Such multilayered structure may comprise Fresnel lenses or other optical arrangements to diffuse or concentrate light. The layers may be attached together or may slide with respect to each other in order to change the amount of light which is transmitted or in order to stop the light transmission.

A light collecting means may be positioned in the pocket or in the hood of a jacket or sweater; the hood or the pocket may be opened and closed, resulting in the opening and closure of the light collecting means through a hinge. Such a collecting means may for example have a rigid parabolic mirror, with closed or open cavity. The parabolic mirror may be made of two parabolic mirrors folding together, which, when opened, reflect the entering light into the wave guiding means. Alternatively the collecting means may have only one side or the parabolic mirror, with the wave guiding means on the other side instead of in the middle of the two mirrors. The parabolic mirror may have a circular or a linear cross section. Parabolic mirrors with a circular cross section have a tulip like shape, while parabolic mirrors with linear cross section are made of two opposite curved walls and are therefore U-shaped channels.

Wave or light diffusing elements or diffusing means (or diffusers) are means that diffuses or scatters light in some manner to transmit the collected light with the same concentration, or less concentration than the one that is given as an input to the diffusing element, or alternatively at least less concentrated than the highest light concentration reached within the optical assembly at the same moment of time. In particular a diffusing element may be a light guiding means diffusing light only at the end section, or may be a glowing light guiding means, or a wave guiding means that, thanks to imperfections, additives, or sharp curves, releases light along its length, a cap for the end of a light guiding means having a diverging optic or any other suitable optical element. The light diffusing means may be the same as the light collecting mean, in the sense that the same optical element can be used as a light concentrator or a light diffusing means, depending on the direction the light passes through it. Diffusing means may be recycled from computer or television screens or lightening means or other devices, which may show a multilayered structure to diffuse the light. Such multilayered structure may comprise Fresnel lenses or other optical arrangements to diffuse or concentrate light. The layers may be attached together or may slide with respect to each other in order to change the amount of light which is transmitted or to stop the light transmission. The term diffusung may have the general meaning of irradiating or emitting. In particular diffusing light from something may mean that the continuation of the light rays passing through (the diffusing means) may be diverging, converging, parallel, or a mixture thereof, or generally in all directions at the same time. The diffusing means may be hanging or may have attaching means to be attached to a garment or to the skin. The attaching means may be placed between light collecting and light diffusing means and may have the general shape of a channel (with constant or variable cross section along its length and along its width and with straight or undulated longitudinal axis or line passing through the barycenter of its cross section). The entire optical arrangement can be made of the same or different materials and could be manufactured by fusion, injection molding, blow molding, overmolding of different components, overmolding with a in mold fabric, extrusion, hot forming, stamping, 3D printing or by any other suitable manufacturing method. The optical arrangement may be injection molded, ultrasonic molded or fused (or heated) and formed directly on the fabric, or may be first manufactured and at a later stage embedded to the fabric.

Light diffusing means may be a combination of hollow optical elements that guide the light by reflection through the air (e.g. mirrors, pipes cones, parabolic mirrors) and/or solid (in the sense of non hollow) guides, which on the contrary guide the light through a solid material or materials of the guide itself and or optical elements that reflect the light, preferably the UVB radiations. Any surface, preferably except the collecting surface of the optical assembly may be a light diffusing means. A single optical element may be an optical assembly itself, by incorporating a light collector, a light guiding means and a light diffusing means in the same piece. In this case the parts of the optical assembly, which are between the collecting surface and the diffusing surface, may be considered the light guiding means.

Preferably sunlight may be the light source collected by the collecting means. The garment assembly may comprise a photovoltaic module to power a module to control the intensity and/or the quantity of the radiation over time and emit an alarm signal when the daily radiation limit is reached. A PV or CPV module may be on the garment assembly or be located remotely.

Alternatively to the garment assembly described herewith a garment entirely or at least partially made with UV or at least UVB transparent fabric, which may be preferably at least partially opaque to visible light, so that the human eye cannot properly see through the fabric, may be manufactured to solve the problem described above. Said fabric may be manufactured with very thin filaments. Such a garment may be also suitable to be worn under the garment assembly described herewith.

BRIEF DESCRIPTION OF THE DRAWING

The present disclosure and the following detailed description of certain embodiments thereof may be understood by reference to the following figures:

FIG. 17 shows, in front view (FV) (FIG. 16) and lateral view (LV) (FIG. 17), a garment assembly, which may be an alternative of the example of FIG. 15, which is worn partially on top of the external garment and partially under the undergarment.

FIG. 18 shows an embodiment of the garment assembly (2) which may have the features shown in FIG. 1-10, wherein the second part (12") may be an extension of the first portion (12"), said second portion being foldable (according to the folding curve (B)) from the external side (24) to the internal side (23) of the garment assembly (2) through an opening of the garment assembly (e.g. through the neck hole), underneath all garments that may be worn under the garment assembly (2), so that the light diffusing means (3) of the second portion (12"), are in direct proximity with the skin (9) without other garments in between, facing therefore the internal side (23) of the garment assembly.

FIGS. 20-32 and 34-37 show the cross section A-A of several embodiments of the optical assembly or of a portion thereof, of FIG. 1-19, comprising various attachment means to attach it to the garment.

FIG. 23A to 23E shows the cross section A-A of several embodiments of the optical assembly, or a portion thereof, before and after being formed.

FIG. 23F shows protrusions that may be manufactured on the back (103) of the head portion or the shoulder (107) of the flange, or on both sides: 103 and 107.

FIG. 23G shows a generally round notch on the flange portion.

FIG. 24-27 shows the cross section A-A of several embodiments of the optical assembly (100), or a portion thereof, wherein the optical assembly is made by two components, which are attached to each other by jamming, screwing, or by friction or fusion, wherein the garment is clamped between said two components and wherein the portion, rigid or elastomeric, clamping the fabric in the internal side (23) may be a washer, an o-ring, c-clip, or a nut to the optical assembly, or a portion thereof and wherein the washer may be made of several components, e.g. two half rings. The central internal concave surface of the dome may have a protrusion (130) on the internal side (23) to additionally deflect and/or diffuse the light, entering in the direction of the axis (X) of the optical assembly, in radial direction and/or to create an optical distortion, making the interior side of the garment assembly less visible from the external side (24).

FIG. 28-32 show the cross section, A-A of several embodiments of the optical assembly (100), or a portion thereof, wherein the optical assembly is attached to the garment with an eyelet, an eyelet with a grommet or an eyelet assembly which may comprise a prong ring fastener.

FIG. 33A to 33C and FIG. 38A to 38F show the result of an optical simulation on the cross section A-A of an embodiment of the optical assembly, or a portion thereof, wherein the incoming light radiations are parallel to each other. In FIG. 33A to 33C the simulation is performed with the light having three different inclinations, in FIG. 38A-38F the incoming light is perpendicular to the plane passing through the channel (101), which defines the neck portion (105).

FIG. 39 show the result of an optical simulation on the cross section A-A of an embodiment of the optical assembly (100), or a portion thereof, reduced to the geometry of a negative lens, wherein the incoming light is a point light source, or a diverging light source, which may be the end portion of a light guiding means (8), or the head (104) of the optical assembly (100).

FIG. 40 shows a graphical representation of the relationship between the diffused light density per unit of area (113) measured on the plane passing through the end face of the optical assembly (100), facing the internal side (23) of the garment assembly, and the ratio D/hd (112) of the diameter (or dimension of the neck portion) D of the hole, formed by the optical assembly, in the garment and the height of the dome (hd) of the head of the optical assembly from the base (103) of the head (104) to the garment's external surface.

BEST MODE FOR CARRYING OUT THE INVENTION

Figure 1:
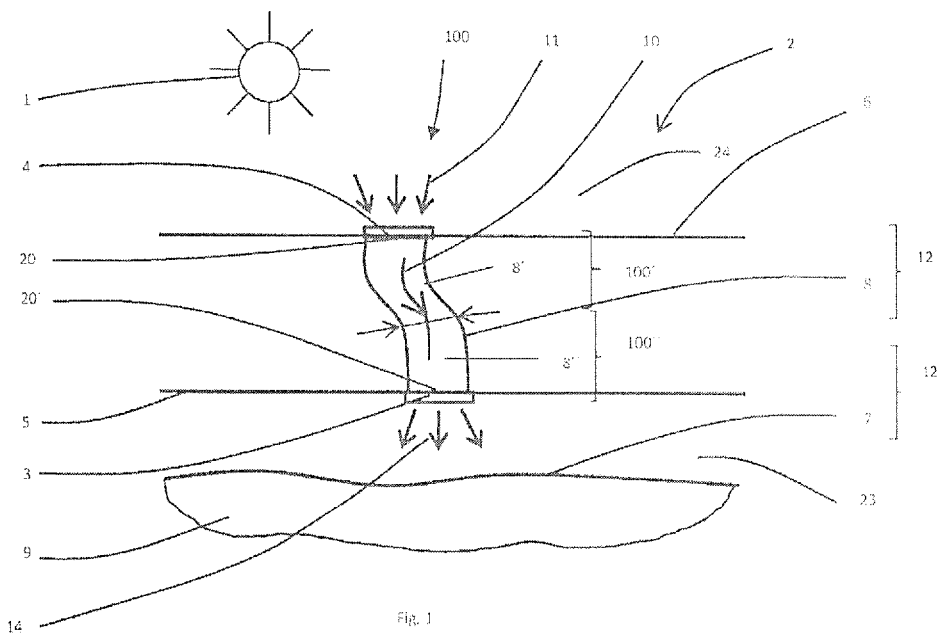
FIG. 1 depicts a cross section of the wearable device, or preferably the of garment assembly (2), with the optical arrangement (100).

The present invention relates to a garment assembly (2), with an optical arrangement (100) for collecting light (11) from the ambient and guide it to the internal side of the garment assembly, preferably to the skin's surface (7), which is covered by said garment or by another garment, thus guiding light from the external side (24) to the internal side (23) of said garment assembly.

The garment assembly, may include a light guiding means (8) suitable to guide the light from the external side (24) of the garment to the internal side (23) of said garment, or the internal side of another garment, which may be worn under a portion of the garment assembly (2). The light guiding means (8) may comprise a light collecting means (4) and a light diffusing means (3), which may be integral with the guiding means (8), or may be attached thereto. The light collecting means may be the flat or curved end portion (4) of the light guiding means (8), or of a optic fiber, which is exposed to the light, or may have any other special shape to facilitate the gathering of the light, preferably being a light concentrator, or a light diffuser, or both of them, which may have a constant or a variable cross section. The end section, or surface, of the light guiding means and the light guiding means itself may not extend through the external side of the garment assembly, so that only the light collecting means (4), or the light collecting surface (4) may face the external side of the garment assembly and the entire light guiding means may be covered by the garment assembly. The light guiding means (8) and the light collecting means may be both covered by a protective layer on the outside surface of the garment assembly, while still being able to collect at least a portion of the desired light wavelength. Said protective layer (16) on the outside of the garment assembly may be rigid or flexible and may be suitable to filter out, absorb or reflect a certain light wavelength, preferably at least a portion of the UVA wavelength. The portion of the light guiding means facing the skin or in contact with the skin, or in proximity to the skin, may be a glowing light guiding means (8), diffusing light along its length, or may emit light only at its end section or both. The light guiding means (8) may additionally be capped on the internal side (23) of the garment assembly with a diffusing means or may have several diffusing portions (3) or diffusing means (3) along its length. The internal surface (5) of the garment assembly, which is in contact or potentially in contact with the skin, may be the optical assembly itself with the diffusing means, or a portion thereof, or a comfort layer at least partially containing the optical assembly or the diffusing means.

Alternatively both a comfort layer and the diffusing means may be in contact or potentially in contact with the skin. Said comfort layer, e.g. a cloth layer, on the inside of the garment assembly may be suitable to filter out, reflect, or absorb a certain light wavelength. A wavelength filter may be placed in any portion of the optical arrangement (100). A plurality of wave guiding means and diffusing elements in combination with one or a plurality of collecting means may comprised within the garment assembly. The garment assembly with the optical arrangement may be a single piece, or an assembly of two or more interconnected pieces, wherein a first piece (12') may be an over garment, or a light collecting piece, e.g. a jacket, or a coat, or a collecting means alone, that may have the light collecting means (4) and the second piece (12"), which may be over garment (e.g. trousers), or an undergarment, which may have the diffusing means (3), being therefore the light diffusing garment (12"). The light collecting piece (12') may have no fabric, but only the light collecting means (4). A first garment (12'), or light collecting garment, may have optical coupling means (18) to be detachably connected with a light diffusing or light diffusing garment (12"), which may be itself a light collecting garment. The light collecting piece (12'), or garment, may have none, one or multiple detachable optical coupling means. The interconnected parts (12', 12") may be detachably optically and/or physically attached to each other. The light guiding means (8) may extend between the garment's external surface (6) and the garment's internal surface (5) and enter the internal side (23) of the garment assembly (2) only in the locations, where light needs to be diffused, or it may extend entirely on the internal side (23). In the case of the detachably optically interconnected garments the first light collecting part, may have a partially exposed optical arrangement, meaning that in addition to the light collecting means, light guiding means and optical attaching means and optical attaching means (18) may be partially on the external side of the garment assembly.

FIG. 1-10, 15-21, 23B, 24-32, 34-37 show a garment assembly (2), (or a portion thereof) having an external surface (6), delimiting an external side (24), and an internal surface (5), delimiting an internal side (23), said garment assembly (2) comprising at least a garment, and at least a light guiding means (8) extending from the external surface (6) to the internal surface (5), to put the said surfaces in optical communication with each other, and further comprising:

a first part (12') comprising the external surface (6), a first light guiding means portion (8') having at least a light collecting means (4) facing the external side (24) of the garment assembly (2) and a second part (12") comprising an internal surface (5), a second light guiding means portion (8") having at least a light diffusing means (3) facing the internal side (23) of the garment assembly (2).

In said figures a light guiding means (8) may be placed between an external surface (6), facing an external side (24), and an internal surface (5), facing an internal side (23), of the garment assembly (2), so that a portion (11) the ambient light (1) can be guided from the external side (24) to the internal side (23) of the garment assembly (2) so that when the internal surface (5) of the garment assembly (2) is in direct contact with the skin, or close to the skin, the guided light (14), that leaves the optical assembly, reaches the skin (7) of the user (9) wearing the garment assembly (2). The quantity and the wavelength of the light (14) might be different than the collected portion of light (11), because the collected light (11) may be, at least partially, filtered, absorbed, reflected or lost (e.g. transformed in heat or other energy forms, optionally through a photovoltaic module) along the guide. The optical arrangement (100) of the garment assembly (2) may comprise light collecting means (4), or collecting surfaces (4), which are directly or indirectly facing the light source (1) and are placed on the external surface (6) the garment assembly (2), facing the external side (24). The light collecting means (4) may be with the light guiding means and may be made by a composition of multiple wave guiding means held together, e.g. a tuft of wave guiding means, preferably optical fibers. The input end section of the light guiding means (8), which may correspond to the light collecting surface (4) is the one exposed to the light on the external side (24) of the garment assembly (2) and is additionally defined by the direction (10) of the light into the light guiding means, which goes from the external surface, or external side (24) to the internal surface or internal side (23) of the garment assembly (2), or of the optical assembly (100). Said light collecting means (4) may be permanently or non-permanently coupled to the light guiding means (8) and may comprise light concentration and/or light deflection optical means. Said light collecting means (4) may be optical instruments made of one or different materials including air or gas. There might be one or a plurality of light collecting means (4) and each of them might be connected to one or a plurality of wave guiding means (8). In the case said light collecting means (4) being permanently attached to, or integral with the light guiding means, they might be the end cross section of the light guiding means itself, which may have a variable cross section, to adapt forming a light converging and or diverging optic, or a constant cross section. Additionally the light guide and therefore its cross section may be full, or partially empty, so that the light propagates in the air. The same may be valid also for the collecting means and for the diffusing means and therefore for the entire optical assembly (100). The wave guiding means may have a single or multiple hollow lumens, or air bubbles and it may be closed or open on both sides, or it may be closed on one end and open on the other end. Optionally the light guiding means is air tight and does not allow air communication, through itself, between the external surface and the internal surface of the garment assembly, meaning that the optical guiding means (8) is airtight between the light collecting means (4) and the light diffusing means (3). The fabric of the garment assembly, may not be airtight, however the optical element is totally or almost totally airtight. The material of the light guiding means (8) might have impurities, or additives, or coatings, or films for reflecting, absorbing, deflecting or filtering light, or agents with different optical properties, including reflecting and filtering properties, e.g. titanium dioxide as film, coating or additive. The entire optical arrangement can be made of the same or different materials, which may be attached or mixed together, e.g. mixed before injection molding. The optical arrangement (100) of the garment assembly (2) may comprise a light diffusing means (3), or light diffusing surface (3), or a plurality thereof, positioned along the light guiding means or at the extremities thereof, facing the internal side (23), of the light guiding means (8). The light diffusing means (3) may be the output section or area of the light guiding means. There might be one or a plurality of light diffusing means (3) and each of them might be connected to one or a plurality of wave guiding means (8). The light collecting means and/or the light diffusing means may be spatially arranged about said garment assembly (2) in at least one of an array pattern, a vertically aligned array pattern, a horizontally aligned array pattern, a diagonally aligned array pattern, a predetermined pattern representative of a phrase, a predetermined pattern representative of an image, a zigzag pattern, a spiral pattern, in ring pattern and a random pattern. Light collecting means (4) may be optical instruments made of one or different components and/or materials including air. The internal surface (5) of the garment assembly may be in contact with the skin or distant from the skin, still ensuring a portion of light or light waves to reach the skin (7).

The optical assembly or at least a portion thereof may be manufactured separately from the garment and attached to the garment in a second step, alternatively it may be partially manufactured and then formed or fused on the garment, or alternatively it may be entirely or partially injection molded on the garment with a fabric in mold manufacturing process.

Figure 2:
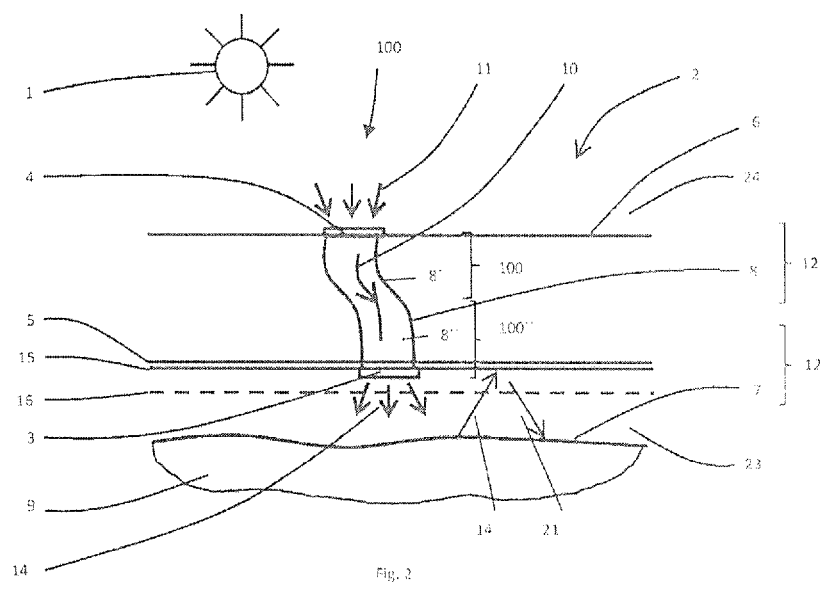
FIG. 2 depicts cross section of the garment assembly (2), with the optical arrangement (100), additionally provided with a comfort layer (16) and a reflective layer (15).

Referring to FIG. 2 in an embodiment of the garment assembly (2) of FIG. 1, 3-10, 15-21, 23B, 24-32, 34-37, a comfort layer (16) may be placed on the internal surface (5) on the internal side (23) of the garment assembly (2). Said comfort layer (16) may contain the wave guiding means and the light diffusing means and may provide comfort to the user of the garment assembly. When the garment assembly (2) is worn, the comfort layer is positioned at least partially between the skin and the optical arrangements. In embodiments the internal surface (5), or side (23) may comprise the reflective material (15) for reflecting the light (14) which may be diffused, or reflected against the internal surface (5) of the garment assembly (2) and therefore away from the skin (7). The layer of reflective material (15) may not cover the light diffusing means (3) in order not to impede the light from reaching the skin. The reflective layer reflects the light (14), which is not directed toward the skin, redirecting it in the direction (21) of the skin. The layer of reflective material (15) may be discontinued. The reflective material (15) may be implemented into the garment assembly (2) with or without the comfort material (16). There may be both, reflective material (15) and comfort material (16), one of them or none of them. The reflective material may be synergistically also keeping the inside of the garment assembly warm and therefore it may also reflect heat waves, e.g. infrared waves.

Figure 3:
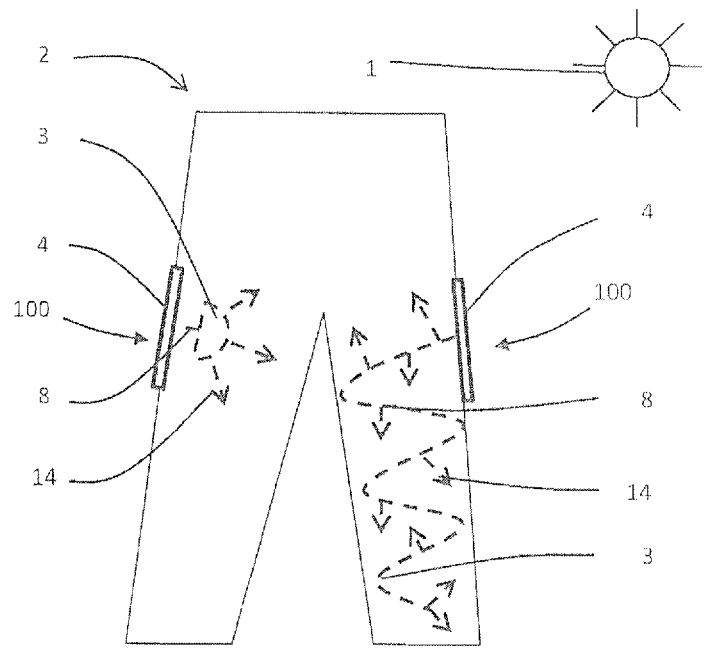
FIG. 3 depicts an illustrative embodiment of the garment assembly (2), with the optical arrangement (100), which is in this case a pair of trousers to be worn directly on the skin (9), or with a light at least semitransparent undergarment.

FIG. 3 shows an embodiment of the garment assembly (2) of FIGS. 1 and 2 and may apply to FIG. 5, 6, 10, 15-21, 23B, 24-32, 34-37. Preferably, according to the embodiments of FIG. 1-3, the garment assembly may be a pair of trousers. On the external side (24), preferably on the external surface (6) of the garment assembly light collecting means (4) may be placed. The light collecting means (4) are optically connected to the wave guiding means (8), which extend through the garment assembly and have light diffusing means (3) to release the collected light to the internal side of the garment assembly (2). The light guiding means (8) may be coupled with an optical means (3) to diffuse the light or may diffuse light along its length. A light guiding means that diffuse light along its length is commonly called a glowing light guiding means (8). A glowing light guiding means (8) may as well have optical means at its end section to diffuse the remaining light, or may be capped with a mirror to avoid a too concentrated release of light. The light guiding means may be short or long, it may release light in the immediate region of the collecting means or remotely. The trousers or FIG. 3 may have a comfort layer and a reflective layer as shown in FIG. 2. The collecting means may have different shape and height and might be adapted to become ornamental and/or objects of the garment assembly. Optical assemblies which are shown in FIG. 21-39 are suitable to be combined at least with the embodiments of FIGS. 3, 4, 7 and 10.

Figure 4:
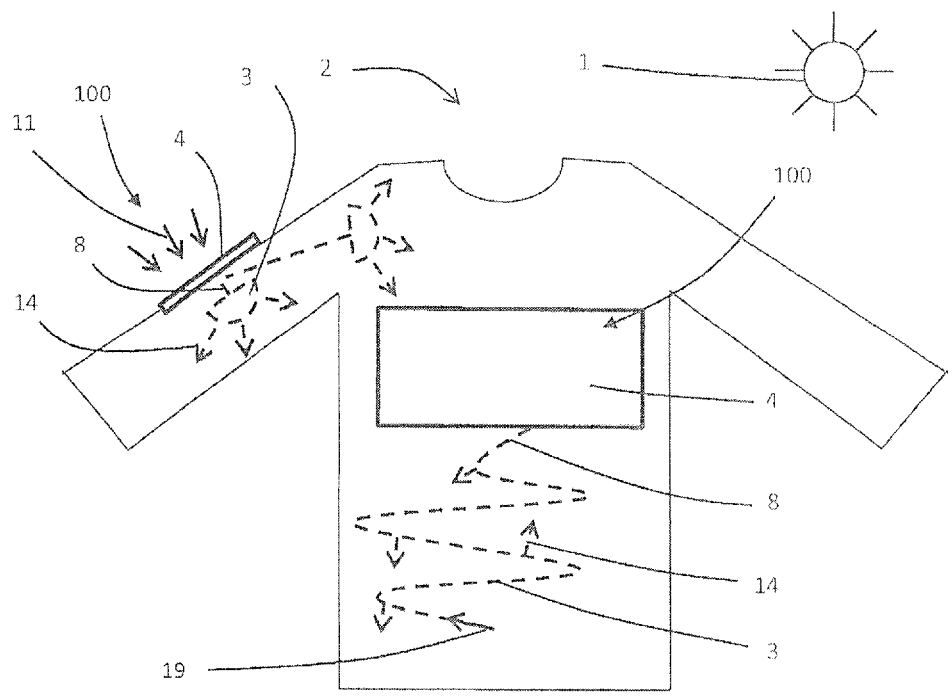
FIG. 4 depicts an illustrative embodiment of the garment assembly (2), with the optical arrangement (100), which is in this case a top garment, preferably sportswear, like a pullover, a sweat shirt, a jacket, a tunic or a coat or a garment with t-shirt, shirt and pullover bonded together, preferably to be worn directly on the skin, or with a light at least semitransparent undergarment. &p
Figure 5:
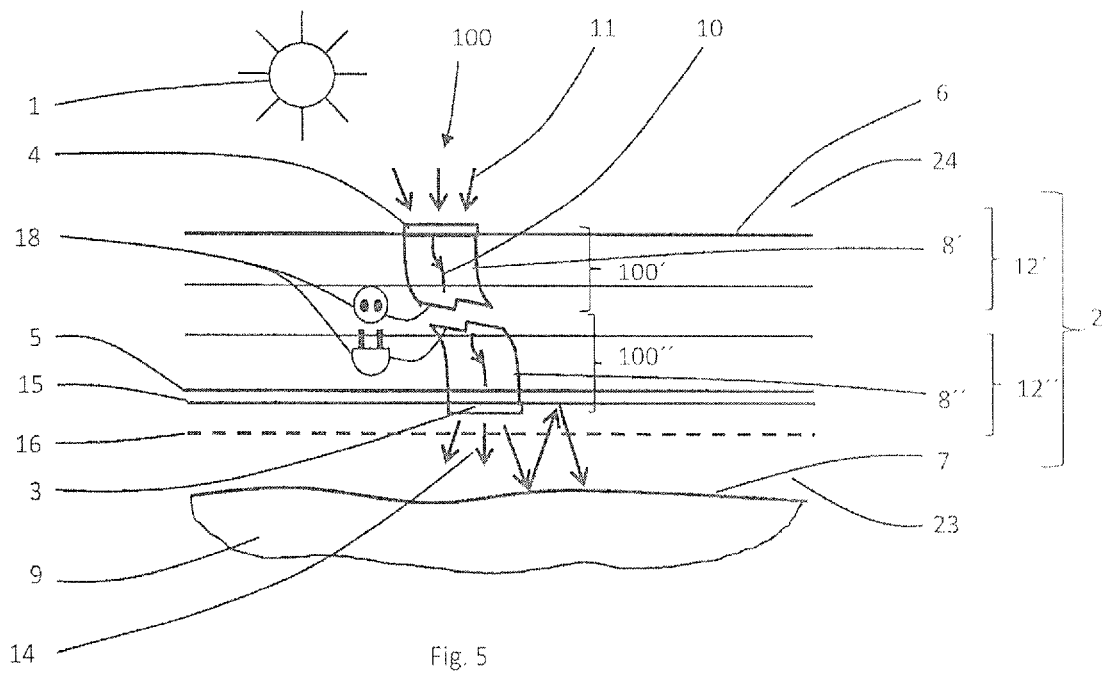
FIG. 5 depicts a cross section of the garment assembly (2), with the optical arrangement (100), additionally provided with optical coupling means (18) to detachably join the light receiving portion (100'), or first part, and the light diffusing portion (100"), or second part, of the optical arrangement, wherein the first part (100') of the optical assembly (100) belongs to a first part (12') of the garment assembly and the second part (100") of the optical assembly (100) belongs to a second part (12") of the garment assembly (2).

FIG. 4 shows an embodiment according to the embodiments of FIG. 1-2, where the garment assembly (2) may be a t-shirt, a shirt, a jacket or a coat or a combination thereof bonded together in a single garment. However any other piece of garment, even a cap or a scarf may be combined with the same optical assembly. The garment of the garment assembly may be a composition of different garments or a very warm garment, being a unique piece of clothing with for example a shirt and a pullover attached together, so that it looks like a two pieces clothing but in reality it is formed only from one piece, so that it may be worn directly on the skin and still look like an elegant and/or warm clothing composition. According to this embodiment as for all other embodiments, every collecting means (4) may be a single collecting means or an array of collecting means. Every single collecting means (4) or every collecting means of an array of collecting means may be the starting point of one or multiple wave guiding means (8) departing from it. Said wave guiding means may be glowing wave guiding means or wave guiding means capped with a diffusing means or simply diffusing light from their end section, or both: glowing wave guiding means capped with a diffusing means at the same time. FIG. 5 shows an embodiment which may optionally apply to the embodiments of FIG. 1-10, 15-21, 23B, 24-32, 34-37 where the light guiding means (8) and therefore the optical assembly (100) have two parts (8', 8" and 100', 100") which may be detachably coupled by optical connecting means (18). The first part (8') of the light guiding means (8) is comprised within the first part (100') of the optical assembly (100), wherein said first part (100') of the optical assembly (100) in comprised into the first part (12') of the garment assembly (2). The second part (8") of the light guiding means (8) is comprised within the second part (100') of the optical assembly (100), which is comprised within the second part (12") of the garment assembly (2). Despite in some cases it may appear more appropriate to use optical assembly and in other cases to use light guiding means, in all embodiments, they refer actually to the same object and so do their respective first and second parts.

The optical connecting means (18) may additionally have a mechanical or a magnetic coupling system. The two components (8', 8" and 100', 100") can be made of the same shape and material, or have a different material or cross section. Alternatively the two light guiding means (8', 8"), as any other portion of the portion of the optical assembly (100) may be either coated with a reflective and/or protective layer or uncoated. Optionally only a portion of the optical assembly may be coated. For example only a portion of the first part (8') of the light guiding means (8') may be coated, or covered by a reflective or absorbing layer and the other may be, at least partially, a glowing light guiding means, so that the first part (8') of the light guiding means (8) of a first part (12') of the garment assembly (said first part comprising the first portion (100") of the optical assembly (100) and optionally at least a portion of the external surface (6) of the garment assembly (2)), guides all the light through its section and the light guiding means (8") of the second part (12") of the garment assembly (said second part comprising the first portion (100') of the optical assembly (100) and optionally at least a portion the internal surface (5) of the garment assembly (2)), or second part, diffuses light underneath the garment assembly (2), on the internal side (23) of the garment assembly (2). The internal surface (5), or the internal side (23), of the garment assembly, may be provided with a reflecting layer (15) so that the light guiding means (8") diffuses the light underneath the reflecting layer (15), between the reflecting layer and the skin (7). The first part of the garment assembly (12") and the second part of the garment assembly (12") may be on top of each other like in FIG. 8 as for example a jacket or a pullover worn on top of a singlet or a camisole. Alternatively the first part (12") may be only a light collector, in optical communication with the second part (12"), which may include a garment, or only a light diffusing means in optical communication with the first part. The first part (12"), and the second part (12"), if worn on top of each other (FIG. 7, 8) may have also multiple other garments in between and still be optically connected from the a side, a flange or a margin or from any other suitable place. The first part (12'), and the second part (12"), may be worn offset as shown in FIG. 9, therefore not completely on top of each other, as for example a jacket or a pullover and a pair of trousers and still be optically connected from a side, a flange or a margin or from any other suitable place. For example a flange with the light guiding means (8') and an optical attachment (18) may extend from the bottom of the jacket or pullover and optically detachably connect with a flange extending from the top of the pair of trousers containing the light guiding means (8") and a suitable optical attachment (18). The first part (12'), may have several optical attachments (18) and be coupled with more than one second part (12").

Figure 6:
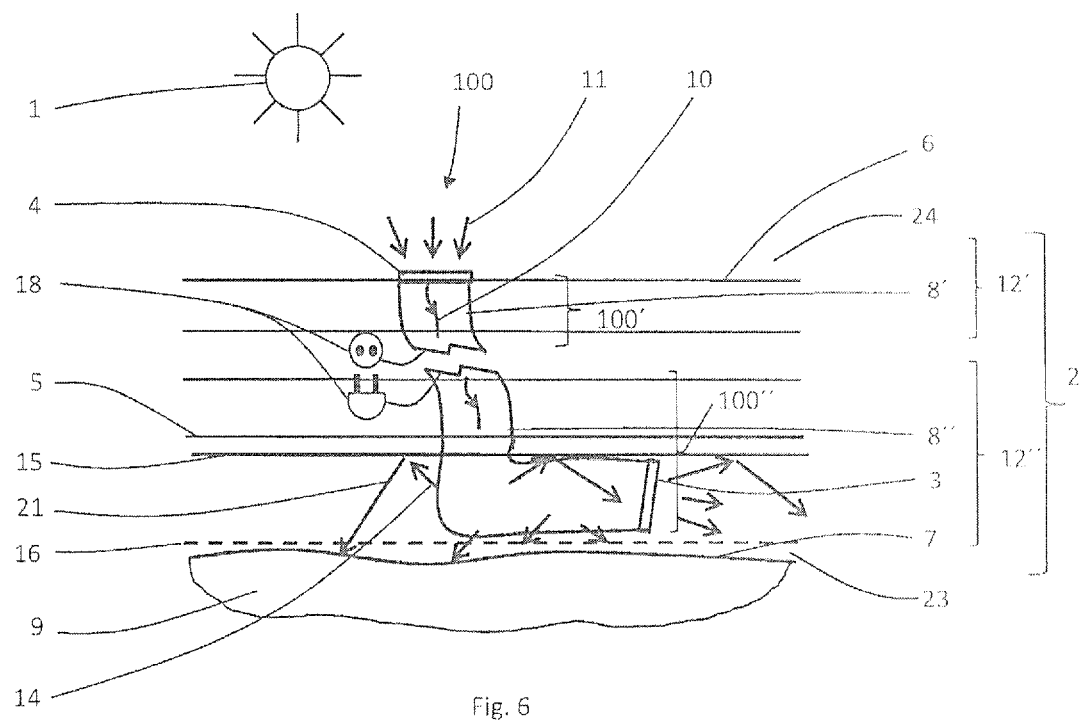
FIG. 6 depicts the garment assembly (2) of FIG. 5 additionally provided with a light diffusing extension, which may be a glowing light guiding means.

FIG. 6 shows an example, which may apply also to the other embodiments of FIGS. 1, 2 and 5, where the second part (8") of the light guiding means (8) extend beyond the internal surface (5) on the internal side (23) and beyond the reflective layer (15), if the latest is available. The second part of the light guiding means (8"), or second light guiding means (8") may be a glowing light guiding means; it may be capped with a mirror or with a soft light diffuser. Alternatively the light guiding means may diffuse the light only at its end section with or without a diffusing means (3). The second part of the light guiding means (8") may be spatially arranged about said second part or second garment (12") in at least one of an array pattern, a vertically aligned array pattern, a horizontally aligned array pattern, a diagonally aligned array pattern, a predetermined pattern representative of a phrase, a predetermined pattern representative of an image, a zigzag pattern, a spiral pattern, in ring pattern and a random pattern.

Figure 7:
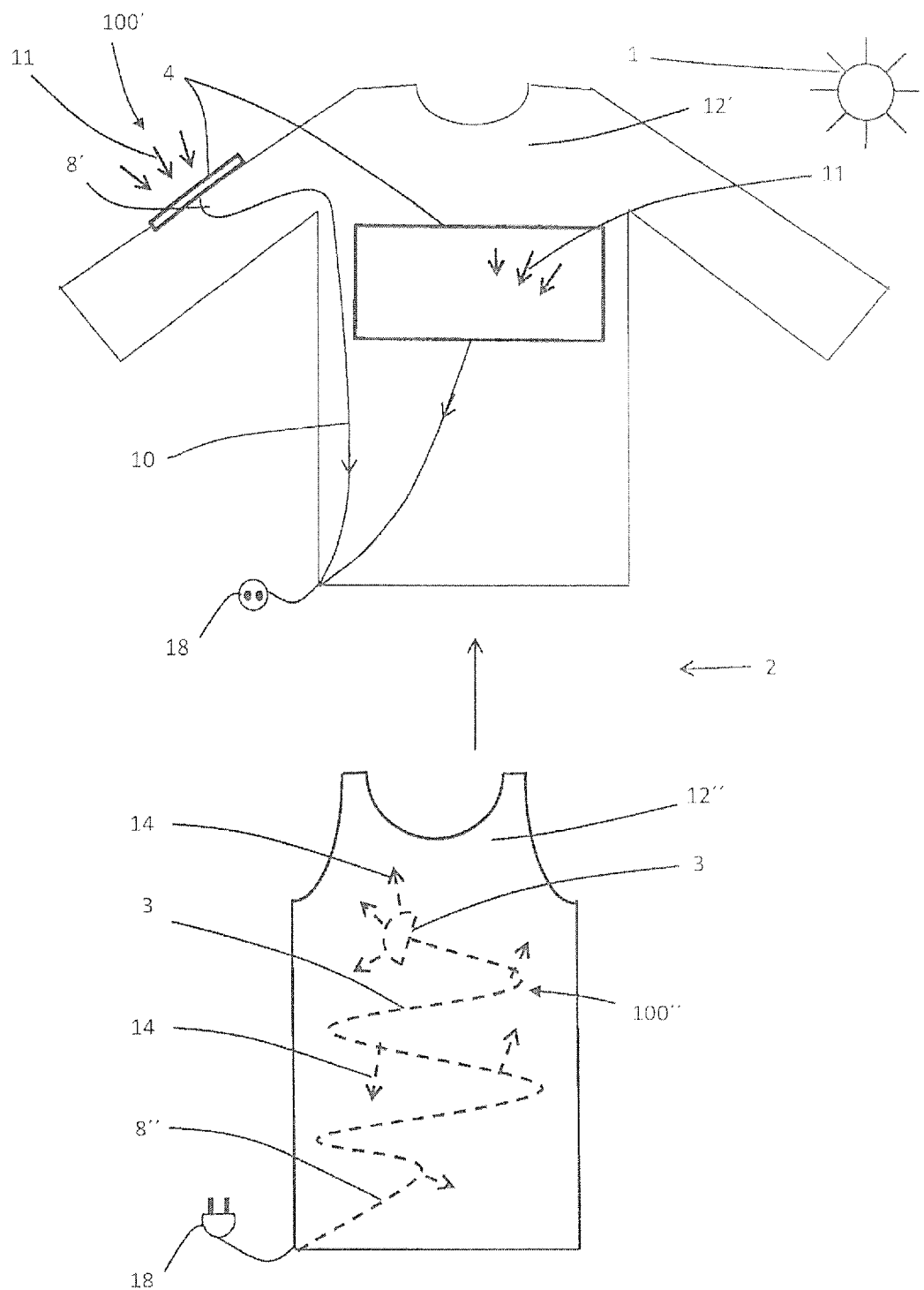
FIG. 7-8 depict an illustrative embodiment of the garment assembly (2) of FIGS. 5 and 6, made of the combination of a first part (12"), or preferably an over garment and a second part (12"), or preferably an undergarment with the detachable optical arrangement.
Figure 8:
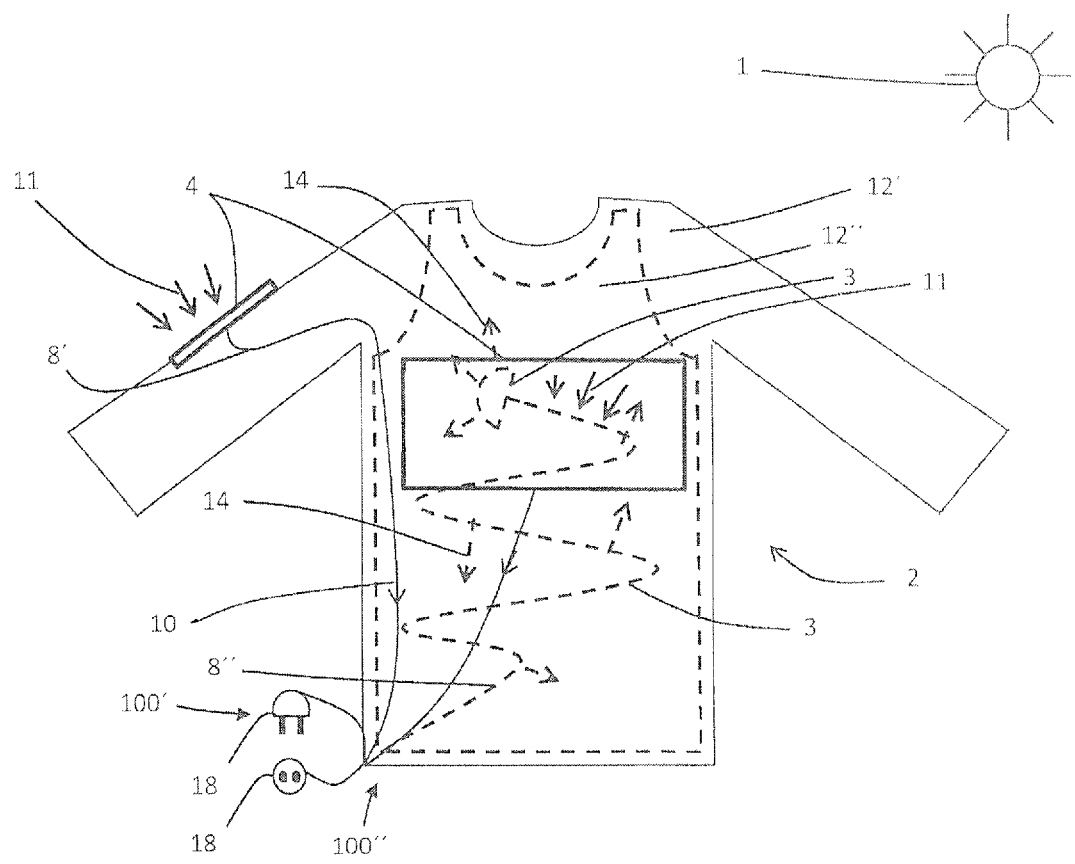
Figure 9:
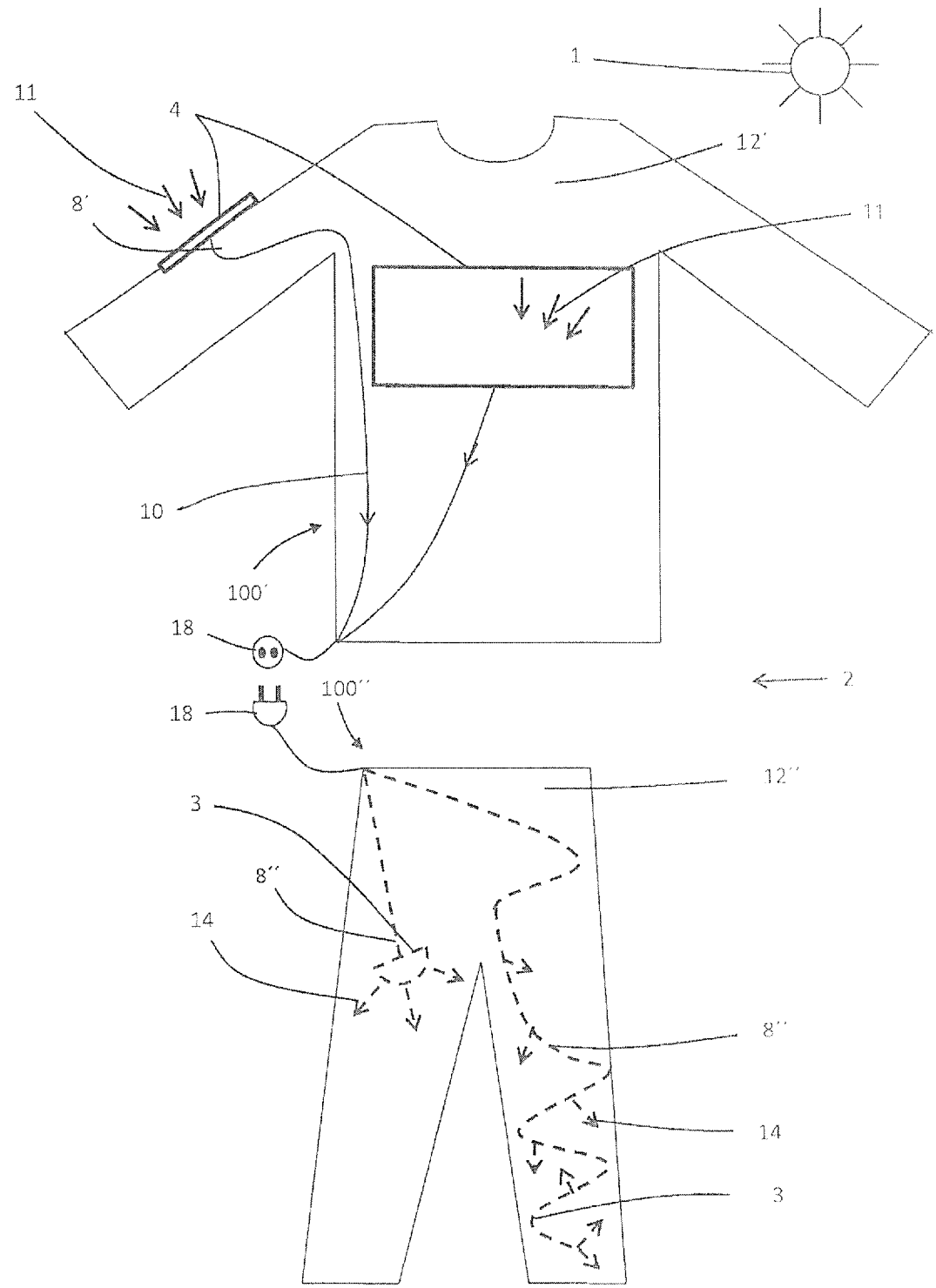
FIG. 9 depicts an illustrative embodiment of the garment assembly (2) of FIGS. 5 and 6, wherein first (12') and second (12") parts are both an overgarment.

FIGS. 7, 8 and 9 show an example of the embodiment of FIG. 6, where the first part (12') of the garment assembly (2) is a jacket or a pullover or a coat and the second garment (12"), or second part, is a singlet or a camisole, which is worn underneath and is detachably connected by optical coupling means (18). According to this embodiment many other garments may be worn under the first part (12') or optionally between the first (12') and the second (12") part, so that the first part, e.g. a jacket or a coat, can be removed and therefore detached from the second part, e.g. an undergarment (with respect to the outer garment, which may be a pullover, if the first part is a jacket), or a pair of trousers, when the user enters for example a warm place.

In other words, FIGS. 7 and 8, but also following FIG. 9, 10 and FIG. 17-18 shows a garment assembly (2) comprising: an internal surface (5) facing an internal side (23) of the garment assembly (2) and an external surface (6) facing an external side (24) of the garment assembly (2), and at least an optical arrangement (100) (also light guiding means (8)), comprising: at least a wave collecting means (4) on the external surface (6) for collecting light waves (11) hitting the external surface (6) from the external side (24) of the garment assembly, at least a wave diffusing means (3) on the internal surface (5), oriented in a inward direction with respect to the plane defined by the internal surface (5) of the garment assembly (2), wherein said wave guiding means (8), extending from the collecting means (4) to the diffusing means (3), and wherein the wave collecting means (4) have a light waves collecting area which is larger, or optionally equal or smaller, than the area of the smallest cross section of the waves guiding means (8) and wherein the waves optical arrangement is made of an UV transparent or UV semitransparent material. Optionally the garment assembly (2) may have the wave collecting means (4) or the waves guiding means (8) or both having means to be permanently or detachably fixed to the garment assembly (2), alternatively or in addition the wave guiding means may be attached to the garment by gluing or overmolding. Optionally the garment assembly (2) may comprise light filtering or absorbing means to let through only a certain wavelength, preferably only the UVB wavelength and/or comprising wave guiding means that are at least partially transparent to UVB waves and at least partially opaque to UVA waves. Optionally the garment assembly (2) may have, between the wave diffusing means (3) and the wave collecting means (4), at least a partially reflective layer (15), so that the wave diffusing means (3), or the diffusing surfaces (3), are placed between the skin and the reflective garment, in order to reflect the diffused light that is not directed in inward direction. Optionally the garment assembly (2) may have the internal surfaces (5) and the external surfaces (6) that are detachable to or from each other, so that the first part (12') and the second part (12") are adapted to be optically and preferably physically detachably joined to each other. It is therefore conceivable that the garment assembly (2) may have the waves guiding means connecting the wave collecting means (4) and the wave diffusing means (3) which are made of two portions (8' and 8"), detachable from each other, wherein the first portion (8') belongs to the first garment (12') and the second portion (81 belongs to the second garment (121, the first and second portions being in optical communication through detachable optical coupling means (18). Optionally the garment assembly (2) may have the first part (12') configured to be worn over another garment and the second garment (12") configured to be worn with its internal surface (5) in contact or in proximity to the skin or facing the skin. Optionally the second part (12"), or optionally the undergarment, which comprises at least the wave diffusing means (3) on the internal surface (5), said undergarment (12") extending between at least an upper opening and at least one lower opening, an orientation of said undergarment body defining an external surface (6) and an internal surface (5) and preferably at least a portion of the second portion (8") of the waves guiding means having light diffusing areas (3) or light diffusing means (3), optionally along its length and/or at its end section, preferably forming the body of the garment, and preferably being affixed to the external or to the internal surface or between the internal (5) and the external surfaces of said undergarment body (121; and wherein the light opaque first part (12') or external garment, in optical communication with the undergarment (12"), comprises a first portion (8') of waves guiding means, said first portion (8') extending from the second wave diffusing portion (8") of the undergarment, to external surface (6) of the outer garment, or first part (12'). Herewith it is disclosed the use of alight guide (8), or optical arrangement (8), on a garment comprising: an internal surface (5) facing an internal side (23) of the garment assembly and an external surface (6) facing an external side (24) of the garment assembly; for guiding at least a portion of the light waves (11) hitting the garment in a inward direction with respect to the a plane defined by the internal surface (5) of the garment. Such an assembly, having optionally detachable wave collecting means, may advantageously imply a method for mechanically adjusting the light collecting capacity and consequently the total diffused light intensity of the garment assembly by attaching or detaching a portion of the total wave collecting means, or by changing the type of the wave's collecting means.

FIG. 9 shows a garment where the first part, or first garment (12'), is a jacket or a pullover and the second part, or garment (12"), is a pair of trousers, which is detachably connected by optical coupling means (18). Legs are a large portion of the body, which is less exposed to the sun and therefore whiter, therefore ideal for the vitamin D synthesis. Trousers frequently worn directly on the skin, but they usually are less exposed to the light than a pullover. Additionally it might be beneficial to spread all the collected light over a larger surface, therefore spreading it between legs and torso with the connection of two second garments (12") or second parts, to the first garment (12'), or first part, or alternating a second garment (12"), or second part, covering the legs and a second garment (12"), or partially, covering the torso like in FIG. 8, by coupling one second part or the other second part, or optionally by coupling both second parts to the first part at the same time. The trousers comprising optical coupling means (18) in optical communication with the light collecting means (4) of the first part (12') through optical coupling means (18) may have light collecting means themselves, and deliver the collected light into the same light guiding means, or into an additional separated light guiding means (8). The first garment (12'), or first part, may also have light diffusing means, therefore sharing the collected light between the diffusing means on the internal surface of the first garment, or first part, and the diffusing means on the internal surface of the second garment (12"), or second part.

Figure 10:
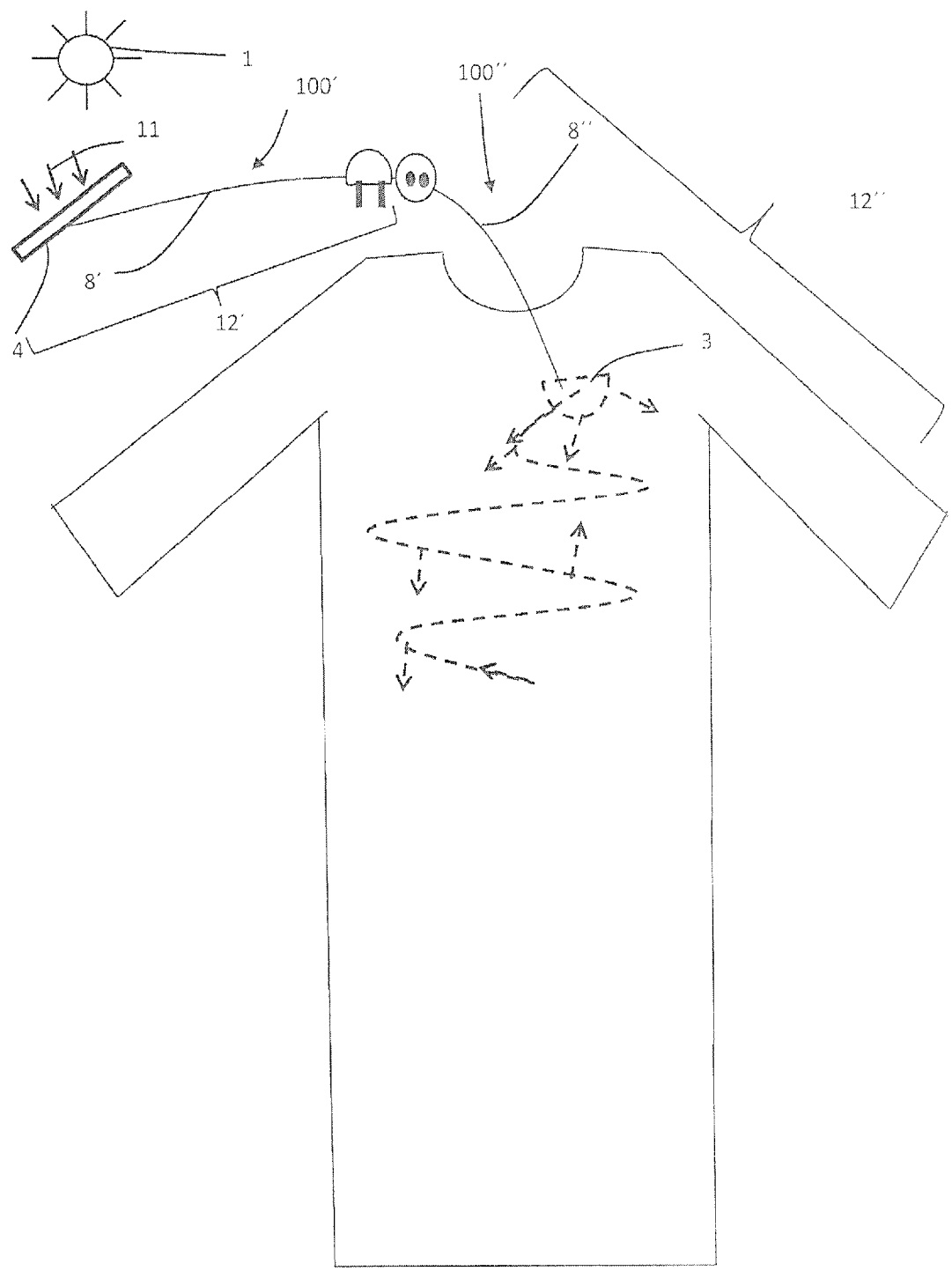
FIG. 10 shows a garment assembly (2) comprising a second part (12"), which may be a tunic, which is detachably coupled, with optical coupling means (18) to a first part (12') of the garment assembly (2), being a detachable light collecting means (4), said first part (12') may be placed outside in the sunlight, so that the collected light can be guided inside the second part (12"), when the person wearing the tunic in inside and the tunic itself is not exposed to the light.

FIG. 10 shows a long garment assembly (2), e.g. comprising a tunic, which may be an overgarment to be worn, at least for some body parts underneath it, without undergarment, or with a light undergarment, or a partially transparent undergarment, or an UVB transparent or semitransparent undergarment. Said UVB transparent or semitransparent undergarment may be integral to the tunic, e.g. being the protective layer of the light diffusing means (3). Said long garment assembly having detachable light collecting means on a first part (12'), that may be placed outside on the sunlight, in optical communication with the second part (12") through optical coupling means (18), so that the collected light can be guided inside the clothing, when the person wearing the tunic in inside and the tunic itself is not exposed to the light. This garment is for example suitable for people in warm countries that spend most of the time inside, because of the heat. The light guiding means (8) connecting the light collecting means (4) to the garment may be long enough to allow to the person wearing the garment to stay far away from the collector. There may be a plurality of people inside the room all connected to the same light collector. Alternatively a single person may connect only with a portion of the light guided from the collector, so that only the selected portion of light is guided to the skin, in some cases underneath the garment assembly. The user may select connecting a single or a plurality of wave guiding means to the second part (12') of the garment assembly. Therefore every collecting means may have one or a plurality of wave guiding means extending therefrom. Alternatively the light collecting means may be made from a plurality of collecting means, each collecting means having a light guiding means (8) extending therefrom. The light guiding means or the wave guiding means may be extendible and adjusted to the desired distance between the garment and the light collector. With the light collecting means there may be a photovoltaic element to power a unit which may have one or more sensors and a display and or a warning signal. The light powering the photovoltaic (PV) unit may come directly from the light source, or may come partially or totally from the collecting means and it may form therefore a concentrated PV module (CPV). The unit may communicate via radio, wifi, or Bluetooth with another device, so that the information about temperature, light intensity or cumulative light transmitted can be monitored with an app on a mobile device. Alternatively the unit may display said information itself. The light guiding means (8) may be transparent or partially transparent for UVA and UVB light or may be transparent or semitransparent to UVB and may at least partially filter out UVA light. The light source may also be in a room with artificial or natural UVB light and the people wearing the tunic or gown may be a patient wearing the garment assembly inside a room. The internal inside (23) of the tunic may be optically connected to the external light source. There may be a big concentrator to place outside, or be exposed to a light source outside a room or a building, with guides that go inside the room and connect to a phototerapy device or to a phototherapy garment, having the optical assembly. The hospital can also use such assembly to power phototherapy devices instead of lamps.

In the embodiments of FIGS. 1-10, and in any other embodiment, where it may be appropriate, the light guide, optionally connecting light collecting means to light diffusing means, or a portion thereof may be made of a bunch or bundle of round and thin optical fibers, or by a film ream of any suitable material, having the whished optical properties, so that it can be flexible.

Figure 11:
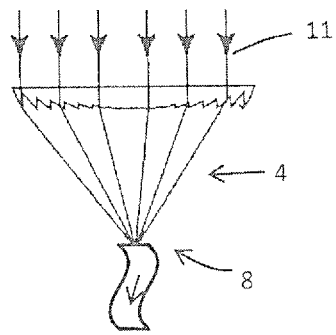
FIG. 11-14 depicts several examples of light collecting means, with converging optic, which may be suitable for concentrating the light into an optical element with a smaller cross section, or smaller capacity, than the one of the light collector, which may be incorporated into the optical systems of the garment assembly, as wave collecting means. The light collecting means of FIGS. 13 and 14 with inverted arrows (not shown) may be also a wave diffusing means.
Figure 12:
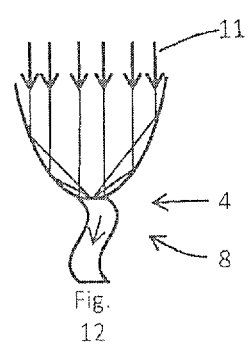
Figure 13:
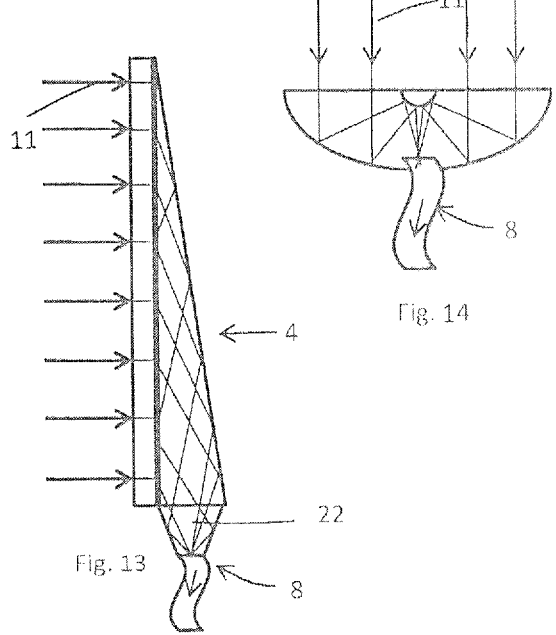
Figure 14:
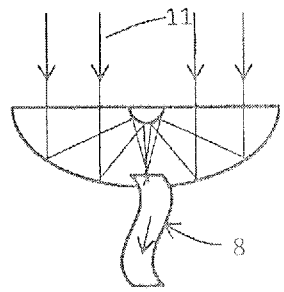

FIG. 11-14 show different optical systems suitable to be employed as light collecting means (4). FIG. 11 shows a light collecting means with a positive, or optionally a negative (not shown), Fresnel lens, wherein the light (11) converging in the focal line or in the focal point or focal area is guided into the light guiding means. The light converging towards the focal line or the focal point are guided into the light guiding means using a suitable optical component (22), within the optical assembly (100), consisting for example of mirrors and/or lenses, or deflectors, or the like, to such an extent that the light can be transported out of the focal line or focal point or area without too great divergence over the desired distance to the desired location. In FIG. 11 the incident radiation (11) is deflected via the Fresnel lens into a converging beam. Light guiding means (8) capture the light and transmit it inside themselves by total or partial reflection. For reasons of weight, size and cost, Fresnel lenses, shown in the exemplary embodiments described by FIG. 11, may be advantageous. However other optical assemblies may be used. FIG. 12 shows for example a light collecting means (4) with a Winston cone; FIG. 13 shows a planar light collecting means (4), optionally with a combination of lenses and faceted tapered shapes to deflect light from a large surface into a light guiding means (8); FIG. 14 shows a system with two parabolic mirrors (in particular a Cassegrain optic may be used) with a parabolic primary mirror and a hyperbolic secondary mirror to concentrate incident normal incident light. Any other suitable optical system can be used to carry out the invention, e.g. a convex, plano-convex, bi-convex, positive or negative meniscus, concave, biconcave or plano-concave lens. A deflector like the faceted tapering deflector (22) in FIG. 13 can be used in any light collecting means (4) to help focus the light into the light guiding means. The deflector (22) might also be a Winston cone or a mirror of a different shape. However any other suitable optical structure (e.g. sawtooth pattens, reflective coatings) may be used to make the light to converge, diverge or collimate, or to change the direction of the light provided by the collecting means. Materials with different refractive index may be used for the light guiding means. The light guiding means and/or the light collecting means itself may be made of a composition of several collecting means of the same type or of different types arranged in an array, which may be in parallel or in series. The cross section area taken in a direction transversal to the preferably rotational or central (preferably extending through the garment perpendicular to the external surface) axis (X) of the light guiding means, and of the collecting means (4), or the light collecting surface (4), may be in any possible relationship, meaning that the light waves collecting area may be multiple times larger than the area of the smallest cross section of the waves guiding means between the surface of the wave collecting means and the wave diffusing means. Preferably the cross section of the wave guiding means may not be too small to generate overheating along the optical arrangement and into the garment assembly (2). As shown in FIGS. 11-15, 17, 19-32 and 34-38 and preferably possibly also for FIG. 1-10 the wave collecting means (4) may have a wave collecting surface, which is larger than the area (including solid and empty zones) of the smallest cross section taken perpendicularly to the axis (X) of the waves guiding means (8), delimited by the dimension (D), or by the perimeter of the neck portion (105), generated by the continuation of the external surface of the garment into the hole of the garment wherein the light guiding means pass through. It may be conceivable that the wave collecting means have a surface area which is larger than the area that the hole of the garment has when the optical assembly is inserted. This allows embedding the optical assembly in the garment, simultaneously providing an attachment for the fabric, to reduce the weight of the optical assembly with respect to alternative attachment solutions and to potentially guide more light through the hole of the fabric than the light that would have passed through the same hole without the optical assembly. The ratio between the area of the collecting surface and the area of the neck cross section (including full and empty areas), or the ratio between the area of the collecting surface and the hole that the garment has when the optical assembly is inserted, may vary based on the kind of optical principle used for the wave collecting means (4) and may be always higher than 1 and even a multiple than 1, being the area of the collecting surface bigger that the area of the neck cross section. Preferably said ratio is between 1,1 and 4, more preferably between 2 and 3. Ideally the light that hits, from any direction, at least 50%, or 70%; or better 85%, or even better 90% of the collecting area, or external surface, of the wave collecting means (4) may effectively be guided through the garment assembly. This can be for example, be evaluated based on the examples of FIG. 33A-33C, FIG. 38A-38G and FIG. 39 showing the optics simulation. Every kind of light guiding means and therefore of light collecting means may be adapted, miniaturized, or redesigned to be so small to be used as a button of different shapes, being preferably a functional, or a decorative part of the garment. The light collecting means (4) may alternatively be not attached to the garment and be placed remotely, meaning in a different place, separated from the user, while still being permanently or non permanently optically and/or physically connected to the garment assembly (2), while the person wearing the device, or garment, is not exposed to the light source. A collecting means may have one or a plurality of wave guiding means extending therefrom, in different words, the light guiding means may comprise a light collecting surface, a plurality of optical fibers and one or a plurality of diffusing means. Alternatively the light collecting means may be made from a plurality of collecting means, each collecting means having one light guiding means extending therefrom.

Figure 15:
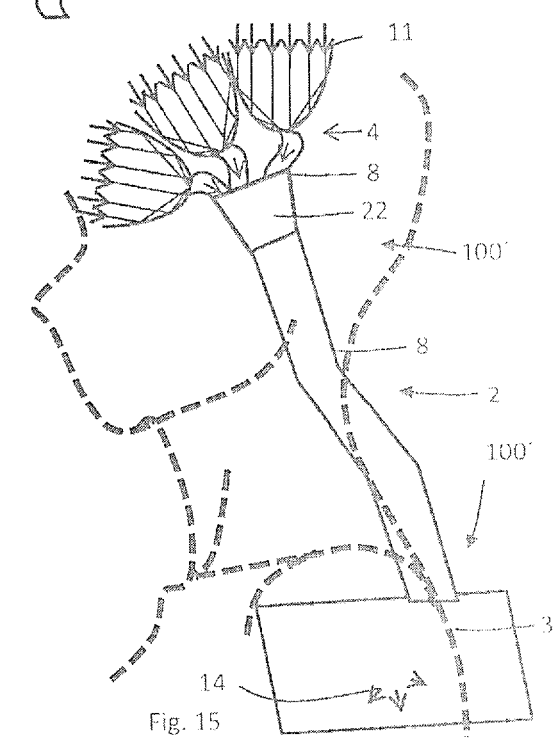
FIG. 15 depicts an illustrative embodiment of a decorative garment assembly (2) to be placed on the head of a person, or on the external surface of a garment, said garment assembly (2) having tulip like light collecting means (4) preferably optically connected with a diffusing means (3) to be inserted inside the clothes from the neck hole for irradiating the for example back of a person, which is covered by other garments.

FIG. 15 shows an additional example of the embodiments of FIGS. 1-6 and depicts a decorative wearable device, or garment assembly (2) for arranging the hairs, decorating a hat or a scarf or for attaching to the external of another garment different than a hat or a scarf, said garment assembly may have light collecting means with a tulip like, or a button like shape, optically connected with a diffusing means to be inserted inside the clothes, for example from the neck, for irradiating the for example the back of a person. The optical arrangement, or light guiding means, comprising in this case a arrangement with the collecting means, the light guiding means and the light diffusing means with its attachment means may be a garment itself, where the portion of the assembly which is exposed to the light is considered the external side of the garment assembly and the rest is considered the internal side of the garment assembly (2). Preferably the light guiding means of FIG. 15 are embedded in a piece of garment such as a foulard. Alternatively the tulip or button like light collecting means may be replaced with another kind of light collecting means, as the one shown and additionally the light collecting means may be attached to another garment, or to another body portion, or be placed remotely from the user, instead of on the hairs. The light collecting means (4) may be parabolic mirrors or other suitable light collecting means. Said light collecting means (4) may be permanently or non-permanently coupled to the rest of the light guiding means (8) and may comprise light concentration and/or deflection optic. Said light collecting means (4) may be complex optical instrument made of one or different materials including air or gas. There might be one or a plurality of light collecting means (4) and each of them might be connected to one or a plurality of wave guiding means (8). In the case of said light collecting means (4) being permanently attached to the light guiding means, they might be the end cross section of the light guiding means itself, which may have a variable cross section, to adapt forming a light converging optic or a constant cross section. The wave guiding means may have a section of full material, a single or multiple hollow lumens, or air bubbles. The material of the light guiding means might have impurities or additives for reflecting, deflecting or filtering light, or agents with different optical properties, including reflecting and filtering properties. The entire optical arrangement can be made of the same or different materials and could be manufactured by fusion, injection molding, extrusion, hot forming, stamping, 3D printing or by any other suitable manufacturing method. The optical arrangement of the garment assembly (2) (2) may comprise a light diffusing means (3), or a plurality thereof, along the light guiding means or at the end of the light guiding means (8). The light diffusing means (3) may be the output section or area of the light guiding means. The output end section (20') of the light guiding means being defined by the direction (10) of the light into the light guiding means. There might be one or a plurality of light diffusing means (4) and each of them might be connected to one or a plurality of wave guiding means (8).

FIG. 16 shows a wearable optical device (2), or a garment assembly, with an example of how a flat light collecting means (4) maybe placed on the surface of a garment. The collecting means may be on the back, on the front, or on the side of the garment and may be hanging or positioned remotely, so that it can be moved in the whished position according to the direction of the light source. Alternatively the collecting means may be permanently or removably attached to the garment, while the light diffusing means may be inserted through the neck portion of a garment.

FIG. 17 shows garment assembly (2), having a first part (12') and a second part (12"). The first part (12') of the garment assembly (2) is configured to be worn on top of an external garment and the second part (12') is configured to be worn under said garment, preferably under all garments, in direct proximity with the skin, meaning without any garment between the second part (12") and the skin, or on top of a partially light wave transparent garment (preferably partially UVB transparent garment). The first part (12') may comprise one or a plurality of light collecting means (4), or light concentrators (4), and a first portion (8') of the light guiding means (8) connected thereto, or integral thereto, to optically connect the internal side with the external side of the garment assembly (2). The second part (12") of the garment assembly (2) may comprise a second portion of the light guiding means (8"), which may be permanently attached to the first portion of the light guiding means (8'), or detachable from the first portion of the light guiding means (8'). The second part of the device (12") may also comprise a light diffusing means (3), or a plurality of light diffusing means. The light diffusing means (3), the light collecting means (4) and the wave guiding means may have the characteristics of the light diffusing means described in the summary of the invention and in the detailed description of the invention and/or may have the characteristics of the light collecting means. The light diffusing means (4) may therefore also be integral with the light guiding means itself (8), or the portion thereof (8"). The second (12") part of garment assembly (2), may be configured to be inserted from the neck of the user, therefore it may have the form of a collier, hanging on the chest or on the back of the user and entering the garments of the user by the neck hole of the garments. Alternatively the device may have other shapes than a collier, and/or attaching means, suitable for example to be hanging or fixed on the garments of the user, or on the body of the user (still over the garments), e.g. on the shoulders, or around the neck and it may enter the clothes or garments, to be brought in light communication with the skin, from other sides other than the neck hole of the garments. The second portion of the device may for example be introduced from the sleeves of the arms, from the lower part of the clothes, or from the upper part of the trousers, or even from a false pocket, and may resemble the connection of a pocket watch. The position of the diffusing means may be adjusted on different body portions, for example under the arms or in the armpits to reduce bacteria, or on muscles to make muscles appear bigger. The diffusing means may be hanging or may have attaching means to be attached to a garment or to the skin.

Figure 19:
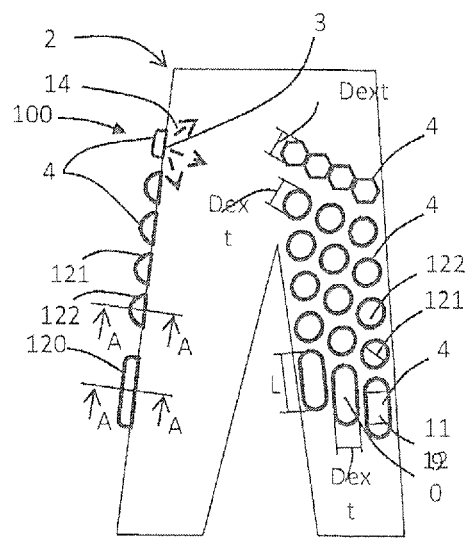
FIG. 19 shows an embodiment of the garment assembly, which may be, independently from the type of garments, which may be a pair of trousers or a different one, according to the embodiments of FIG. 1-10, with a plurality of independent optical assemblies (100), wherein light collector, light guiding means and light diffusing means (3) may integral in one single piece, as shown in FIGS. 20-23 and 38A-38F, or may be made of several components as shown in FIGS. 28-32 and 34-37.

FIG. 18 is an example of the embodiments of FIG. 1-6. In FIG. 18 the first portion of the device may be attached with the fabric of the garment and the second portion may be hanging from the first part without any attachment and may be free to be introduced underneath the garment. Alternatively the second part may be attached to an extension of the garment to be folded for example inside the neck, so that it hangs underneath all garments, as shown by the folding curve (B), which shows the trajectory of the second part (12") from the external side (24) to the internal side (23) of the garment assembly (2), preferably to the internal side of all garments worn by the user, in order to bring the part (12"), having the light diffusing means (3), or surfaces (3), in contact with the skin of the user (once the garment assembly is properly worn). The extension (12") of the garment assembly (2) with the diffusing means, may be on an upper body garment, e.g. on a jacket, or on a lower body garment, e.g. a pair of trousers. The garment extension with the diffusing means, or second portion (12"), may therefore extend from a jacket or from a pair of trousers and may be introduced from a jacket to underneath the jacket and optionally underneath other garments, from a jacket to inside a pair of trousers; from the trousers to inside the trousers; and from the trousers to underneath a jacket and/or the eventually other garments. The second portion of the garment assembly (2), may for example be introduced from the sleeves of the arms, from the lower part of the clothes, or from the upper part of the clothes, or even from a false pocket, as to resemble the connection of a pocket watch. The position of the diffusing means may be adjusted on different body portions, for example under the arms or in the armpits. The diffusing means may be hanging or may have attaching means to be attached to a garment or to the skin. Alternatively, it may work the other way around, with the diffusing means being part of an undergarment, which would be the second part (12") of the garment assembly (2) and the collecting means being attached to an extension of said undergarment and configured to be brought outside from the neck hole of the garment assembly and/or of all garments, in particular the hole of the upper garments. The second part may therefore be the garment in contact with the skin and the first part (12') may be the extension with the light collecting means hanging outside and facing the light source, in this case the curve (B) shows the folding line of the extension from inside to outside, or toward the external side (24) of the garment assembly (2). In general (for FIG. 1-39) it is conceivable to define a light guiding means (8) comprising at least a light collecting surface (4) and at least a light diffusing surface (3). In the embodiment of FIG. 19 a pair of trousers, or more generally a garment assembly (2) according to FIG. 1-18, with a plurality of independent optical guiding means, or portions thereof, is shown. In FIG. 19 light collecting means (4) (or surfaces), light guiding means (8) and light diffusing means (3) may be integral in one single piece, see examples of FIG. 20-23, 33-36, 38-39, or being therefore synergistically combined together to save space, provide attaching means for the fabric, save weight and minimize loses across the light guiding means. The fabric may have at least a percentage of materials that may melt during the manufacturing process adhering to the optical assembly and forming attaching means. Alternatively, during the manufacturing of the holes on the fabric by hot tools (or by friction) the fabric may melt around the hole or slot to prevent the fabric from fraying. Alternatively or additionally the optical assembly (8) or the light guiding means (8) may be made of several components like in FIGS. 24-27, 28-32 and as well 34-36. In general, in this application, it may be referred to the construct of optical (e.g. guiding, collecting and diffusing) means as optical assembly (100). The optical assembly, or a portion thereof, may be preferably disposed in the areas of the trousers, where the fabric is in contact with the skin, preferably on the areas where the skin is whiter, or less exposed to the sunlight, e.g. on the thigh, since whiter skin is more efficient in the vitamin D synthesis. On the external side or the garment assembly (2), the optical assembly, or a portion thereof, preferably the head (104) thereof (being the head of the optical assembly the portion extending from the external surface (6) of the fabric to the external side (24)) may be generally flat, e.g. being a Fresnel lens, or it may protrude from the surface of the garment. In both cases the projection of the perimeter of the head of the optical assembly (104) on the garment surface may have different shapes, e.g. a round shape (121, 122) around the axis X, which is shown for example in FIG. 20 or 21, a polygonal shape (123), or an elongated shape (119, 120), wherein the axis X may be the rotational axis (in the case of optical assemblies with round cross section), or an axis belonging to a symmetry plane of the optical assembly (in the case of optical assemblies which are not round). A protruding head portion (104), may have a light collecting surface (4) which may have the shape of a semi-circular, segmental, or faceted cupola (121, 122), or may have at least partially the shape of a barrel vault, which may be a semi circular, segmental, dominical, catenary, trought, squinch or boat barrel vault, or a combination of a barrel vault with two semi-cupolas, or semi domes, on the sides (119, 120). Said shapes allow a smooth distribution of the light rays, a light and robust construction and at the same time building a very thin central portion of the cupola (e.g. as in FIG. 21) or vault, which allows to build a cross sectional shape, according to the plane perpendicular to the external surface of the garment assembly (2), in the near proximity of the head (104), passing through the centre of the head portion (104), of the head portion having a thickness increasing, preferably exponentially, or preferably with increasing gradient between the centre and the periphery of the head portion (FIG. 21), at constant internal diameter of the neck portion (Di) (or of the neck (D)) and diameter of the head portion (Dext). In FIG. 19, seen from the top, the shape of the head (104) of the optical assembly (2) may have a polygonal perimeter, therefore forming a honeycomb like disposition of a plurality of optical assemblies, or portions thereof, which would allow a higher concentration of the collecting surfaces (4) and therefore a higher light collection and/or light transmission from the external side of the garment to the internal side of the garment assembly (2). A polygonal, preferably hexagonal shape of the perimeter of the head portion (104), seen from the top of the dome, also may have the advantage of allowing heads (104) disposition with heads that are closer to each other, by that reducing the space between the holes of the garments, while keeping the same area of the back surface (103) of the head (104). Alternatively a polygonal shape would allow increasing (by unchanged distance between the holes of the fabric) the area of the back surface (103) of the head (104) and therefore improving the retention of the fabric. Such a honeycomb-like disposition may be done with a plurality of Fresnel like head portions, or with a plurality of head portion which may have the shape of a cupola in pendentives polygonal plan. The optical assembly may have any suitable size to be attached to a pair of trousers or to another garment. However, it is conceivable that the bigger dimension of the optical assembly, respectively the head (104), as it is visible from the external side of the trousers, may be between 1 mm and 50 mm, or preferably between 4 mm and 25 mm, or even more preferably between 5 and 20 mm, or 5 mm and 15 mm, so that several optical assemblies, of the same or different size or shape, may be assembled to form a decorative motive, or geometry. The optical assemblies (100) or portions thereof, may be interconnected with each other by interconnecting means, e.g. by a thin layer of material, which may generate a rigid or a resilient structure made of a plurality of optical assemblies, which may form a predefined shape which may overmolded to the garment, or injection molded separately and applied to the garment at a later stage. A plurality of interconnected optical elements may form an enlarged optical assembly, made of optical assemblies, so that for optical assembly it can be understood a single optical assembly comprising light collecting means (4) and/or light guiding means and/or light diffusing means (FIG. 1-39), or a plurality of said optical assemblies (100), physically and/or optically interconnected with each other, forming an enlarged optical assembly (FIG. 34-36). Said thin layer of material, e.g. a thin film, or a rod, or a mesh interconnecting different optical assemblies, or portions thereof, may be permanent or removable after embedding the optical assembly, or the enlarged optical assembly to the garment, moreover it may be visible from the external side of the garment, or be on the internal side of the garment, or between the internal and the external side of the garment. In other words, it is conceivable that the layer of material interconnecting the optical assemblies is placed in the middle of two layers of fabric that form the final garment, or two different garments. Possible cross sections (according to the plane perpendicular to the external surface of the garment assembly (2), in the near proximity of the head (104), passing through the centre of the head portion (104), and possibly comprising the axis (X) of the optical assembly) of an optical assembly, or of a portion thereof are for example shown in FIGS. 20-39 and can be applied to the embodiments of FIG. 1-10, 15-18, being the entire or a portion (e.g. 8' or 8") of the light guiding means (8). In particular the optical assemblies of FIGS. 20 to 39, may include a so called static light collecting means (4), meaning that those collecting means do not need to be positioned to a specific angle with respect to the light radiations, but they may therefore collect light coming from multiple directions at the same time. Those kind of collecting means are particularly advantageous for clothes, since worn clothes are constantly in movement, especially with respect to the light source. The shape of the static collecting means, or the height of the dome (a flatter dome would be better for light radiation perpendicular to the surface (6) of the garment, while a more pronounced dome would collect more inclined light with respect to the garment surface (6) or to the dome axis (X)), may be however adapted to be worn on different position of the garment. It may be conceivable that the average light angle hitting a light collecting means (4) (or surface (4)) positioned on the shoulders, may be different that the average light angle hitting a collecting means on the arms or on the legs and therefore the shape may be adapted accordingly, for example to be more suitable to collect incoming light with a specific incident angle with respect to the plane where the collecting means lye. The interconnecting layer of material may be manufactured together with the optical assemblies or a portion thereof, e.g. injection molded, extruded, or hot stamped, with ultrasound, or it may be added in a later stage to create a predetermined shape or configuration, in order to simplify the combination of a plurality of optical assemblies in a garment. Preferably the holes are stamped on the fabric and the light guides (8) (or optical assembly (100)) may be overmolded separately from each other around the holes, to take the final shape according to FIG. 19-21, 33, 34-36, 39. An example of predetermined shape made of a plurality of interconnected optical assemblies, may be a flower shape, a squared shape, or a rhombus shape, or a triangle shape that can be combined together to form a pattern like a cosmatesque decorative geometry. It is conceivable however that such a decorative pattern is achieved also by using optical assemblies of different shapes. In other words, a cosmatesque decorative geometry may be composed by a plurality of shapes made by optical assemblies of the same shape and/or size, or by a plurality of optical assemblies of different shape and/or size. In both cases the material of the optical assemblies and the material of the interconnecting means may be the same or a different material. The use of predefined shapes or patterns of optical assemblies may be advantageous for a faster and cheaper assembly, of for characterizing the purpose of the garment e.g. to distinguish a sport garment from a casual garment, or a garment for male from a garment for female, or a garment for kids from a garment from adults, or to reproduce the symbol of a brand, or to vary the ratio between the surface of the garment assembly and the area of the holes (or of the area covered by the heads (104) of the optical assemblies).

In the case that pre-manufactured optical assemblies may have to be inserted into the garment through pre-existing holes (or slots), said holes may have to be advantageously manufactured through the garment before the insertion of the optical assembly of FIG. 20-39 (instead of opening the fabric by enlarging the fibers with for example a conical or pyramidal shape) depending on the characteristics of the fabric, wherein the optical assembly has to be embedded, in order to robustly retain the optical assembly and/or to allow the assembly of the optical assembly into the fabric, with a diameter, or at least one of the dimensions (in case the hole is not circular), being between about 50% to 80% smaller than the diameter (D), or than at least one of the dimensions (D or L) of the neck section (102), to 10% bigger than the diameter (D), or than at least one of the dimensions (D or L), of the neck section (102). Said dimensions for the hole may be advantageous for both the insertion of pre manufactured optical assemblies and the injection molding of the optical assemblies directly over the fabric. The optical assembly may therefore have the general shape of a blind grommet or of a hole plug. In all embodiments wherein the fabric may need pre-manufactured holes before the insertion or the injection of the optical assemblies, the holes may be round, triangular, elliptical, squared, polygonal, being obtained by cutting away or stamping away material, alternatively the hole may be obtained by cutting a minus-shaped, a plus shaped, an x-shaped, or a y-shaped slot, without material removal. This may be advantageous for simplifying the manufacturing and improving the retention of the fabric and would allow using different size of optical assemblies in the same hole, since the final hole shape would be defined by the section of the optical assembly passing there through. In order to retain the fabric within the channel (101) around the neck portion (105), at least one dimension (Dext), or the diameter (Dext), of the head of the optical assembly (100) and at least one dimension (Dint), or the diameter (Dint), of the flange (106), may be between 5% and 100%, preferably between 50% and 85% bigger than the diameter (D), or than at least one of the dimensions (D or L), of the neck section (102). An alternative manufacturing method would include the enlargement of the threads of the fabric through the insertion of a preferably conical or pyramidal shaped partially formed optical assembly (100) to be hot formed after the insertion. In this case no holes need to be manufactured. The conical or pyramidal shaped needle like optical assemblies may be molded in a mesh, meaning that they are interlinked together, so that a mesh with many needles can be positioned on the eyelet fabric having a predetermined eyelet disposition corresponding with the disposition of the needles in the mesh, so that multiple needle can be inserted and joined by or fusing, melting to the fabric at the same time, before they are separated from each other, by for example bending the mesh and/or removing the flash in excess. Another alternative is the overmolding of a fabric having pre-manufactured embroidered (or non embroidered) and/or cut, cut by a rotating cylindrical tool empty in the centre, drilled or stamped (with or without material removal) holes or slots, which in this case would have the size of about the diameter (D) or between 60% smaller to 20% larger than the diameter (D), depending on the elasticity and thickness of the fabric and the dimensions of the optical assembly. May the optical assembly (100) be overmolded (or alternatively inserted after being manufactured separately), the final geometry may partially embed the internal surface (5) of the garment assembly (2) (FIG. 20, 34-36), or it may contact the garment assembly only on the external surface (6), preferably having the arc shape thinner in the middle (like in FIGS. 33A-33C) and wherein its thickness preferably increases exponentially from the centre to the perimeter, wherein the optical assembly is attached to the fabric with the back surface (103) of the head portion (104), said head portion being in this case the entire optical assembly (2), a convex light collecting surface (4) on the external side of the garment assembly and a concave diffusing surface (3) on the internal side (23) of the garment assembly (2). The optical elements of FIG. 19 may be used as well on a beach visor or on the visor of a baseball cap or of a hat.

FIGS. 20 to 39 show the cross section A-A of several embodiments of the optical assembly, or a portion thereof, e.g. the head (104), that may have a rotational symmetry, and therefore may have, seen form the top of the dome, or from the external side of the garment (see right half of FIG. 19), a circular external shape having a dimension, or, in this case, a diameter Dext, or may have a planar symmetry, and therefore may have for example an elongated shape (119, 120), with length (L) as shown in FIG. 19, having the a width Dext, or any other regular or irregular shape, having one dimension that may be equal to a dimension Dext. In the case of the optical assembly (100) with an elongated head shape (119), the head (104) of the optical assembly may be assembled from different portions, e.g. a central straight portion, having the general external shape of a portion of a cylindrical mantel, or a rectangle, in the case of a flat head, e.g. having a Fresnel surface, and two lateral rounded portions, having a generally semi-hemispherical shape, or a generally semi-hemispherical cup shape, or having the surface of a quarter of a sphere, or of an empty sphere. The two lateral semi hemispherical elements may be also coupled, or jammed, or glued together to form a generally hemispherical head portion (121). Alternatively the two halves may be kept in contact by the hole of the fabric (F) where they are, preferably tightly, inserted, or with an eyelet, as FIG. 30 may show, or by both, the fabric and a washer (114), as FIG. 24-27 may show. It is conceivable that in the embodiment of FIGS. 20-32 and 37 the cross section shown may be the one of an optical assembly with the head portion (104) made of one part (120, 122), two parts (121), three parts (119), or more parts. The maximum footprint (Dint) of the optical assembly on the internal side (23) of the garment assembly (2) may be smaller, bigger or equal to the maximum footprint (Dext or L) of the head portion (104) of the optical assembly (100). The optical assembly, or a portion thereof, may comprise attaching means made of the same or of a different material. According to FIGS. 20 to 39 the optical assembly, or a portion thereof, may diffuse the light directly to the skin underlying the optical assembly or may be coupled to a second portion (100″) of the optical assembly, or a second portion (8″) of the guiding means (8), (as shown for example in FIG. 34-37) to transfer the light (preferably additionally to diffusing locally) to a different, preferably to a more remote area on the internal side of the garment assembly or under a different garment.

Figure 20:
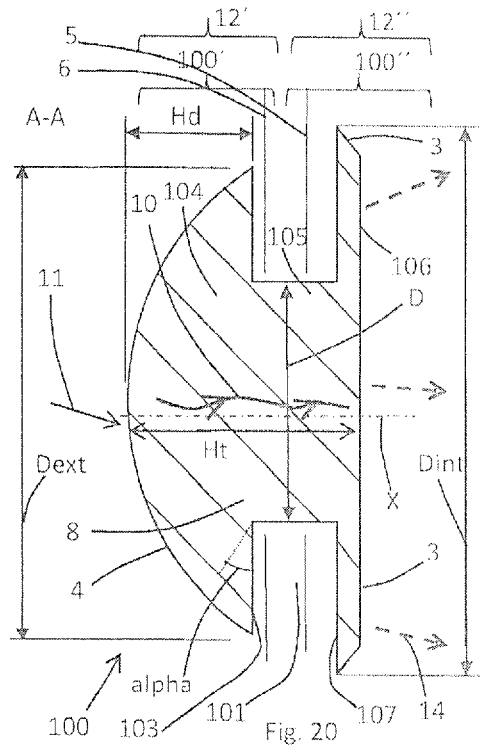

FIGS. 19 and 20 shows the cross section A-A, of the light guiding means (8) or of the optical assembly (100) according to FIG. 1-44 (in particular to FIG. 19) which comprises light collector, light guiding means and light diffusing means and attaching means integral in one piece. The optical assembly may have two parts (12′, 12′), an external first part (12′), at least partially visible from the outside of the garment assembly and an internal second part (12′), at least partially visible from the internal side of the garment assembly (2). The optical assembly may comprise a head portion (104), on its external part (12′), a neck portion (105), between the head (104) and a flange portion (106), on its internal portion. FIG. 20 shows also a portion of the garment assembly (2), which comprises a first part (12′) and a second part (12″), wherein the first part comprises the external side of the garment and the external portion of the optical assembly and the second part comprises the internal side of the garment and the internal portion of the optical assembly. The optical assembly may be attached to other optical assemblies, or form with other optical assemblies an enlarged optical assembly, through interconnections, which may be between the external surface (6) of the garment assembly and the internal surface (5) of the garment assembly (2), or alternatively between the external surface (6) of the garment assembly and the second portion (100″) of the optical assembly, or alternatively between a part of the internal portion (100    ) of the optical assembly (100) and the internal surface (5) of the garment assembly. The external portion of the optical assembly (100) may comprise a light collecting surface (4), which may have a flat, concave, convex external contour, or may have a zigzag external contour, or a mix of said different kind of contours. In the case of a convex contour the external shape, or head of the optical assembly may be hemispherical, elliptical, or semielliptical, torispherical, flat dished, or dished. The light collecting surface may have a convex contour, or in other words a dome shaped contour, with the dome height (Hd) measured (in direction of the axis (X) of the dome), from the base of the dome (103), or the external surface of the garment (6), to the top of the dome. The optical assembly may have a cross section reduction, having a dimension (or a diameter) D, that delimits the internal side of a channel (101), said cross section reduction extending, along the axis (X), from the base of the dome (103) in the direction of the internal portion (100′) of the optical assembly (100), to the shoulder (107) of a flange (106), which extends radially with respect to the neck portion (105). Said flange (106), may have a maximal footprint (or diameter) (Dint), larger, equal or smaller than the dimension (Dext) of the maximum footprint of the projection of the head portion (104) (or dome) on the external surface (6) of the garment assembly, and may be continuous around the perimeter of the optical assembly (100), or discontinued by radial apertures across the perimeter, in the latter case forming a toothed frame, with radially extending teeth (see for example FIG. 23E). In FIG. 19-27, 30, 37 (only shown in FIG. 23E: three teeth flange) the flange (106) may be divided into 2 (therefore having 2 radial apertures), 3 or more parts separated by radial apertures extending from the periphery toward the center of the flange. In order to simplify the insertion of the optical assembly into the hole or into another portion of the optical assembly the flange may have a single aperture extending from the periphery in inward direction. In other words, the flange (106) of FIG. 23C for example may have a radial notch (106*b*) as shown in FIG. 23G. This may imply that the element of FIG. 23C before forming may have such a shape that after forming may take the notched shape of FIG. 23G. Such a notch, to simplify the assembly of the optical assembly in the fabric, may be present in any other embodiment (for example in the embodiments of FIG. 20-32). The positioning of the optical assembly of FIG. 21 into an hole of the fabric may be performed, with the help of a pin shaped tool, by placing the hole of the fabric on the side of the flange portion, inserting the pin shaped tool into the cavity of dimension Di of the optical assembly by passing the pin first through the corresponding hole of the fabric, forming a friction coupling between the pin and the optical assembly, pulling the pin as to force the optical assembly against the fabric, positioning a notch (106*b*) (as shown in FIG. 23G) on the perimeter of the hole of the fabric, rotating the pin with the optical assembly in order to make the perimeter of the hole of the fabric to enter the neck portion of the optical assembly.

The fabric wherein the optical assembly (100) is placed may have a hole having a dimension close to the dimension (D) of the optical assembly, which in the example of FIG. 33 may be the internal, preferably smallest dimension of the back side (103) of the head (104) of the optical assembly. The optical assembly may have a circular geometry, and therefore may have, seen from the external side of the garment, a circular external shape and may have a dimension or a diameter Dext, and/or may have a planar symmetry, and for example an elongated shape, having a width Dext, or any other regular or irregular shape, having one dimension equal to the dimension Dext. The second portion of the optical assembly may have one or more diffusing surfaces (3). In general all surfaces (3) facing the internal side of the garment assembly may be light diffusing means. More precisely any surface (3) of the optical assembly (2) that may potentially diffuse light on the internal side (23) of the garment assembly, directly or after at least one reflection, wherein said diffused light, after leaving said diffusing surface (3), do not extend along the external side (24) of the garment assembly before passing through its internal side (23), may be considered light diffusing means (3). In FIG. 20 the back surface (3), meaning the surfaces facing the internal side (23), of the light diffusing means (100) is generally flat, with exception to the peripheral zone of the flange portion (106) where the diffusing surface may be inclined or curved toward the shoulder (107) of the flange (106). However, the back side of the optical assembly, or of a portion thereof may be concave (e.g FIG. 21) or convex, or concave and convex (e.g. FIG. 27, 37B). A cavity in the optical assembly which is in direct communication (without necessarily having to pass through other materials than air) with the internal side (23) of the garment assembly may be considered also part of the internal side (23) of the garment assembly (2). The light waves entering the optical assembly may be diverging, converging or parallel. The light waves entering the internal side (23) may also be diverging, converging or parallel. Ideally the light waves entering the collecting surface (4) of the optical assembly may converge, in order to bring more light into the reach of the hole of the garment, or of the dimension (D) neck portion (105) and diverge after leaving the diffusing surface (or surfaces) (3), in order to spread on a larger portion of the internal side (23) or of the skin. This effect is achieved for example by the optical assembly of FIG. 21, as it can be seen on FIG. 33A-33C. In general diverging light waves may be advantageous to increase the light density, on the internal side of the garment assembly (2), or of the optical assembly, alias on the skin, when the sunlight is weak, or alternatively to converge the light to be guided more remotely into a wave guiding means, or to diffuse the light on the skin, with the assumption that the focal point of the optical element obtained by the dome geometry, is within the optical assembly, so that the light waves, diverging after the focal point, are less dense again when they reach the skin, or the internal side of the optical assembly. Same considerations, as already done for the dimension Dext, applies for the internal dimension (Dint), which may be smaller, bigger or equal to the diameter/dimension (Dext) of the optical assembly (100). The optical assembly (100) may have a lateral channel (101), which may extend around the optical assembly, which is conceived as an attaching means for attaching the optical assembly (100) to the garment. The depth of the channel may vary according to the type of connection with the fabric of the garment and/or with the type of fabric, and/or the way the fabric is weaved. The channel, seen from the cross section A-A of FIG. 20, may have a squared, V-shaped or U-shaped or round cross section, according to the symmetry plane of the optical assembly generally perpendicular to the external surface (6). Considering the shape of the channel around the optical assembly and therefore its shape with respect to the cross section which follows the plane of the garment surface, the internal perimeter of the channel may be ring shaped, or elongated-ring shaped, or polygonal shaped. It is conceivable, that if the external shape of the optical assembly, looking at the outside surface of the garment, is the one of a honeycomb, the internal perimeter of the section of the channel (101), which follows the plane of the garment surface, may have the same honeycomb shape. However it is also conceivable that for simplifying the construction of the shape of the internal perimeter of the cross section of the channel, generated by the plane passing through the garment surface, is nearly round or exactly round, even when the perimeter of the shape of the optical assembly visible from the external side of the garment, or simply said the external shape, or the perimeter of the light collecting portion, or of the collecting means of the garment assembly is polygonal. Instead of a channel the optical assembly may have a protrusion configured to be attached to the fabric, e.g. with holes like a button. Said protrusion may be located on the internal or on the external side of the fabric, as described for the interconnecting layer. Preferably the head (104) of the optical assembly may have a size between 1 and 100 mm, preferably between 5 and 80 mm, or preferably between 3 and 15 mm, however it might be even larger, e.g. in the case of elongated optical assemblies in the direction of the dimension that is not shown in FIG. 20, or in the case that the external surface would be flat, or would have a Fresnel lens shape. Preferably the ratio D/Hd of the dimensions the optical assembly may be between 8 and 1, or preferably between 5 and 1,6, or more preferably about 2,4. These ratios have the advantage that a higher amount of light is collected, preferably from all directions. The preferred ratios or proportions between the dimensions of the optical assembly may provide a higher amount of collected light to pass through the hole of the garment, which is equivalent to the minimal cross section of the optical assembly. Additionally the presence of an optical assembly instead of a simple hole on the garment may assure air tightness and therefore less heat dissipation. The round dome shaped geometry may additionally provide a pleasant feeling while wearing or handling the garment and may provide protection to the garment from wear and scratches, e.g. when the garment is washed and the surfaces of the garment rub against each other. It is conceivable that the dome geometry of FIG. 20, which may have the general shape of a spherical cap, may be also transformed in a Fresnel optic. In this case the ratios or proportions described would still be valid, considering the original lens which is reduced to the Fresnel geometry, since the Fresnel optic would be a transformation of the dome shaped lens of the head of the optical assembly e.g. of FIG. 20-21. The advantage of a Fresnel optic may be that the assembly becomes more flat and therefore it may be used for distinguishing male and female type of garments, e.g. round shaped for females and the sharp edged Fresnel for males. However the Fresnel shaped optical assembly is not necessarily sharp, but may be rounded and provide comfort as well, without causing wear or scratches. The shape of the diffusing surface or of the diffusing element (3) seen from the cross section A-A may be at least partially flat, concave or convex, according to the desired optical effect to be obtained, and/or the feeling on the skin, e.g. a convex contour may give comfort to the skin, provide a massage that may be good for preventing cellulites and concentrate the light radiations for making them converge into a light guiding means (8) (see also FIG. 34-37). The optical assembly may preferably be at least partially UVB transparent, and at least partially UVA opaque. This might be achieved for example with titanium dioxide doped or coated PMMA or COC. An example of an optical assembly with a concave diffusing surfaces (3), or diffusing surface (3), may be the one shown in FIG. 21.

Figure 21:
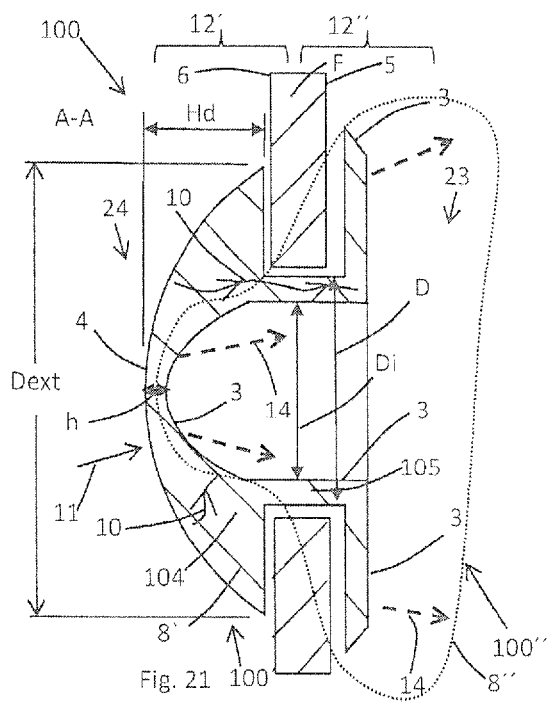
Figure 22:
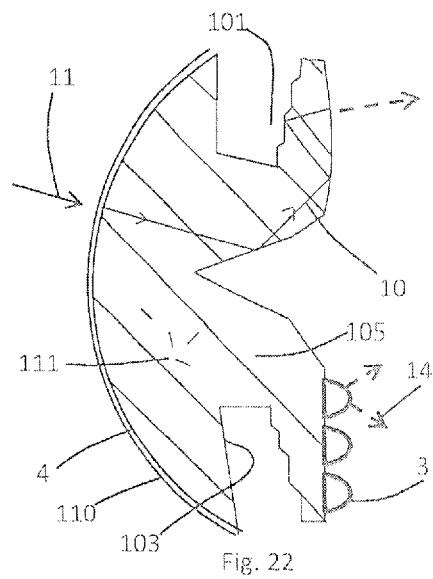

FIG. 21 shows an optical assembly (100), e.g. which may be the one the one of FIG. 1-4, 19 or in particular FIG. 20, with a concave diffusing surface (3). The optical assembly may comprise a head portion (104), a neck portion (105) and a flange portion (106). The cross section A-A of the head portion (104) may be, dome shaped, bridge shaped, mushroom shaped and/or preferably C-shaped, arc shaped, more preferably the bridge-shaped head portion may be thinner in the centre, wherein the centre is defined by the axis (X) of the optical assembly, and thicker on the side, wherein the thickness of the cross section, with respect to a symmetry plane passing through the axis (X), of the head preferably increases from the centre of the dome to its perimeter (from the centre to the side) monotonously or exponentially e.g. FIG. 21, 23-26, 27 (excluded for the Fresnel portions), 37A, 37C. The head portion may preferably have the general 3D shape of the mantel of the spherical cap of a hollow sphere, the resulting hollow spherical cap may be the volume resulting by cutting the difference between two spheres with different radius and different centre, one contained into the other, so that the distance between their two centers is smaller than the positive difference of their radios, with a plane perpendicular to the axis passing through their centers, preferably said plane not containing the line connecting the two centers, so that the resulting spherical cap is thinner in the middle. The head portion may have also the shape of an elongated hollow spherical cap, preferably thinner in the middle. The neck portion (105) may therefore take the shape of a cylindrical mantel (105), capped by said dome shaped head (104) on the external side (24) and by a ring shaped or crown shaped flange (106). The neck may have empty lateral regions, or may be non-unitary, as for example in the embodiment of FIG. 23E, consequently the flange extending from the neck portion may also not be a unitary ring, but may have a crown shape with radially extending teeth, or may alternatively have radially extending grooves or protuberances on the internal surface extending from the cavity made by the concave internal surface (3) at the centre of the optical assembly to the distal end (opposite to the centre of the optical assembly where the axis (X) pass through) of the flange portion, to put in air communication the concave central portion with the internal side (23) when the back surface (3) of the optical assembly is on the skin. This is advantageous because the moisture generated by the body would not be trapped inside the cavity of the optical assembly (100). In other words, the optical assembly may have a radially symmetrical geometry, a head (104) and an axially thereto adjacent neck section (105), wherein the head is radially enlarged relative to the neck (105) and wherein said neck section merges, facing away from the head (104), into a radially widened abutment shoulder (107), which forms an axial end of an internal channel (101), which may forms a receptacle and therefore an attaching means for a portion of the garment. The head portion (104) of the optical assembly, according to FIG. 21-33, 37-38, may have the general shape of a negative meniscus lens with a convex anterior side (4), or a convex light collecting surface (4), and a concave posterior side (3), or concave light diffusing surface (3), having a back side (103), preferably at least partially flat (however it may be also curved), and wherein the peripheral portion of the head with respect to the axis (X), viewed e.g. in the cross section of FIG. 21, is pointed, or has a small radius (e.g. between 1 mm and 0,1 mm) and thus wherein the lens is delimited peripherally by the intersection of the collecting surface (4) and the surface of the back side of the lens (103), and wherein said intersection may form a closed line. The cross section of the head, relative to its symmetry plane, may have the shape of the cross section of a negative meniscus lens, relative to a symmetry plane. Like the cross section of a negative meniscus lens, or convexo-concave lens, the head portion has a greater curvature radius on the convex side (being the external collecting surface (4)) than on the concave side (being the external collecting surface (4)) and wherein the concave and the convex sides are connected by a line perpendicular to the (preferably optical) axis (X) of the head to form the (in the 3D ring shaped) back side (103) of the head portion (104). This definition of the head portion as a negative meniscus lens is applicable also in the forthcoming embodiments and in particular to the embodiments of FIGS. 28-32 and 37A. Such a geometry has the effect of increasing the light collection from all directions and simultaneously to generate an image distortion of the internal side (23), looking at the optical assembly from external side. Alternatively to the shape of a negative meniscus lens, the head portion (104) may have the general shape of any divergent lens, e.g. a bi-concave, or a plano-concave lens. The neck portion may be formed by a cylinder, a continuous generally cylindrical mantel, or discontinuous cylindrical mantel made by a plurality of axially extending legs (FIG. 23E). Said optical assembly may be made of one component, as shown for example in FIGS. 20 and 21, or may be made by a plurality of components, as shown in FIG. 23-32; it may be made by a single material, or may comprise different materials. The diffusing surface (3), may be at least partially concave in such a way that, the distance between the at least partially convex collecting surface (4) and the at least partially concave portion of the diffusing surface (3), increases from the centre of the head (104), to the side, or lateral portion delimited by the dimension Dext of the head (6), of the head (2) of the optical assembly (2). This shape of the head provides the optical effect shown on FIG. 33A-33C. In this case the light radiations through the collecting surface (4) converge inside the head of the optical assembly up to the diffusing surface and then diverge after exiting the diffusing surface (3). This allows collecting and guiding more radiations to the internal side of the garment, or of the garment assembly, than a simple hole on the garment may do, while still allowing the radiations potentially reaching the skin, when the garment is worn, or reaching the internal side (23) of the garment assembly, with a density that is inferior than the density of the light hitting the collecting surface (4). In fact, another effect of the concavity of the diffusing surface, also together with the neck portion, is, at least partially spacing apart the skin of the user wearing the garment assembly, from the diffusing surface (3) so that the light radiations, preferably the UVB radiations, have some space to diverge, before potentially reaching the skin when the garment assembly (2) is worn. Before reaching the internal side of the garment assembly, the light is transmitted through the air below the concave diffusing surface (3) and through the cylindrical extension of the head of the optical assembly. The neck portion together with the flange portion, which may extend radially from the neck portion, or in other words may diverge from the neck portion, may be a glowing light guiding means (8) that may optionally partially guide and/or optionally partially transfer and spread vertically and/or radially the collected light, which may not exit from the central concave surface (3) of the optical assembly. The neck portion (105) may have an external dimension which is smaller or generally equal than the dimension Dext of the head of the optical assembly, and which is also smaller or generally equal than the dimension Dint of the diffusing portion of the optical assembly, forming in this way a channel (with a straight cylindrical or conical portion) around the optical assembly, that may have the function of holding the fabric of the garment and/or other layers of material e.g. a layer of reflective material, or a layer of predefined connecting material, or connecting means to hold in a predefined shape a plurality of optical assemblies. The height of the cross section of the channel, as shown in FIGS. 20 and 22, may, moving radially, be constant as shown in FIG. 20 or may increase as shown in FIG. 22. The width of the cross section of the channel, moving vertically, may also be constant increase or decrease. The embodiments of FIG. 20 or 21, eventually with some modification regarding the flange portion and/or the neck portion and/or the head portion, may have any of the features seen in FIGS. 24 to 32. It may for example have protrusion on the back surface (103) of the head portion to better fix the garment within the neck portion (102). Said protrusions, may also extend from the flange portion, or from any connecting, fastening, or optical element between the head portion and the flange portion (e.g. the layer (15), which may be both a fastening washer and/or a reflective layer as shown in FIG. 28), they may extend for a length which is shorter than the neck portion, or may extend toward the neck portion and contact, or even merge with, the flange portion. The neck portion has generally the functions of guiding and/or reflecting the light toward the internal side of the garment assembly, forcing or keeping the garment around the optical assembly, spacing the diffusing surface from the internal side of the garment assembly (2), where the skin of the user is situated. The optical assembly in FIG. 20 or 21 may be partially modified into a multi component optical assembly. The multi component optical assembly (100) may comprise a fastening counterpart (114), generally toroidally shaped (FIG. 24, 25), or having a generally elongated toroidal shape (FIG. 24, 25), or a cup shape (FIG. 26), as shown for example in FIGS. 24-27 and 37, or a c-clip shape, which may be embedded, jammed (FIG. 24), screwed (FIG. 25), welded or glued, to the rest of the optical assembly, e.g. to the head (as shown for example in FIG. 28-32), the flange (as shown for example in FIG. 24-27, 37B), the neck, or a plurality of said portions, as shown for example in FIG. 30. The connection means to attach the optical assembly to the garment may be at the same time also reflecting elements, in the sense that they may have coated or uncoated surfaces that reflect light, and/or guiding elements and or diffusing elements, as shown in FIG. 24-32, 34-37. The cap shaped counterpart (114) of FIG. 26 may have the shape or of a meniscus lens and further diverge the light rays as shown in FIG. 38a-38F. Said meniscus lens may also be at least partially transformed, or reduced, into a Fresnel lens. The advantage of generally sealing the optical assembly, or a portion thereof, with a cup shaped counter element (114) is that it would prevent moisture or dirt depositing in the internal side (3) of the head portion (104), e.g. when the temperature difference between the internal side (24) and the external side (23) of the optical assembly is big. Preferably, counter elements may be a converging, a diverging, a neutral, or a diffusing optical element. The central portion of the cup shaped counter element may be flat, or may have the shape of a bi-concave (FIG. 38E-38F), plano-concave (FIG. 26), or negative meniscus lens (38A-38D), to additionally diverge light rays toward the internal side of the garment assembly, wherein the plano-concave lens and the negative meniscus lens may be used in both direction, meaning with the concavity facing the internal cavity of the optical assembly (as shown in FIG. 26, for the case of a plano concave lens, or as shown in FIG. 38A, 38B, 38F for the case of a negative meniscus lens), or facing the internal side of the garment assembly (23) (see for examples the simulations on FIGS. 38C and 38D for the negative meniscus lens). The same applies for the head portion (104) and for the cup shaped counterpart (114) (also shown in FIG. 38A-38F). Multiple possibilities that would work well are shown on FIG. 38A-38F. It is conceivable that, in order to make the optical assembly possibly thin and still efficient in collecting light to combine a head portion (104) having a convex collecting surface (4) (and therefore a concave diffusing surface (3) on the back side of the dome) as in FIGS. 38A, 38C and 38E and a counterpart (114) having a concave, diffusing surface (3) on the internal side (23) of the garment assembly (and a convex surface facing the internal side of the optical assembly) (see FIG. 38C), or a counterpart (114) having a convex, diffusing surface (3) on the internal side of the garment (23) (and a convex surface facing the internal side of the optical assembly) (see FIG. 38A), or a counterpart (114) having a concave, diffusing surface (3) on the internal side of the garment (23) (and a concave surface facing the internal side of the optical assembly) (see FIG. 38E). Other alternatives include a concave collecting surface (4) (and a convex diffusing surface (3) on the internal side of the optical assembly), with a counterpart (114) having a convex, diffusing surface (3) on the internal side of the garment (23) (and a concave surface facing the internal side of the optical assembly) (see FIG. 38B); or a concave collecting surface (4) (and a convex diffusing surface (3) on the back side of the dome), with a counterpart (114) having a concave, diffusing surface (3) on the internal side of the garment (23) (and a convex surface facing the internal side of the optical assembly) (see FIG. 38D); or a concave collecting surface (4) (with a concave diffusing surface (3) on the internal side of the optical assembly), with a counterpart (114) having a convex, diffusing surface (3) on the internal side of the garment (23) (and a concave surface facing the internal side of the optical assembly) (see FIG. 38F).

Another advantageous possibility, not shown in the figures would be to combine together two plano-concave lenses in all the possible combinations, obtaining for example a head portion (104) having a concave collecting surface (4) and a flat diffusing surface (3) (on the back side of the dome) and a counterpart (114) having a concave, diffusing surface (3) on the internal side of the garment (23) and a flat surface facing the internal side of the optical assembly; or for example a head portion with a flat collecting surface (4) coupled to a concave diffusing surface (3) (on the back side of the dome) and a counterpart (114) having a flat, diffusing surface (3) on the internal side of the garment (23) and a concave surface facing the internal side of the optical assembly (100).

FIG. 38A-38F have the purpose to show the path of the light rays along the optical assembly (100). The optical assemblies of FIG. 38A-38F are advantageous for assuring a equally distributed light diffusion on the internal side of the optical assembly (23), wherein the light density on the diffusing surface (3) is lower than the one on the collecting surface (4), or in other words the density of the diffused light (14) is lower than the density of the incoming light (11). At the same time the embodiment of FIG. 38A-38F provide a certain distance between the collecting surface (4) and the diffusing surface (3). It is conceivable that the optical assemblies of FIG. 38A-38F are not empty, but solid, and may therefore be positive lenses. This would be advantageous in case the light has to be concentrated because otherwise it would not be strong enough. With the geometry of FIGS. 38E and 38F it may be possible to have a certain light exit angle within a shorter thickness of the optical assembly (Ht), and therefore to obtain a bigger light rays density decrease between incoming light (11) and diffused light (14) within the same distance (Ht). The domed geometry on the external side of the garment (FIGS. 38A, 38C and 38E) is additionally advantageous for collecting inclined incoming light (as shown in FIGS. 38A and 38B). The shapes of FIGS. 38A, 38B, 38C, 38E and 38F, having at least one of both collecting and diffusing surfaces which are at least partially convex, are advantageous for pushing the optical assembly inside a hole of the garment and attach it thereto, while the at least partially convex shape of the diffusing surface (3) of FIGS. 38A, 38B, 38E and 38F may be additionally advantageous for providing a massage to the skin, or at least an additional comfort feeling, when the garment is worn. Finally shapes shown in FIG. 38B, 38C, 38D, 38E, 38F, 38G, compared to the one of FIG. 38A may be advantageous to obtain a flatter shape of the optical assembly (100). There might be other geometry of the optical assembly which may have a higher ratio between the density of the incoming and diffused light, or that may have a better light collecting efficiency for a specific light angle, however the geometries have been selected as the best compromise between following criteria: —maximize the total light that is guided through a hole in the fabric from all incoming directions, without the need of continuously reorienting the collecting surface with respect to the light source; —minimize encumbrance on the external side (23) of the garment assembly and allow the maximum bending and flexibility of the fabric; —maximize the divergence angle (AE) of the diffused light (14), starting from a parallel incoming light radiations (11), to reduce the light density on the internal side of the optical assembly (100); —minimize light concentration on the internal side of the garment; —minimize the size and the complexity of the optical assembly; —increase safety and protect the user. The optical assemblies of FIG. 19-32 may lead to the internal side of the optical assembly at least between 10% and 90% of the light (preferably UVB light) hitting the collecting surface (4), or preferably at least between 30%, and 90%, or even more preferably at least 35% to 80%. The simulation of FIGS. 33 and 38 show that, in ideal conditions such as perfect surfaces and 100% transparency, the percentage of the diffused light rays with respect to the light rays that hit the collecting surface may be close to 100% for light hitting the optical assembly with an angle AL of about 0°, or also with an higher angle, with respect with the axis (X) of the optical assembly. However considering a reflection of about 5% to 10% of the incoming light and some losses during the transmission through the material that is never 100% translucent, in particular with respect to UVB light, the conversion rate between incoming light (11) and diffused light (14) may be worst that the ideal one, so that the real percentage of the diffused light rays with respect to the light rays that hit the collecting surface, especially UVB rays, may go down sensibly. However it is conceivable that some reduction in the light conversion rate may be wanted, for example in order to exclude a portion of the harmful UVA and UVB radiations and letting through only the radiations that are more efficiently generating the synthesis of vitamin D, which appear to be wavelengths of about 295 nm to 305 nm. This may be achieved e.g. using titanium dioxide mixed within the material, or as a coating. Another reason to reduce the conversion rate between incoming and diffused radiation may be in order to reduce transparency to visible light, so that the optical assembly becomes opaque to the human eye, while still promoting UVB to be diffused. It was shown in the simulations, under ideal conditions (without transmission dissipation and reflection, which would occur by any material), that the total light diffused on the internal side of the optical assembly may be higher, equal, or even lower than the light that would pass through a simple hole through the garment, having an equivalent surface to the surface of the neck of the optical assembly. However the garment assembly (2) with the optical assembly may additionally offer protection from cold and at least partially from harmful radiations.

The optical assemblies of FIG. 19-32 may maximize the divergence of the diffused light (14) so that the irradiated area on the internal side of the optical assembly is always equal or higher than the area of the collecting surface (4), to such an extent that 50% to 100%, preferably 75% to 100%, or more preferably 99% to 100% of the surface on the internal side of the optical assembly has a light density, preferably UVB light density (for vitamine D synthesis), or preferably UVA (for tanning: a shape may be made with the optical elements to tan a figure on the body) light density, or preferably the light density of both UVB and UVA, or a portion thereof, which is lower, than the light density hitting the collecting surface of the optical assembly.

However it is conceivable, that it may be advantageous to exclude UVA and to concentrate UVB rays, e.g. with an optical assembly comprising a convergent optic (e.g. the head portion (104) of FIG. 37B), to promote vitamin D synthesis, e.g. in places with less sunlight.

Even if the optical assembly for some reasons would perform not as well as a simple hole in the fabric in terms of UVB transmission (e.g. because of losses, reflections, wear of the optical assembly, etc.) it may still have the benefit of protecting from UVA, or from cold air, or water or snow (e.g. if applied to a snowboard trousers or to a neoprene suit). Therefore there is a synergetic effect: UVB transparency and protection from cold and/or UVA. Another synergy may be the protection from heat, by having the UVA and part of UVB reflected by the optical assembly itself with or also without reflective coating, in particular UVA reflecting, or absorbing, coating (110). In all embodiments, some elements may have a coating representing a barcode or a QR code or a logo, to gather information about the garment assembly, e.g. the total area of the surface covered by the optical elements or the like, or the type of the optical assemblies implemented in the garment assembly (for example by a mobile device that runs a mobile application to be used together with the garment assembly to give feedback to the user). Alternatively, in order to manufacture a bigger barcode or QR code, or a logo, two or more adjacent optical elements heads may be joined together (still sitting on the original 2 or more holes of the garment) to form a larger surface. In winter clothes the UVA may be preferably absorbed (e.g. by adding an additive to the UVB transparent material) to keep the heat inside the garment, while during hot weather e.g. for tunics, the UVA may be preferably reflected, by for example using a coating on the external surface of the optical assemblies. To keep the heat inside the garment assembly if may be advantageous to include the UVA absorbing layer (110) closer to the diffusing surface (3), e.g. by coating it. The presence of a metal eyelet without coating to support the optical assembly have a synergetic effect, because on top of giving support to the optical assembly it may quickly disperse the heat from the optical assembly or from the skin. This may happen because there may be hot weather or just because the user is practicing sport activity. The eyelet may be in plastic or in metal or alloy. A metal eyelet, in particular an aluminum eyelet, has the synergetic effect that additionally to the fact of offering support to the optical assembly and/or is lighter and/or it quickly transfers heat, it is better at reflecting light, providing additional guide to the light inside the wearable garment assembly in the case that the light would prematurely exit the optical assembly. A metal eyelet may additionally transfer electric charges to the outside avoiding the garment or the garment assembly being electrically charged, e.g. by rubbing. The absence of eyelet and therefore a garment with the plastic optical assemblies mounted directly on the fabric, may be advantageous, because it reduces manufacturing costs and/or because it is lighter and/or provides more isolation, air tightness and/or lightweight. In all embodiments, the optical assembly, may be at least partially UV translucent, or preferably at least partially UVB translucent, and may at least partially reflect, or absorb, at least a certain wavelength of the visible light, to at least partially reducing the visibility on the inside of the garment assembly through the optical elements. This may be possible through the coating or the mixture of the material with any suitable additive (doping), or plurality of additives. An additive which makes the lenses to darken in condition of very high luminosity or very high UV exposure may also be used. The optical assembly may be advantageously overmolded directly to the fabric, reducing manufacturing costs and manufacturing time and the weight of the material, since the hot material would attach to the fabric during the injection molding process.

In general the head of the optical assembly, may it be conceived with or without cup shaped counterpart, can have any of the described shaped with the described combinations: convex-concave, concave-convex, concave-concave (FIG. 38G), flat-concave, concave-flat. Two optical elements as the one in FIG. 38G may also be used together to form an optical assembly. The multi component optical assembly may comprise a fastening eyelet (e.g. similar as in FIG. 37A), which is formed to be embedded, jammed, welded or glued, to the head or eventually to the rest of the optical assembly as shown in FIGS. 28-32 and 37A, and may be embedded to the garment as an eyelet (109) (FIGS. 28-32, 37A and 37C) and may additionally have a grommet (FIG. 28) and/or may have prongs (118) (FIG. 28, 32), which may be on both sides like in FIG. 24, where opposite prongs (118) are preferably offset from each other. Alternatively in all embodiments the back surface (103) of the head portion may have one or several protrusions (118b) having the general shape of the blades of a backswept impeller as shown in FIG. 23F. Said one or more protrusions may be straight, having therefore the general shape of a straight blade impeller. Preferably the same protrusions may be also or only on the face (107) of the flange portion. Said protrusions (118b) has the effect, that by turning the optical assembly around the hole of the fabric in a first direction the fabric is forced inside the channel (101) toward the neck portion and by turning the optical assembly around the hole of the fabric in the opposite direction to the first direction the fabric is forced outside the channel and the optical assembly can be removed easier from the fabric. The optical assemblies may be already attached or glued or overmolded to an eyelet to be inserted in a hole of the fabric and bended in order to be fixed to the fabric. Said eyelet may be a prongs ring eyelet to be joined to its counter ring or a conventional eyelet to be formed on the internal side of the garment, with or without washer, or grommet. In this way optical assembly and eyelet can be fixed to the fabric together in one single step. FIGS. 28 and 32 show more in detail two of the many types of fastening means that may be used to embed the eyelet to the head of the optical assembly, wherein the head of the optical assembly is retained peripherally by a ring (123) having a c-shaped cross-section that clamps together the peripheral regions of eyelet and head portion. Such a ring (123) may have the further advantage of additionally retaining the fabric inside the channel (101) of the optical assembly. As shown in FIG. 32 the radial extremity, or perimeter, of the head of the optical assembly may be retained by the radial extremity of the eyelet, which may follow the cross-sectional shape of the head, so that the radial extremity of the eyelet may be bended inward toward the top of the dome and/or toward the collecting surface (4) of the head (104). As shown in FIG. 28 the head (104) may be fixed to the perimeter of the eyelet by an additional ring, which may have a generally V-shaped, or generally U-shaped cross section, or generally L-shaped cross section, which have the function of keeping together the radial extremity, or perimeter, of the eyelet with the perimeter of the head. Any component of the optical assembly, which includes counterparts, additional wave guiding means, eyelets and grommets, may have reflective surfaces, to reflect light inside the material or in the air, wherein the reflection is given by the material itself or by a coating. The fastening of the optical assembly may be made by heating and forming the material of the optical assembly as shown in FIG. 23A to 23E. The optical assembly of FIG. 20 or 21 may additionally have a back of the head (103) which is inclined with respect to the plane of the garment's external surface, which is perpendicular or preferably generally perpendicular to the axis X of the optical assembly, as shown on FIGS. 22, 29 and 31. The inclination may be in both directions, so that the back of the head (103) extends, along the symmetry axis X of the optical assembly in the direction of the internal side of the garment, more radially outward, as shown in FIGS. 22, 29 and 31, or more radially inward (not shown). With the back of the head (103) extending more radially outward, or in other words being tilted toward the garment as to press the fabric along the external perimeter of the head portion, the head of the optical assembly would contribute to the stability of the garment assembly (2), by helping the retention of the fabric within the neck of the head. The peripheral portion of the head may be provided with indentations or prongs (118), as shown in FIGS. 24 and 27, to better engage and retain the fabric (F). Said indentations may have a certain shape or radius in order to avoid the fabric to be damaged. Such indentations may also contribute to the anchoring of the head (104) to an attaching mean, which may be, as shown in section in FIG. 31 its supporting eyelet (109).

According to FIGS. 19, 21 it is possible to disclose a method to naturally irradiate the skin underneath a garment with sunlight (in particular UV sunlight or UVB light), by embedding in the fabric of a garment one or more optical assemblies (100) according to the embodiments described in FIGS. 19 to 39, preferably made of UVB transparent material, and optionally filtering, or absorbing, UVA light through additives or coatings. Additionally the method may include at least partially reflecting, or absorbing, at least a certain wavelength of the visible light. Alternatively the optical assembly may be transparent to visible light and/or infrared light and/or UVB light, being UV opaque. According to the method the optical assemblies may be at least partially UV transparent, in particular at least partially UVB transparent. The optical assemblies may therefore partially absorb or reflect the UVA light; additionally or alternatively, in order to protect the skin, the optical assemblies may make the light radiations diverge in order to make the radiations even softer, less dense, or less intense than the ones that would hit the skin with the direct exposition to the sun. Alternatively the method my include the application of a UVA filter, such as a cream, to the optical assembly, or to the skin covered by the optical assembly. Such a UVA sunscreen may be delivered together with the garment assembly.

FIG. 22 shows a cross sectional view A-A of the optical assembly which incorporates different optional modifications that an optical assembly may comprise in combination with each other, or taken singularly. The collecting surface (4) may have a coating layer (110) with a filter, or a material, reflecting, absorbing material, or the like, that avoids a certain light bandwidth to pass through the optical assembly, preferably a filter that at least partially avoids UVA light to pass through. Instead of using a coating, the surface may be mechanically or chemically treated. Alternatively or simultaneously the material of the optical assembly may be doped with a material (111) absorbing certain light wavelength (or that renders the compound opaque to a certain wavelength), preferably absorbing at least partially UVA light and/or preferably a portion of the visible light. The diffusing surface (3) may be flat or curved, e.g. concave or convex, or both, and it may have protuberances to further diffuse or diverge light radiations, said protuberances may be, viewed from the internal side of the garment, generally toroidal, or may be generally hemispherical, or may comprise a portion which is nearly hemispherical. The diffusing surface (and or the collecting surface) may be sanded or the like to increase the diffusion in all direction of the light and at the same time reduce the visibility of the skin from outside to the inside of the garment. The shoulder (107) may be flat or include stairs; it may have a constant cross section or an at least partially tapering cross section. As shown in FIG. 27 the dome may be divided into different adjacent surfaces, which may be flat or may have the geometry of a Fresnel lens on the external or on the internal side of the dome, or on both sides. The portions with the Fresnel lens geometry may include a Fresnel negative lens, and/or a Fresnel positive lens, and/or a Fresnel beam splitter, and/or a Fresnel prism, and/or a Fresnel cylindrical lens, e.g. a Fresnel beam splitter in the centre and a Fresnel prism peripherally. The back surface (103) of the head portion, in order to improve the reflections and therefore the light collection, or in order to adapt it better to the eyelet type, may be flat, concave (FIG. 29) or convex.

FIGS. 20-32 and 34-37 show different method for attaching the optical assembly. According to FIGS. 20 to 22 the optical assembly may be permanently or removably attached to the fabric by pushing the optical assembly into a hole of the fabric. The hole of the fabric may be made by any suitable way, e.g. by punching, sewing, embroidering, or a combination thereof, e.g. by punching and embroidering, in particular the hole may be embroidered with a thread of the same color of the fabric or of different colors, in order to make it more resistant and/or to hide the imperfections of the punched hole and/or to better seal from cold air the any between optical assembly and fabric. According to FIGS. 24 to 27 the optical assembly may be attached to the fabric by using a counter element of any suitable material, a rigid, a resiliently rigid, or an elastic material, wherein the counter element may be at least partially translucent, preferably at least partially UVB translucent, and may be made of one o-shaped or c-shaped component or multiple components e.g. two c-shaped components joined together into an o-shaped component. An additional resilient component, e.g. a generally U-shaped or generally C-shaped metal fastener (not shown), may be used to retain the optical assemblies of FIGS. 24-27 and of FIG. 37*a*-37C with its counterpart (114). The counter element (114) may be itself a guiding and/or diffusing and/or reflecting and/or comfort element, and therefore it may be formed as to deflect light in different ways e.g. like a converging or diverging lens, or a Fresnel lens, which may also be converging or diverging. The fixing means of FIG. 24-32, of FIG. 37*a*-37C and FIG. 41A-41D may comprise a bayonet coupling. According to FIG. 23A to 23E the optical assembly may be fixed to the fabric by fusing and forming a portion thereof, which may be the head (FIG. 23D) or the flange portion (FIG. 23A, 23B, 23C, 23E). A variation of FIG. 23C may include a joining mechanism as shown in FIG. 24 between the component of FIG. 23C before forming, which is considered in this variation the head of the optical assembly and a counter element (114). Said joining mechanism may include forming, jamming, gluing, friction coupling, ultrasonic welding or the like. The joining mechanism may have a central pin or several lateral pins to be inserted into a ring or grommet with holes or formed around a grommet. According to FIG. 23A to 23E the optical assembly may be inserted in a fabric that may not have a pre-existing hole, but it may have a pointed tip which pushed into the fabric may diverge or break the fibers and therefore crate a seat. The so mounted optical assembly may be later heated and formed to a permanent or non permanent fixation to the garment. According to FIGS. 28 to 32 and 37A to 37C the optical assembly may be fixed to the fabric with an eyelet. According to FIG. 36, but possibly also in other embodiments, the optical assembly may have a hole (108) to be used to be fixed to the fabric with a rivet or a thread or a string, being therefore embroidered to the garment, while it may additionally be attached to the garment with another method, e.g. in FIG. 34-36 through holes in the garment. As shown in FIG. 28, 29, 31, 32, 33, 37A the section of the head of the optical assembly is D-shaped, or arc shaped, so that the head may preferably have the three-dimensional shape of a bowl, or preferably of a portion of a generally hemispherical bowl, which is thinner in the middle and thicker on the perimeter, wherein the back of the head and may be attached in different ways to an eyelet (109), which may be a round, triangular, squared, or generally polygonal or may be an elongated round eyelet, or a rectangular eyelet. Preferably the neck of the optical assembly may be formed exclusively by the eyelet (FIG. 28, 30, 31); however a portion of the head (FIG. 30), or of another portion of the optical assembly (FIG. 37), may enter the eyelet to fix the head of the eyelet by friction, with a coupling with interference. According to FIGS. 34 to 37 the optical assembly may further extend underneath the fabric, guiding the light toward a remote place, e.g. a different part of the body, or underneath another garment. A flexible light guide extension of the optical assembly may be made of a bunch of round and thin optical fibers, or by a film ream of any suitable material (e.g. PMMA or COC), so that it can be easily manufactured, by cutting a film in any suitable shape and obtaining the wished thickness by adding several film layers on top of each other. An additional optical assembly may be connected to the optical assembly of FIGS. 20 to 32. In order to easily guide light toward a remote region, a second guiding means (8") or a plurality of second guiding means (8'), coupled with a first guiding means (8') by optical coupling means (18), may be used. The second guide element or the plurality of guiding elements may be flexible and may have a reinforcing structure to avoid excessive bending, and may be detachable, to easily wash the garment assembly. The plurality of second guiding means may be organized in a bundle and extend away from the optical assembly of FIGS. 20 to 32. To make the light converge into an optical element, or light guiding element, having a smaller cross section the head of the optical assembly may be modified as shown in FIG. 37B, wherein the internal surface of the head is convex, while the external is dome shaped, or concave, building therewith a positive lens. A plurality of optical assemblies exposed from the external surface of the garment may be attached together on the internal side of the garment, as shown in FIGS. 34-36, and they may guide the light generally in the same direction with which the light is entering the optical assembly (FIG. 34, 35), or may reverse the direction (FIG. 36). A second portion (8''') of light guiding means (8) extending from the optical assembly, e.g. of FIG. 21, may comprise a single light guiding means of a plurality of guiding means e.g. bunch of thin optical fibers. The advantage of having thin optical fibers is that, by equal total transversal cross section area, they are more flexible than a single one. To support the optical fibers from bending and or breaking a support can be added to the fibers, so that they are embroidered or wrapped or just attached to said support. Said support may be a tubular or flat plastic rod, with the fibers going outside it, or a void plastic or metal pipe or plastic or metal spiral which may be a spring or not, with the fibers passing inside it. The fibers or bunch of fibers may be permanently installed in the garment or may be removable for example for washing. In some embodiments, see for example FIGS. 24-27 and 37A-

37C the locking mechanism (18), e.g. the click into place locking mechanism, when the components are mounted on a piece of fabric, may cause the clamping of the fabric between the components of the optical assembly, e.g. by pushing the fabric with the counter element (114) against the back of the head (103) during the mounting process, so that when the counterpart is jammed and released, the expanding fabric, behaves like a spring, generating a contact pressure between two engaging surfaces of respectively the first (8') and the second (8") portion of the optical assembly, generally in the direction of the axis (X) of the optical assembly, assuring therewith a robust fabric retention. FIGS. 33A-33C and 38A-38F and 39 show some optical simulations on a preferred embodiment of the optical assembly according to FIGS. 19-32 and 34 to 37 or of a portion thereof. FIGS. 33A to 33C show the cross-sectional arc-shape of the optical assembly (100) or a portion thereof, e.g. the head (104) of the optical assembly, with simulated parallel rays of incident light (11), which represent the light of a very far light source like the sun, wherein said light rays have in each figure a different direction. The optical assembly (100) shown would have a Notably the arc shaped section of FIG. 33, or its generally 3d bowl geometry, has no neck portion and the back surface (103) of the head portion (104) is considered to be its attaching means for the fabric. The optical assembly (100) may comprise only the head portion, which is the case of the flange and the neck thickness being equal to zero. It may be advantageous for increasing the attaching surface of the back side (103) of the head portion (104) to have protrusions or grooves extending therefrom (being embossed or debossed), or alternatively the back of the head may be undulated in radial and/or in circumferential direction. In general, for all embodiments, the thickness of the flange may vary between 0 mm and 5 mm, and the thickness (D−Di) of the neck portion between 0 mm and its external dimension (D).

Grooves, protrusions or undulations on the back of the head and/or in the flange portion (106), may be present also in the embodiments of FIGS. 19-32 and 34-39 and may have the additional effect of stretching the fabric during the overmolding or the assembly process, since with an (e.g. undulated) geometry of the optical assembly or of the molding tool the fabric may at least partially forced to take the shape of the undulations and may create a special effect on the fabric and/or improve the overmolding process on the internal surface (5) of the fabric. In FIG. 33A the incident light (11) has an inclination, with respect to the axis (X) of the optical assembly, of about 45°. In FIG. 33B the incident light (11) has an inclination, with respect to the axis (X) of the optical assembly, of about 70°. In FIG. 33C the incident light (11) has an inclination, with respect to the symmetry axis (X) of the optical assembly, of about 0°. In all cases the incident light (11) converges after entering the external collecting surface (4) of the head portion, in order to allow the highest amount of incident light within the reach of the neck portion of the optical assembly, and the guided light (10), after exiting the diffusing back surface (3) of the head portion, diverges, propagating as diffused light (14). From the figures it can be seen that such a shape of the head portion allows to capture light radiations (11) from all directions and to redistribute the light on the internal side of the garment assembly (2), or of the optical assembly in a diverging manner. It is moreover visible that the light rays before hitting the head portion are closer to each other than the light rays that hit the lower end of the picture, which is the closest position at which the skin of a user wearing the garment assembly having such an optical assembly could be. This shows that in any case the developed optical assembly allows redistributing the light safely on wide areas of the skin.

FIG. 40 shows a graphic representation of the relationship between the diffused light density per unit of area (113) and the ratio D/hd (112) of the diameter of the hole (D) formed by the optical assembly in the garment and the height of the dome of the optical assembly from the garment external surface. The simulated geometries of the head of the optical assembly has a ratio D/hd of about 2,5. A representation of the relationship between the collected light quantity (113) hitting the collecting means (4) at different angles and the ratio D/hd (112) of the diameter of the hole (D), formed by the optical assembly in the garment, and the height (hd) of the dome of the optical assembly from the garment external surface, is shown in FIG. 40. The ratio D/hd (112) may be between 1,1 and 6, or preferably between 2 and 5, or more preferably between 2,2 and 4,8. A ratio closer to 1.1 means a dome geometry which is closer to an hemisphere, while a ratio D/hd closer to 6 means a dome geometry which is flatter and therefore closer to a spherical cap, or a paraboloid cap, or a spherical segment, or a cylindrical mantel portion which may have the cross section being generally rectangular, or rounded rectangular, or elliptical. A flatter dome performs slightly better at collecting light radiations which are generally directed at 0° with respect to the axis (X) of the dome, or generally perpendicular to the garment surface to which the optical assemblies are embedded, while a rounder dome, closer to the hemispherical shape, perform slightly better for collecting inclined light radiations with respect to the axis of the dome. Considering the same light radiation intensity from all three directions AL (0°, 45° and 70°) and no reflection between neighboring optical elements, a ratio D/hd of about 4 may be advantageous. May the inclined light radiation be higher than the perpendicular one, a ratio D/hd of 2 to 3 may be advantageous. Generally it is conceivable that on different places of the garment assembly, different shape of the head of the optical assembly may be appropriate. However, using the same shape of the head of the optical assembly all over the garment wouldn't be very disadvantageous, since the garment in use is not always in the same position and the light radiations, which include direct, reflected and diffused light, come from different directions. Moreover some light which is not collected by a certain collecting means may be reflected into a neighboring light collector, which may collect it. Advantageously, for maximizing the light collected, the dome shaped light collecting means (4) may be placed very closed to each other, e.g. with a honeycomb like structure, as shown in FIG. 19, and may be configured to be more efficient in collecting angled light with respect to their axis, so that the small portion perpendicular light which may be reflected laterally, may be collected by the neighboring optical assembly, wherein, preferably, the peripheral portion of the head may be cut to generally follow the hexagonal shape of the honeycomb, allowing to have more optical assemblies per surface area. It may be conceivable, that in colder months of the year in the northern hemisphere, when at noon the sun doesn't go as high and the maximal angle of altitude of the sun above the horizon is between about 27° and about 51°, the average angle (AL) of the light hitting the optical assembly may be about 30°, the optimal ratio D/hd may be preferably between 1,5 and 4, or more preferably between 1,5 and 2,5.

The geometry of the head of the optical assembly, having e.g. at least partially the shape of a negative meniscus lens, shown in FIG. 21 and in FIG. 33A-33C may be reduced to a thinner Fresnel lens, preferably a negative Fresnel lens, while generally conserving the optical properties of the original negative meniscus lens shape. The Fresnel geometry may be simplified using straight segments in order to simplify manufacturing. Also in the case of a Fresnel geometry, the cross section of the lens may have a rotational symmetry, or may have an elongated shape in the direction perpendicular to the cross section, so that the shown cross section maybe located on a symmetry plane, and the resulting Frensel lens would be a generally cylindrical Frensel lens, which may have rounded ends. A flatter head (104) may be advantageous for the comfort of the garment, and/or for the distinction from male and female clothing, and/or for the distinction between sport and more fashionable clothing. A head with a sharp edged head may be more suitable for male clothes or for sport clothes. Using a Fresnel lens instead of a dome shaped collecting surface (4) the concave diffusing surface (3) is replaced by a generally flat surface, therefore the void between the diffusing surface (3), shown e.g. in FIG. 21, is missing and causing the internal surface of the garment assembly (2) being on the same plane with the diffusing surface on the back side of the Fresnel lens. In this case the light radiations, preferably the UVB radiations, have less space to diverge, before potentially reaching the skin when the garment assembly is worn. The use of a Fresnel lens geometry may be more suitable when the sunlight is very low, when an higher light concentration is needed, alternatively an additional spacer may be used between the lens and the internal side of the garment assembly, in order to increase the distance between the internal side of the garment and the skin of the person wearing the garment assembly. A Fresnel lens, preferably a positive or converging one, may be also suitable to converge light into an additional optical assembly and/or into an optical fiber, or to diverge a light source coming from a light guiding means (8), or preferably an optical fiber. FIG. 39 shows a Fresnel lens geometry that may be used as a diffusing means and may be used to diverge the light coming from a light guiding means (8) or any point light source within the optical assembly. As shown in FIG. 39, the simulated incoming light rays are diverging from a point source, which may be a simplification of the light rays (10) coming from an optic fiber, or the head (104) of the optical assembly (100) or from a light collecting means (4) in general. FIG. 39 may be also a collapsible Fresnel lens that becomes a dome, if pressed.

FIG. 38A-38F show different combinations of the optical assembly with a head portion (104) and an integral or detachable counter element; both may have the shape of a diverging optic. For example the component (114) of FIG. 38E may be a Fresnel lens like the one of FIG. 39.

Figure 41:
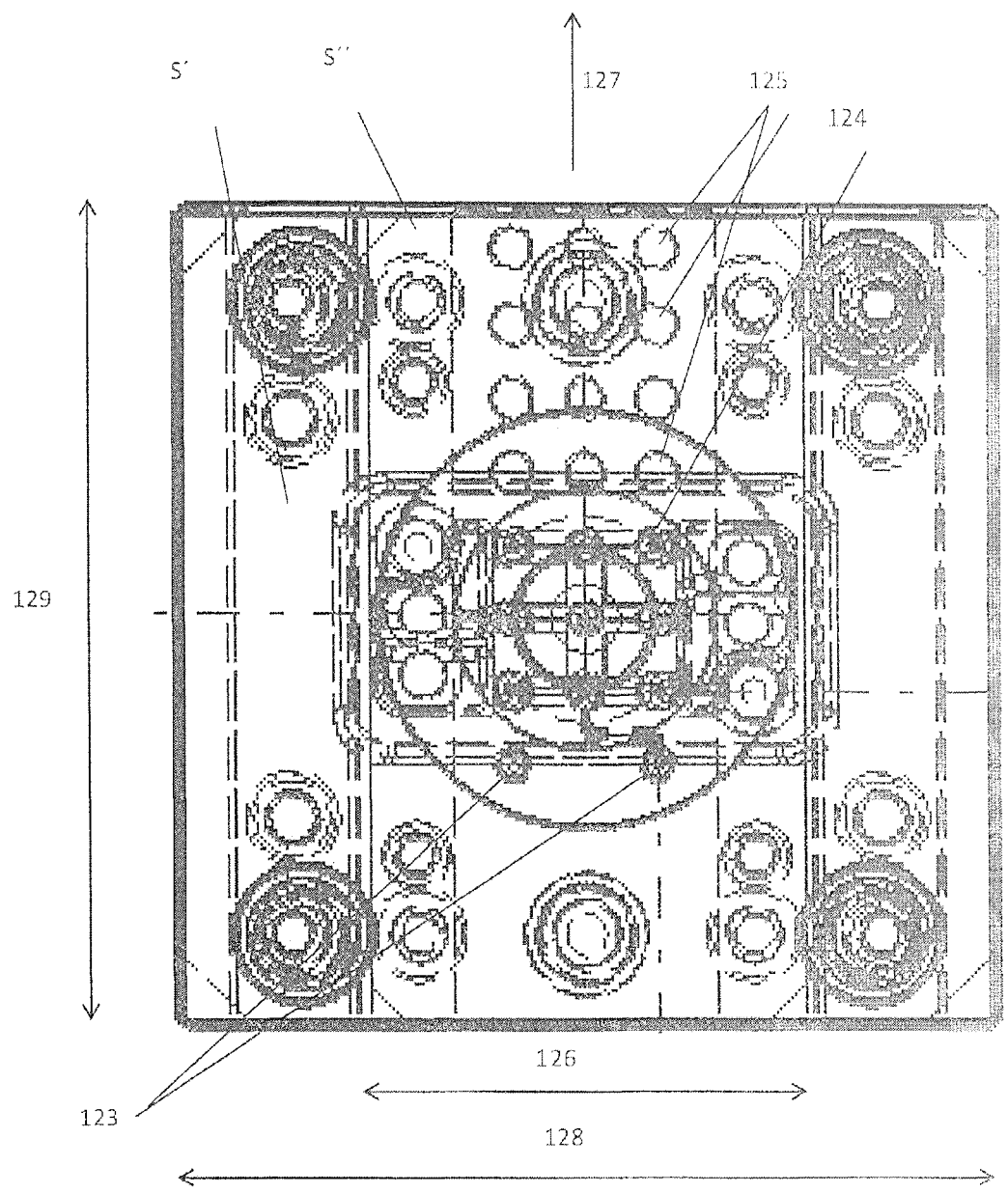
FIG. 41 shows a front view of a molding tool cavity to produce the garment assembly or a portion thereof, preferably with a fabric in mold plastic injection.

FIG. 41 shows the front view (from the top of one of the matrix) of a portion of the injection molding tool, having a first surface (S') on which the mold closes, a second surface (S"), which may have an adjustable height, with respect to the first surface (S'), (and therefore may have the same of a different height than the first surface), where the fabric (for the preferably fabric in mold manufacturing process) is located, said second surface having a width (126), which may be smaller than the total width of the matrix (128), and a length (129), which may be equal to the length of the matrix. The injection molding tool may additionally have at least a fixing means (123) (which may be inserted in the pre-manufactured holes of the fabric) for positioning and holding the fabric in place during the closure of the tool, molding cavities (124) (nine in the present case) and receptacles (125) for temporarily storing the optical assemblies (100) (or the portions of optical assemblies), which have already been molded and moved forward in the direction (127) with the fabric, but are still within the matrix waiting the subsequent adjacent series of optical assemblies (or the portions thereof) to be molded. Such a tool allows the injection molding of relatively long portions of garment assembly with series of optical assemblies very close to each other with a small molding tool. The receptacles additionally help keeping the fabric in position, preventing the stretching of the fabric portion that is going to be overmolded (because of its own weight). It is therefore possible to disclose a fabric in mold manufacturing method comprising the steps of: providing a molding tool as described above, providing a strip of fabric with multiple series of holes along its length, each of said series of holes corresponding to the position of the molding cavities of the molding tool, preferably with the diameter of the holes being generally equal or smaller than the diameter of the neck portion of the optical assembly, positioning a strip of fabric on the second surface (5") of the matrix (preferably within the width (126) of said second surface), so that at least a series of holes lye over the injection molding cavities, so that a portion of the fabric around each hole is inside the respective cavity in order to be overmolded, and that at least a hole is centered and hold on the fixing means (123), injection molding a series of optical assemblies, (or a series of a portion thereof), moving the garment assembly forward in direction (127) of a length equal or higher of the footprint of the molded series of optical elements (taken in direction (127) of the movement) as to position at least another hole on the fixing means (123) and at the same time to position, optionally, at least a portion of the already injection molded optical assemblies (or a portion thereof) on the receptacles (125) before optionally injection molding another series of optical assemblies. Optionally the fabric may be wetted before injection molding and/or a layer of material (e.g. paper, aluminum, other fabric, etc) may be (removably or partially removaby) positioned on one or both sides of the fabric in order to easily detach some unwanted molded portions (e.g. flash) from the fabric after molding or to provide a reflecting and/or comfort layer to the garment assembly. Alternatively to providing a fabric with holes, the fabric may be manufactured to have a relatively thin and breakable mesh in correspondence to the holes, said mesh to be broken by the pins of the injection molding tool or by the molded plastic itself during the molding process. The holes or slots may be manufactured in the fabric with or without material removal, the holes may therefore be round, triangular, elliptical, squared, polygonal, or may be made by a minus-shaped, a plus shaped, an x-shaped, or a y-shaped cut. During the injection molding of the material, the portion of the fabric around each hole which is inside the respective cavity may change shape mixing with the injected material, and may be folded or compressed toward the perimeter of the optical assembly, taking an irregular shape which increases the retention of the fabric itself inside the channel (101) of the optical assembly. Interconnections between the optical assemblies, preferably being light guiding means to transfer the light more remotely than the immediate region behind the light collecting means, on the opposite internal side of the garment assembly, may be molded on fabric between the optical assemblies. In this case between the cavities (124) (and therefore between the receptacles (125)) the matrix shown (or its counterpart) may have grooves. Optionally the tool comprises a preferably adjacent hole manufacturing portion where the holes (or the slots) are stamped, cut or drilled on the fabric, so that during the injection molding process on a first area of the fabric, holes may be stamped on a second portion of the fabric, preferably connected to the first portion of the fabric. The fabric removed from the hole may be sucked or blown away with air; in particular, in case the fabric may be cut by a rotating cylindrical tool empty in the centre, the fabric which is cut away may be sucked or blown away by air passing through the empty optionally rotating cutting tool. The manufacturing of the hole or slot may be performed before or after the optional reinforcing embroidery made around the perimeter of the hole or eyelet. The subject matter may also be defined by following statements:

A garment assembly (2), having an external surface (6), defining an external side (24), and an internal surface (5), defining an internal side (23), said garment assembly (2) comprising, at least a light guiding means (8) extending from the external surface (6) to the internal surface (5) and allowing light communication between the external side (24) and the internal side (23) of the garment assembly, and further comprising:

a first part (12') comprising the external surface (6), a first light guiding means portion (8') having at least a light collecting means (4) facing the external side (24) of the garment assembly (2) and a second part (12") comprising an internal surface (5), a second light guiding means portion (8") having at least a light diffusing means (3) facing the internal side (23) of the garment assembly (2), preferably wherein the garment assembly comprises at least a piece of fabric and that the wave guiding means (8) comprises attaching means to permanently or detachably fix said wave guiding means to said fabric, preferably wherein the light guide (8) is at least partially translucent to at least a portion of the UVB light, preferably to at least a portion of the UVB light having the wavelength in the range between 290 nm and 300 nm, preferably wherein the light guiding means (8) is at least partially opaque to a certain light bandwidth, in particular wherein the light guiding means include light absorbing or light reflecting means, optionally in the form of a coating (110) or a doping agent (111), to selectively absorb, or reflect a certain light bandwidth, preferably at least a portion of the UVA bandwidth and/or preferably at least a portion of the visible light bandwidth, preferably wherein the light guiding means (8) comprises a head portion (104), preferably a neck portion (105), adjacent to the head portion, and preferably a flange portion (106), adjacent to the neck portion, wherein the head portion (104) has the general shape of a negative meniscus lens, said negative meniscus lens having a convex surface (4), facing the external side (24) being the light collecting means (4) and a concave surface (3), facing the internal side (23), being the light diffusing means (3), wherein convex surface has a greater curvature radius than the concave surface, and wherein the convex (4) and the concave (3) surfaces are delimited by a plane perpendicular to the axis (X) of the light guiding means (8) to form a preferably circular or elliptical or polygonal ring shaped back portion (103) of the head portion (104), preferably wherein the ratio between the internal dimension of the ring (D) and the height (hd) of the apex of the convex surface (4) of the head, with respect to the plane passing through the back surface (103) of the head (104) is between 1 and 6, or preferably between 2 and 5, or more preferably between 2,2 and 4,8, preferably wherein the first part (12'), and he second part (12'), are detachably joined, preferably through optical coupling means (18), preferably wherein the first part (12') is configured to be worn over another garment and the second part (12') is configured to be worn with its internal surface (5) in direct proximity to the skin, preferably wherein the wave collecting means (4) has a wave collecting surface, which is larger than the area of the smallest cross section taken perpendicularly to the axis (X) of the waves guiding means (8), preferably further comprising a light reflecting means (15) on the internal surface (5), so that the light diffused by the diffusing means (3) is reflected in the right direction, toward the internal side (23).

Light guiding means (8), for the garment assembly of claim 1, comprising a head portion (104), preferably a neck portion (105), adjacent to the head portion, and preferably a flange portion (106), adjacent to the neck portion, wherein the head portion (104) has the general shape of a negative meniscus lens, said negative meniscus lens having a convex surface (4), facing the external side (24) being the light collecting means (4) and a concave surface (3), facing the internal side (23), being the light diffusing means (3), wherein convex surface has a greater curvature radius than the concave surface, and wherein the convex (4) and the concave (3) surfaces are delimited by a plane perpendicular to the axis (X) of the light guiding means (8) to form a preferably circular or elliptical or polygonal ring shaped back portion (103) of the head portion (104), preferably wherein the ratio between the internal dimension of the ring (D) and the height (hd) of the apex of the convex surface (4) of the head, with respect to the plane passing through the back surface (103) of the head (104) is between 1 and 6, or preferably between 2 and 5, or more preferably between 2,2 and 4,8. Use of said light guiding means (8), to form the garment assembly (2) of claim 1 for irradiating the body under the garment assembly with natural sunlight.

Method for irradiating the skin with natural light by wearing, on the sunlight, the garment assembly described above preferably comprising said light guiding means (8).

Injection molding tool, or portion thereof, for a fabric in mold manufacturing process, for manufacturing the garment assembly of claim 1, having a first surface (S') on which the mold closes, a second surface (S'), having an adjustable height with respect to the first surface (S'), said second surface having a width (126), which is smaller than the total width of the matrix (128), and a length (129), which is preferably equal to the length of the matrix, at least a fixing means (123), for positioning and holding the fabric in place during the closure of the tool, at least a molding cavity (124) and a receptacle (125) for temporarily storing the optical assemblies (100), or a portion thereof, which have already been molded and moved forward in the direction (127) with the fabric, but are still within the matrix waiting the subsequent adjacent series of optical assemblies, or the portions thereof, to be molded.

Method for manufacturing the garment assembly described above comprising the steps of: —providing a molding tool having at least a molding cavity, —providing a strip of fabric with multiple of holes, —positioning the strip of fabric on a surface of the tool so that at least a first hole lye over the injection molding cavity, —injection molding of at least a light guiding means (8) (or a portion thereof), —repositioning the garment assembly shifting it of a length equal or higher of the footprint of the molded light guiding means (8) as to position a second hole, preferably adjacent to the first hole, over the molding cavity and preferably the already injection molded light guiding means (8) (or portion thereof) on a receptacles (125) preferably adjacent to the molding cavity, for storing the injection molded light guiding means (8) during the closure of the molding tool for a new injection molding step, —optionally injection molding another light guiding means (8) on said preferably adjacent second hole.

Alternatively to the fabric over molding, the the garment assembly, or a portion thereof, may comprise a base layer at least partially made of resilient plastic, preferably of vowen or non-vowen plastic fabric or plastic fabric film, said base layer may be suitable to sew to a fabric, or to another base layer, said base layer may have a thickness, which may be costant or not, the thickness may be from about 0,1 mm to about 4 mm, preferably from about 0,5 mm to about 2 mm, and may comprise embedded optical assemblies, said optical assemblies may extend form one side to the other side of the base plate, and may have the characteristics of the optical assemblies described in FIG. 1-40. Said base layer may also be made of neoprene or the like. The garment assembly may be made by a two step injection molding process, so that the base plate may be molded (or alternatively laminated, or vulcanized) first and the optical elements may be overmolded to the base layer. The first molding step may therefore comprise the injection molding of a base layer comprising several holes of any geometry through which the optical elements may be overmolded. The garment assembly having the resilient plastic base layer, or a portion thereof, may still include a fabric layer with holes to be overmolded by the base plate, in a first injection molding step, and by the optical assembly, in a second injection molding step. The fabric layer may however not be necessary, since the base layer may replace completely the fabric layer. Replacing the fabric layer by an injection molded base layer (or eventually replacing it by a pre-manufactured, preferably laminated, or vulcanized base layer) and overmolding it with the optical assemblies, would make the process faster and cheaper and the result would be a more robust garment assembly, or portion thereof. Both cases (the two step injection molding and the overmolding of a base layer made of a pre-manufactured plastic film, or a synthetic fabric, or a partially synthetic fabric) may imply that the extremities of the optical assembly are at least partially fused together with the base layer.

Alternatively to the fabric over molding, the manufacturing method may include a step of over molding a base layer at least partially made of resilient plastic, or the like, that would be placed in the molding tool instead of the fabric (or additionally to the fabric). Another possible method of manufacturing the garment assembling or a portion thereof is through a 2 step injection molding process. The first step may include the molding of a, preferably thin, layer of resilient plastic having holes for the optical elements, wherein said optical elements may be over molded to form the optical assemblies on the holes of the, preferably thin, layer in the second injection molding step. The margins (which may be the about 10 mm portion of base layer around its perimeter, that may not have any optical assembly) of the base layer, which may be made of resilient plastic or the like, may be sewed to a fabric, or to another base layer to form the garment assembly. This method, of overmolding a base layer wich is at least partially made of plastic, preferably of a plastic that has a fusion temperature which is equal or lower than the fusion temperature of the optical assembly, has the advantage that the optical assembly and the thin layer are attached robustly to each other by the injection molding process itself and that the resulting overmolded assembly is faster and cheaper to produce. The thin plastic layer might advantageously be made in different colors, thickness, flexibility.

The invention claimed is:

1. Method for manufacturing the garment assembly, said garment assembly comprising: an interior surface facing an internal side of the garment assembly and an exterior surface facing an external side of the garment assembly, and an embedded optical assembly comprising: at least a wave collecting means for collecting light waves hitting the exterior surface from the external side of the garment assembly, at least a wave diffusing means facing the internal side of the garment assembly, at least a wave guiding means, extending from the collecting means to the diffusing means, wherein the wave collecting means have a light wave collecting area which is larger than the area of the smallest cross section of the wave guiding means and wherein the optical arrangement is made of an UV transparent or UV semitransparent material comprising the steps of: providing a molding tool having at least a molding cavity, providing a strip of fabric with multiples holes, positioning the strip of fabric on a surface of the molding tool so that at least a first hole lies over the injection molding cavity, creating at least a light guiding means by injection molding using said molding cavity, repositioning the garment assembly by shifting it a length equal or higher of a footprint of the molded light guiding means so as to position a second hole.

* * * * *